(12) United States Patent
Kawase et al.

(10) Patent No.: US 7,074,777 B2
(45) Date of Patent: Jul. 11, 2006

(54) VITAMIN D DERIVATIVES

(75) Inventors: Akira Kawase, Shizuoka (JP); Hitoshi Shimizu, Tokyo (JP); Kazuki Shimizu, Shizuoka (JP); Takashi Emura, Shizuoka (JP); Kazutomo Kinoshita, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 163 days.

(21) Appl. No.: 10/257,868

(22) PCT Filed: Apr. 18, 2001

(86) PCT No.: PCT/JP01/03310

§ 371 (c)(1),
(2), (4) Date: Oct. 17, 2002

(87) PCT Pub. No.: WO01/79166

PCT Pub. Date: Oct. 25, 2001

(65) Prior Publication Data

US 2003/0195176 A1    Oct. 16, 2003

(30) Foreign Application Priority Data

Apr. 19, 2000   (JP)   ............... 2000-117791

(51) Int. Cl.
*A61K 31/59*   (2006.01)
*C07C 401/00*   (2006.01)

(52) U.S. Cl. ............ 514/167; 552/653; 514/863

(58) Field of Classification Search ......... 552/653; 514/167
See application file for complete search history.

(56) References Cited

U.S. PATENT DOCUMENTS

| | | | |
|---|---|---|---|
| 4,891,364 A | 1/1990 | Kubodera et al. | |
| 5,824,811 A | 10/1998 | Kubodera et al. | |
| 6,184,398 B1 | 2/2001 | Kawase | |

FOREIGN PATENT DOCUMENTS

| | | |
|---|---|---|
| EP | 0 755 922 | 1/1997 |
| EP | 0 947 504 | 10/1999 |
| JP | 61-267550 A | 11/1986 |
| JP | 6-72994 A | 3/1994 |
| JP | 7-330714 A | 12/1995 |
| JP | 10-231284 A | 9/1998 |
| WO | WO 90/09991 | 9/1990 |
| WO | WO 94/14766 | 7/1994 |
| WO | WO 98/28266 | * 2/1998 |

OTHER PUBLICATIONS

Norman et al., "Structure-Function Studies of the Side Chain of 25-hydroxyvitamin D3.", J. of Biological Chemistry, vol. 254(22), pp. 11445-11449, 1979.*

Johnson et al., "Studies on Vitamin D (Calciferol) and Its Analogues. 10. Side-Chain Analogues of 25-Hydroxyvitamin D3."J. of Medicinal Chemistry, vol. 20(1), pp. 5-11, 1977.*

E. Murayama, et al "Synthetic Studies of Vitamin $D_3$ Analogues. VIII.Synthesis of 22-Oxavitamin $D_3$ Analogues," Chem. Pharm. Bull., 34(10), 1986, pp: 4410-4413.

(Continued)

*Primary Examiner*—Barbara P. Badio
(74) *Attorney, Agent, or Firm*—Browdy and Neimark, PLLC

(57) ABSTRACT

The object of the present invention is to provide a vitamin D derivative exhibiting excellent physiological activity as medicines, in particular as therapeutic agents for skin disease including psoriasis, and having decreased hypercalcemic activity.

The present invention provides vitamin D derivatives represented by the general Formula (1):

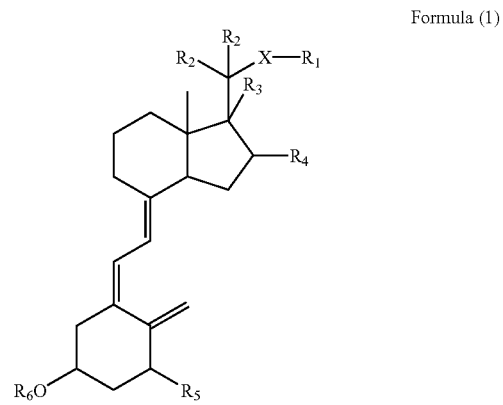

Formula (1)

wherein
in Formula (1), X is oxygen or sulfur;
$R_1$ is hydrogen or Formula (2)

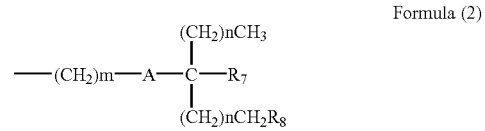

Formula (2)

$R_2$ is hydrogen or alkyl;
$R_3$ and $R_4$ are hydrogen or alkyl or $R_3$ and $R_4$ together form a double bond between the 16- and 17-positions;
$R_5$ is hydrogen or —$OR_{13}$ in which $R_{13}$ is hydrogen or a protecting group; and
$R_6$ is hydrogen or a protecting group.

11 Claims, No Drawings

OTHER PUBLICATIONS

Kubodera, Noboru et al "An Improved Procedure for Retro-Cycloaddition of Adducts from Steroidal 5,7-Dienes and 4-Phenyl-1,2,4-triazoline-3,5-dione" J. Org. Chem. 1992, 57 pp:5019-5020.

Laronck, Richard C. "Comprehensive Organic Transformations; A Guide to Functional Group Preparations" 2nd. Ed. WILEY-VCH (1999) pp: 689-702.

* cited by examiner

VITAMIN D DERIVATIVES

TECHNICAL FIELD

The present invention relates to novel vitamin D derivatives, and more particularly, relates to vitamin D derivatives useful as medicines (such as therapeutic agents for skin diseases including psoriasis).

BACKGROUND ART

In vivo, vitamin $D_3$ is led to 25-hydroxyvitamin $D_3$ in liver by the hydroxylation of the 25-position and then led to 1α,25-dihydroxyvitamin $D_3$ or 24R,25-dihydroxyvitamin $D_3$ by the hydroxylation of the 1α- or 24-position, respectively. Among those metabolites, for example, 1α,25-dihydroxyvitamin $D_3$ and its synthetic analogues are known to have various physiological activities such as calcium metabolism regulatory activities, growth inhibitory and differentiation inducing activities for tumor cells, and immunoregulatory activities.

Long-term and continuous administration of vitamin $D_3$ has tended to have a disadvantageous effect of causing hypercalcemia. To solve this problem, synthesis of various vitamin D derivatives is discussed and vitamin D derivatives having a reduced hypercalcemic effect have been proposed (e.g., JP No. 7-330714 A and JP No. 10-231284 A).

DISCLOSURE OF THE INVENTION

An object of the present invention is to provide a novel vitamin D derivative exhibiting excellent physiological activity as medicines, in particular as therapeutic agents for skin disease including psoriasis, and having decreased hypercalcemic activity.

To achieve the above object to provide vitamin D derivatives having reduced hypercalcemic activity, the inventors of the present invention intensively studied compounds having either oxygen or sulfur at the 22-position. As a result of such studies, the inventors of the present invention have found that the stated object could be achieved by providing vitamin D derivatives of the following Formula (1) and thereby completed the present invention.

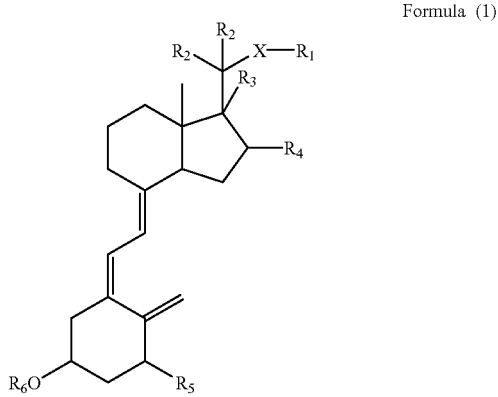

Formula (1)

wherein
in Formula (1), X is oxygen or sulfur;
$R_1$ is hydrogen or Formula (2)

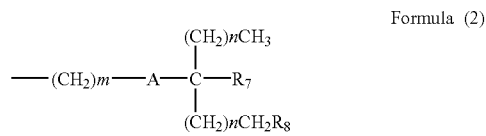

Formula (2)

wherein
in Formula (2), A is —CO—, —$CR_9R_{10}$— (in which $R_9$ and $R_{10}$ are hydrogen or hydroxy), —$CR_{11}$=$CR_{12}$— (in which $R_{11}$ and $R_{12}$ are hydrogen or alkyl) or —C≡C—, $R_7$ and $R_8$ are hydrogen or optionally protected hydroxy, m is a number from 0 to 4 and n is a number from 0 to 2;

$R_2$ is hydrogen or alkyl;

$R_3$ and $R_4$ are hydrogen or alkyl or $R_3$ and $R_4$ together form a double bond between the 16- and 17-positions;

$R_5$ is hydrogen or —$OR_{13}$ (in which $R_{13}$ is hydrogen or a protecting group); and $R_6$ is hydrogen or a protecting group.

In other words, according to the present invention, vitamin D derivatives of Formula (1) are provided.

Preferably, X is oxygen or sulfur; $R_1$ is hydrogen or Formula (2) (in which A is —CO—, —$CH_2$—, —CH(OH)—, —CH=CH— or —C≡C—, $R_7$ is hydroxy, $R_8$ is hydrogen, m is a number from 0 to 2 and n is a number from 0 to 1); $R_2$ is hydrogen or $C_{1-4}$ alkyl; $R_3$ and $R_4$ are hydrogen or $R_3$ and $R_4$ together form a double bond between the 16- and 17-positions; $R_5$ is hydroxy; and $R_6$ is hydrogen in Formula (1).

Preferably, X is oxygen or sulfur; $R_1$ is Formula (2) (in which A is —CO—, —$CH_2$—, —CH(OH)—, —CH=CH— or —C≡C—, $R_7$ is hydroxy, $R_8$ is hydrogen, m is a number from 0 to 2 and n is a number from 0 to 1); $R_2$ is hydrogen or methyl; $R_3$ and $R_4$ together form a double bond between the 16- and 17-positions; $R_5$ is hydroxy; and $R_6$ is hydrogen in Formula (1).

Preferably, X is oxygen or sulfur; $R_1$ is Formula (2) (in which A is —CO—, —$CH_2$—, —CH=CH— or —C≡C—, $R_7$ is hydroxy, $R_8$ is hydrogen, m is a number from 0 to 1 and n is a number from 0 to 1); $R_2$ is hydrogen or methyl; $R_3$ and $R_4$ together form a double bond between the 16- and 17-positions; $R_5$ is hydroxy; and $R_6$ is hydrogen in Formula (1).

Preferably, X is oxygen; $R_1$ is Formula (2) (in which A is —$CH_2$— or —C≡C—, $R_7$ is hydroxy, $R_8$ is hydrogen, m is 1 and n is a number from 0 to 1); $R_2$ is hydrogen or methyl; $R_3$ and $R_4$ together form a double bond between the 16- and 17-positions; $R_5$ is hydroxy; and $R_6$ is hydrogen in Formula (1).

Preferably, X is oxygen; $R_1$ is Formula (2) (in which A is —C≡C—, $R_7$ is hydroxy, $R_8$ is hydrogen, m is 1 and n is 0); $R_2$ is hydrogen or methy; $R_3$ and $R_4$ together form a double bond between the 16- and 17-positions; $R_5$ is hydroxy; and $R_6$ is hydrogen in Formula (1).

Preferably, X is oxygen; $R_1$ is hydrogen or Formula (2) (in which A is —$CH_2$—, $R_7$ is hydroxy, $R_8$ is hydrogen, m is a number from 1 to 2 and n is a number from 0 to 1); $R_2$ is hydrogen; $R_3$ and $R_4$ are hydrogen; $R_5$ is hydroxy; and $R_6$ is hydrogen in Formula (1).

According to another aspect of the present invention, there is provided a pharmaceutical composition comprising the above-mentioned vitamin D derivative.

According to another aspect of the present invention, there is provided a therapeutic agent for skin diseases comprising the above-mentioned vitamin D derivative as an active ingredient. Preferably, the skin disease to be treated is psoriasis.

According to yet another aspect of the present invention, there is provided use of the above-mentioned vitamin D derivative in the manufacture of a therapeutic agent for skin disease. Preferably, the therapeutic agent for skin disease is used for the treatment of psoriasis.

According to yet another aspect of the present invention, there is provided a method of treating a skin disease using the above-mentioned vitamin D derivative. Preferably, the skin disease to be treated is psoriasis.

The contents of the specification of Japanese Patent Application No. 2000-117791, the application on the basis of which the present application claims priority are to be incorporated in their entirety by reference.

PREFERRED MODE FOR CARRYING OUT
THE INVENTION

Detailed modes and methods with respect to vitamin D derivatives represented by Formula (1) and pharmaceutical compositions including thereof in accordance with the present invention are described in further detail below.

As used herein, "alkyl" means, in general, straight-chained or brunched $C_{1-15}$ alkyl; examples thereof include methyl, ethyl, n-propyl, i-propyl, n-butyl, s-butyl, i-butyl and t-butyl, and further include pentyl, hexyl, heptyl, octyl, nonyl, decanyl, etc. The number of carbon atoms is preferably 1 to 8, more preferably 1 to 4. As the alkyl, methyl or ethyl is preferred and methyl is more preferred.

Examples of a "protecting group" include acyl, substituted silyl and substituted alkyl, with acyl and substituted silyl being preferred.

"Acyl" means substituted carbonyl and the substituent of carbonyl means hydrogen, optionally substituted lower alkyl, optionally substituted aryl, optionally substituted lower alkyloxy, optionally substituted aryloxy, optionally substituted aralkyloxy and the like. The acyl is preferably formyl, lower alkylcarbonyl, optionally substituted phenylcarbonyl, lower alkyloxycarbonyl, optionally substituted phenylalkyloxycarbonyl etc., more preferably, formyl, acetyl, propionyl, butyryl, pivaloyl, benzoyl, methoxycarbonyl, ethoxycarbonyl, t-butoxycarbonyl, benzyloxycarbonyl, etc. As used herein, lower alkyl, lower alkyloxy, lower alkylcarbonyl and lower alkyloxycarbony mean $C_{1-6}$ alkyl, $C_{1-6}$ alkyloxy, $C_{1-6}$ alkylcarbonyl and $C_{1-6}$ alkyloxycarbonyl, respectively, unless otherwise defined.

"Substituted silyl" means lower alkyl, which may have at least one substituent, or silyl, which is substituted with optionally substituted aryl; preferably substituted silyl means tri-substituted silyl. Preferred examples of the substituted silyl include trimethylsilyl, triethylsilyl, triisopropylsilyl, t-butyldiphenylsilyl, t-butyldimethylsilyl and the like.

In general, "aryl" means $C_{6-20}$ aryl, preferably $C_{6-14}$ aryl.

"Substituted alkyl" means alkyl substituted with at least one substituent; preferred examples of the substituent include optionally substituted alkyloxy and optionally substituted aryl, in particular, optionally substituted lower alkyloxy. Examples of the substituted alkyl which is substituted with optionally substituted alkyloxy such as alkyloxy include methoxymethyl, 2-methoxyethoxymethyl and tetrahydropyran-2-yl. Examples of the substituent include halogen, cyano, nitro, amino, hydroxy, lower alkyl, lower alkyloxy, lower acyloxy, sulfonyl and the like.

Non-limiting examples of the vitamin D derivatives of Formula (1) of the present invention are shown in Tables 1–17.

$R_1$ is hydrogen in Table 1 and $R_1$ is the following Formula (2) in Tables 2–17.

TABLE 1

| Compound No. | X | R2 | R3 | R4 | R5 | R6 | R1 |
|---|---|---|---|---|---|---|---|
| 1 | O | H | H | H | OH | H | H |
| 2 | O | CH₃ | H | H | OH | H | H |
| 3 | O | H | = | | OH | H | H |
| 4 | O | CH₃ | = | | OH | H | H |

TABLE 2

| Compound No. | X | R2 | R3 | R4 | R5 | R6 | A | (Steric configuration) | m | n | R7 | R8 |
|---|---|---|---|---|---|---|---|---|---|---|---|---|
| 5 | O | H | H | H | OH | H | CH₂ | | 0 | 0 | OH | H |
| 6 | O | H | H | H | OH | H | CH₂ | | 1 | 0 | OH | H |
| 7 | O | H | H | H | OH | H | CH₂ | | 2 | 0 | OH | H |
| 8 | O | H | H | H | OH | H | CH₂ | | 3 | 0 | OH | H |
| 9 | O | H | H | H | OH | H | CH₂ | | 4 | 0 | OH | H |
| 10 | O | H | H | H | OH | H | CH₂ | | 0 | 1 | OH | H |
| 11 | O | H | H | H | OH | H | CH₂ | | 1 | 1 | OH | H |
| 12 | O | H | H | H | OH | H | CH₂ | | 2 | 1 | OH | H |
| 13 | O | H | H | H | OH | H | CH₂ | | 3 | 1 | OH | H |
| 14 | O | H | H | H | OH | H | CH₂ | | 4 | 1 | OH | H |
| 15 | O | H | H | H | OH | H | CH₂ | | 0 | 2 | OH | H |
| 16 | O | H | H | H | OH | H | CH₂ | | 1 | 2 | OH | H |
| 17 | O | H | H | H | OH | H | CH₂ | | 2 | 2 | OH | H |
| 18 | O | H | H | H | OH | H | CH₂ | | 3 | 2 | OH | H |
| 19 | O | H | H | H | OH | H | CH₂ | | 4 | 2 | OH | H |
| 20 | O | H | H | H | OH | H | CH(OH) | R | 1 | 0 | H | H |
| 21 | O | H | H | H | OH | H | CH(OH) | S | 1 | 0 | H | H |
| 22 | O | H | H | H | OH | H | CH(OH) | R | 1 | 1 | H | H |
| 23 | O | H | H | H | OH | H | CH(OH) | S | 1 | 1 | H | H |
| 24 | O | H | H | H | OH | H | CH(OH) | R | 2 | 0 | H | H |
| 25 | O | H | H | H | OH | H | CH(OH) | S | 2 | 0 | H | H |
| 26 | O | H | H | H | OH | H | CH(OH) | R | 2 | 1 | H | H |
| 27 | O | H | H | H | OH | H | CH(OH) | S | 2 | 1 | H | H |

TABLE 3

| Compound No. | X | R2 | R3 | R4 | R5 | R6 | A | (Steric configuration) | m | n | R7 | R8 |
|---|---|---|---|---|---|---|---|---|---|---|---|---|
| 28 | O | H | H | H | OH | H | CH(OH) | R | 3 | 0 | H | H |
| 29 | O | H | H | H | OH | H | CH(OH) | S | 3 | 0 | H | H |
| 30 | O | H | H | H | OH | H | CH(OH) | R | 3 | 1 | H | H |
| 31 | O | H | H | H | OH | H | CH(OH) | S | 3 | 1 | H | H |
| 32 | O | H | H | H | OH | H | C=O |  | 1 | 0 | H | H |
| 33 | O | H | H | H | OH | H | C=O |  | 1 | 0 | OH | H |
| 34 | O | H | H | H | OH | H | CH=CH | E | 1 | 0 | OH | H |
| 35 | O | H | H | H | OH | H | CH=CH | Z | 1 | 0 | OH | H |
| 36 | O | H | H | H | OH | H | CH=CH | E | 2 | 0 | OH | H |
| 37 | O | H | H | H | OH | H | CH=CH | Z | 2 | 0 | OH | H |
| 38 | O | H | H | H | OH | H | CH=CH | E | 3 | 0 | OH | H |
| 39 | O | H | H | H | OH | H | CH=CH | Z | 3 | 0 | OH | H |
| 40 | O | H | H | H | OH | H | CH=CH | E | 1 | 1 | OH | H |
| 41 | O | H | H | H | OH | H | CH=CH | Z | 1 | 1 | OH | H |
| 42 | O | H | H | H | OH | H | CH=CH | E | 2 | 1 | OH | H |
| 43 | O | H | H | H | OH | H | CH=CH | Z | 2 | 1 | OH | H |
| 44 | O | H | H | H | OH | H | CH=CH | E | 3 | 1 | OH | H |
| 45 | O | H | H | H | OH | H | CH=CH | Z | 3 | 1 | OH | H |
| 46 | O | H | H | H | OH | H | C≡C |  | 1 | 0 | OH | H |
| 47 | O | H | H | H | OH | H | C≡C |  | 2 | 0 | OH | H |
| 48 | O | H | H | H | OH | H | C≡C |  | 3 | 0 | OH | H |
| 49 | O | H | H | H | OH | H | C≡C |  | 1 | 1 | OH | H |
| 50 | O | H | H | H | OH | H | C≡C |  | 2 | 1 | OH | H |
| 51 | O | H | H | H | OH | H | C≡C |  | 3 | 1 | OH | H |

TABLE 4

| Compound No. | X | R2 | R3 | R4 | R5 | R6 | A | (Steric configuration) | m | n | R7 | R8 |
|---|---|---|---|---|---|---|---|---|---|---|---|---|
| 52 | O | $CH_3$ | H | H | OH | H | $CH_2$ |  | 0 | 0 | OH | H |
| 53 | O | $CH_3$ | H | H | OH | H | $CH_2$ |  | 1 | 0 | OH | H |
| 54 | O | $CH_3$ | H | H | OH | H | $CH_2$ |  | 2 | 0 | OH | H |
| 55 | O | $CH_3$ | H | H | OH | H | $CH_2$ |  | 3 | 0 | OH | H |
| 56 | O | $CH_3$ | H | H | OH | H | $CH_2$ |  | 4 | 0 | OH | H |
| 57 | O | $CH_3$ | H | H | OH | H | $CH_2$ |  | 0 | 1 | OH | H |
| 58 | O | $CH_3$ | H | H | OH | H | $CH_2$ |  | 1 | 1 | OH | H |
| 59 | O | $CH_3$ | H | H | OH | H | $CH_2$ |  | 2 | 1 | OH | H |
| 60 | O | $CH_3$ | H | H | OH | H | $CH_2$ |  | 3 | 1 | OH | H |
| 61 | O | $CH_3$ | H | H | OH | H | $CH_2$ |  | 4 | 1 | OH | H |
| 62 | O | $CH_3$ | H | H | OH | H | $CH_2$ |  | 0 | 2 | OH | H |
| 63 | O | $CH_3$ | H | H | OH | H | $CH_2$ |  | 1 | 2 | OH | H |
| 64 | O | $CH_3$ | H | H | OH | H | $CH_2$ |  | 2 | 2 | OH | H |
| 65 | O | $CH_3$ | H | H | OH | H | $CH_2$ |  | 3 | 2 | OH | H |
| 66 | O | $CH_3$ | H | H | OH | H | $CH_2$ |  | 4 | 2 | OH | H |
| 67 | O | $CH_3$ | H | H | OH | H | CH(OH) | R | 1 | 0 | H | H |
| 68 | O | $CH_3$ | H | H | OH | H | CH(OH) | S | 1 | 0 | H | H |
| 69 | O | $CH_3$ | H | H | OH | H | CH(OH) | R | 1 | 1 | H | H |
| 70 | O | $CH_3$ | H | H | OH | H | CH(OH) | S | 1 | 1 | H | H |
| 71 | O | $CH_3$ | H | H | OH | H | CH(OH) | R | 2 | 0 | H | H |
| 72 | O | $CH_3$ | H | H | OH | H | CH(OH) | S | 2 | 0 | H | H |
| 73 | O | $CH_3$ | H | H | OH | H | CH(OH) | R | 2 | 1 | H | H |
| 74 | O | $CH_3$ | H | H | OH | H | CH(OH) | S | 2 | 1 | H | H |
| 75 | O | $CH_3$ | H | H | OH | H | CH(OH) | R | 3 | 0 | H | H |

TABLE 5

| Compound No. | X | R2 | R3 | R4 | R5 | R6 | A | (Steric configuration) | m | n | R7 | R8 |
|---|---|---|---|---|---|---|---|---|---|---|---|---|
| 76 | O | $CH_3$ | H | H | OH | H | CH(OH) | S | 3 | 0 | H | H |
| 77 | O | $CH_3$ | H | H | OH | H | CH(OH) | R | 3 | 1 | H | H |
| 78 | O | $CH_3$ | H | H | OH | H | CH(OH) | S | 3 | 1 | H | H |
| 79 | O | $CH_3$ | H | H | OH | H | C=O |  | 1 | 0 | H | H |
| 80 | O | $CH_3$ | H | H | OH | H | C=O |  | 1 | 0 | OH | H |
| 81 | O | $CH_3$ | H | H | OH | H | CH=CH | E | 1 | 0 | OH | H |
| 82 | O | $CH_3$ | H | H | OH | H | CH=CH | Z | 1 | 0 | OH | H |
| 83 | O | $CH_3$ | H | H | OH | H | CH=CH | E | 2 | 0 | OH | H |
| 84 | O | $CH_3$ | H | H | OH | H | CH=CH | Z | 2 | 0 | OH | H |
| 85 | O | $CH_3$ | H | H | OH | H | CH=CH | E | 3 | 0 | OH | H |
| 86 | O | $CH_3$ | H | H | OH | H | CH=CH | Z | 3 | 0 | OH | H |

TABLE 5-continued

| Compound No. | X | R2 | R3 | R4 | R5 | R6 | A | (Steric configuration) | m | n | R7 | R8 |
|---|---|---|---|---|---|---|---|---|---|---|---|---|
| 87 | O | $CH_3$ | H | H | OH | H | CH=CH | E | 1 | 1 | OH | H |
| 88 | O | $CH_3$ | H | H | OH | H | CH=CH | Z | 1 | 1 | OH | H |
| 89 | O | $CH_3$ | H | H | OH | H | CH=CH | E | 2 | 1 | OH | H |
| 90 | O | $CH_3$ | H | H | OH | H | CH=CH | Z | 2 | 1 | OH | H |
| 91 | O | $CH_3$ | H | H | OH | H | CH=CH | E | 3 | 1 | OH | H |
| 92 | O | $CH_3$ | H | H | OH | H | CH=CH | Z | 3 | 1 | OH | H |
| 93 | O | $CH_3$ | H | H | OH | H | C≡C |  | 1 | 0 | OH | H |
| 94 | O | $CH_3$ | H | H | OH | H | C≡C |  | 2 | 0 | OH | H |
| 95 | O | $CH_3$ | H | H | OH | H | C≡C |  | 3 | 0 | OH | H |
| 96 | O | $CH_3$ | H | H | OH | H | C≡C |  | 1 | 1 | OH | H |
| 97 | O | $CH_3$ | H | H | OH | H | C≡C |  | 2 | 1 | OH | H |
| 98 | O | $CH_3$ | H | H | OH | H | C≡C |  | 3 | 1 | OH | H |
| 99 | S | H | H | H | OH | H | $CH_2$ |  | 0 | 0 | OH | H |

TABLE 6

| Compound No. | X | R2 | R3 | R4 | R5 | R6 | A | (Steric configuration) | m | n | R7 | R8 |
|---|---|---|---|---|---|---|---|---|---|---|---|---|
| 100 | S | H | H | H | OH | H | $CH_2$ |  | 1 | 0 | OH | H |
| 101 | S | H | H | H | OH | H | $CH_2$ |  | 2 | 0 | OH | H |
| 102 | S | H | H | H | OH | H | $CH_2$ |  | 3 | 0 | OH | H |
| 103 | S | H | H | H | OH | H | $CH_2$ |  | 4 | 0 | OH | H |
| 104 | S | H | H | H | OH | H | $CH_2$ |  | 0 | 1 | OH | H |
| 105 | S | H | H | H | OH | H | $CH_2$ |  | 1 | 1 | OH | H |
| 106 | S | H | H | H | OH | H | $CH_2$ |  | 2 | 1 | OH | H |
| 107 | S | H | H | H | OH | H | $CH_2$ |  | 3 | 1 | OH | H |
| 108 | S | H | H | H | OH | H | $CH_2$ |  | 4 | 1 | OH | H |
| 109 | S | H | H | H | OH | H | $CH_2$ |  | 0 | 2 | OH | H |
| 110 | S | H | H | H | OH | H | $CH_2$ |  | 1 | 2 | OH | H |
| 111 | S | H | H | H | OH | H | $CH_2$ |  | 2 | 2 | OH | H |
| 112 | S | H | H | H | OH | H | $CH_2$ |  | 3 | 2 | OH | H |
| 113 | S | H | H | H | OH | H | $CH_2$ |  | 4 | 2 | OH | H |
| 114 | S | H | H | H | OH | H | CH(OH) | R | 1 | 0 | H | H |
| 115 | S | H | H | H | OH | H | CH(OH) | S | 1 | 0 | H | H |
| 116 | S | H | H | H | OH | H | CH(OH) | R | 1 | 1 | H | H |
| 117 | S | H | H | H | OH | H | CH(OH) | S | 1 | 1 | H | H |
| 118 | S | H | H | H | OH | H | CH(OH) | R | 2 | 0 | H | H |
| 119 | S | H | H | H | OH | H | CH(OH) | S | 2 | 0 | H | H |
| 120 | S | H | H | H | OH | H | CH(OH) | R | 2 | 1 | H | H |
| 121 | S | H | H | H | OH | H | CH(OH) | S | 2 | 1 | H | H |
| 122 | S | H | H | H | OH | H | CH(OH) | R | 3 | 0 | H | H |
| 123 | S | H | H | H | OH | H | CH(OH) | S | 3 | 0 | H | H |

TABLE 7

| Compound No. | X | R2 | R3 | R4 | R5 | R6 | A | (Steric configuration) | m | n | R7 | R8 |
|---|---|---|---|---|---|---|---|---|---|---|---|---|
| 124 | S | H | H | H | OH | H | CH(OH) | R | 3 | 1 | H | H |
| 125 | S | H | H | H | OH | H | CH(OH) | S | 3 | 1 | H | H |
| 126 | S | H | H | H | OH | H | C=O |  | 1 | 0 | H | H |
| 127 | S | H | H | H | OH | H | C=O |  | 1 | 0 | OH | H |
| 128 | S | H | H | H | OH | H | CH=CH | E | 1 | 0 | OH | H |
| 129 | S | H | H | H | OH | H | CH=CH | Z | 1 | 0 | OH | H |
| 130 | S | H | H | H | OH | H | CH=CH | E | 2 | 0 | OH | H |
| 131 | S | H | H | H | OH | H | CH=CH | Z | 2 | 0 | OH | H |
| 132 | S | H | H | H | OH | H | CH=CH | E | 3 | 0 | OH | H |
| 133 | S | H | H | H | OH | H | CH=CH | Z | 3 | 0 | OH | H |
| 134 | S | H | H | H | OH | H | CH=CH | E | 1 | 1 | OH | H |
| 135 | S | H | H | H | OH | H | CH=CH | Z | 1 | 1 | OH | H |
| 136 | S | H | H | H | OH | H | CH=CH | E | 2 | 1 | OH | H |
| 137 | S | H | H | H | OH | H | CH=CH | Z | 2 | 1 | OH | H |
| 138 | S | H | H | H | OH | H | CH=CH | E | 3 | 1 | OH | H |
| 139 | S | H | H | H | OH | H | CH=CH | Z | 3 | 1 | OH | H |
| 140 | S | H | H | H | OH | H | C≡C |  | 1 | 0 | OH | H |
| 141 | S | H | H | H | OH | H | C≡C |  | 2 | 0 | OH | H |
| 142 | S | H | H | H | OH | H | C≡C |  | 3 | 0 | OH | H |
| 143 | S | H | H | H | OH | H | C≡C |  | 1 | 1 | OH | H |
| 144 | S | H | H | H | OH | H | C≡C |  | 2 | 1 | OH | H |
| 145 | S | H | H | H | OH | H | C≡C |  | 3 | 1 | OH | H |

TABLE 7-continued

| Compound No. | X | R2 | R3 | R4 | R5 | R6 | A | (Steric configuration) | m | n | R7 | R8 |
|---|---|---|---|---|---|---|---|---|---|---|---|---|
| 146 | S | $CH_3$ | H | H | OH | H | $CH_2$ | | 0 | 0 | OH | H |
| 147 | S | $CH_3$ | H | H | OH | H | $CH_2$ | | 1 | 0 | OH | H |

TABLE 8

| Compound No. | X | R2 | R3 | R4 | R5 | R6 | A | (Steric configuration) | m | n | R7 | R8 |
|---|---|---|---|---|---|---|---|---|---|---|---|---|
| 148 | S | $CH_3$ | H | H | OH | H | $CH_2$ | | 2 | 0 | OH | H |
| 149 | S | $CH_3$ | H | H | OH | H | $CH_2$ | | 3 | 0 | OH | H |
| 150 | S | $CH_3$ | H | H | OH | H | $CH_2$ | | 4 | 0 | OH | H |
| 151 | S | $CH_3$ | H | H | OH | H | $CH_2$ | | 0 | 1 | OH | H |
| 152 | S | $CH_3$ | H | H | OH | H | $CH_2$ | | 1 | 1 | OH | H |
| 153 | S | $CH_3$ | H | H | OH | H | $CH_2$ | | 2 | 1 | OH | H |
| 154 | S | $CH_3$ | H | H | OH | H | $CH_2$ | | 3 | 1 | OH | H |
| 155 | S | $CH_3$ | H | H | OH | H | $CH_2$ | | 4 | 1 | OH | H |
| 156 | S | $CH_3$ | H | H | OH | H | $CH_2$ | | 0 | 2 | OH | H |
| 157 | S | $CH_3$ | H | H | OH | H | $CH_2$ | | 1 | 2 | OH | H |
| 158 | S | $CH_3$ | H | H | OH | H | $CH_2$ | | 2 | 2 | OH | H |
| 159 | S | $CH_3$ | H | H | OH | H | $CH_2$ | | 3 | 2 | OH | H |
| 160 | S | $CH_3$ | H | H | OH | H | $CH_2$ | | 4 | 2 | OH | H |
| 161 | S | $CH_3$ | H | H | OH | H | CH(OH) | R | 1 | 0 | H | H |
| 162 | S | $CH_3$ | H | H | OH | H | CH(OH) | S | 1 | 0 | H | H |
| 163 | S | $CH_3$ | H | H | OH | H | CH(OH) | R | 1 | 1 | H | H |
| 164 | S | $CH_3$ | H | H | OH | H | CH(OH) | S | 1 | 1 | H | H |
| 165 | S | $CH_3$ | H | H | OH | H | CH(OH) | R | 2 | 0 | H | H |
| 166 | S | $CH_3$ | H | H | OH | H | CH(OH) | S | 2 | 0 | H | H |
| 167 | S | $CH_3$ | H | H | OH | H | CH(OH) | R | 2 | 1 | H | H |
| 168 | S | $CH_3$ | H | H | OH | H | CH(OH) | S | 2 | 1 | H | H |
| 169 | S | $CH_3$ | H | H | OH | H | CH(OH) | R | 3 | 0 | H | H |
| 170 | S | $CH_3$ | H | H | OH | H | CH(OH) | S | 3 | 0 | H | H |
| 171 | S | $CH_3$ | H | H | OH | H | CH(OH) | R | 3 | 1 | H | H |

TABLE 9

| Compound No. | X | R2 | R3 | R4 | R5 | R6 | A | (Steric configuration) | m | n | R7 | R8 |
|---|---|---|---|---|---|---|---|---|---|---|---|---|
| 172 | S | $CH_3$ | H | H | OH | H | CH(OH) | S | 3 | 1 | H | H |
| 173 | S | $CH_3$ | H | H | OH | H | C=O | | 1 | 0 | H | H |
| 174 | S | $CH_3$ | H | H | OH | H | C=O | | 1 | 0 | OH | H |
| 175 | S | $CH_3$ | H | H | OH | H | CH=CH | E | 1 | 0 | OH | H |
| 176 | S | $CH_3$ | H | H | OH | H | CH=CH | Z | 1 | 0 | OH | H |
| 177 | S | $CH_3$ | H | H | OH | H | CH=CH | E | 2 | 0 | OH | H |
| 178 | S | $CH_3$ | H | H | OH | H | CH=CH | Z | 2 | 0 | OH | H |
| 179 | S | $CH_3$ | H | H | OH | H | CH=CH | E | 3 | 0 | OH | H |
| 180 | S | $CH_3$ | H | H | OH | H | CH=CH | Z | 3 | 0 | OH | H |
| 181 | S | $CH_3$ | H | H | OH | H | CH=CH | E | 1 | 1 | OH | H |
| 182 | S | $CH_3$ | H | H | OH | H | CH=CH | Z | 1 | 1 | OH | H |
| 183 | S | $CH_3$ | H | H | OH | H | CH=CH | E | 2 | 1 | OH | H |
| 184 | S | $CH_3$ | H | H | OH | H | CH=CH | Z | 2 | 1 | OH | H |
| 185 | S | $CH_3$ | H | H | OH | H | CH=CH | E | 3 | 1 | OH | H |
| 186 | S | $CH_3$ | H | H | OH | H | CH=CH | Z | 3 | 1 | OH | H |
| 187 | S | $CH_3$ | H | H | OH | H | C≡C | | 1 | 0 | OH | H |
| 188 | S | $CH_3$ | H | H | OH | H | C≡C | | 2 | 0 | OH | H |
| 189 | S | $CH_3$ | H | H | OH | H | C≡C | | 3 | 0 | OH | H |
| 190 | S | $CH_3$ | H | H | OH | H | C≡C | | 1 | 1 | OH | H |
| 191 | S | $CH_3$ | H | H | OH | H | C≡C | | 2 | 1 | OH | H |
| 192 | S | $CH_3$ | H | H | OH | H | C≡C | | 3 | 1 | OH | H |
| 193 | O | H | = | | OH | H | $CH_2$ | | 0 | 0 | OH | H |
| 194 | O | H | = | | OH | H | $CH_2$ | | 1 | 0 | OH | H |
| 195 | O | H | = | | OH | H | $CH_2$ | | 2 | 0 | OH | H |

TABLE 10

| Compound No. | X | R2 | R3 | R4 | R5 | R6 | A | (Steric configuration) | m | n | R7 | R8 |
|---|---|---|---|---|---|---|---|---|---|---|---|---|
| 196 | O | H | = | | OH | H | $CH_2$ | | 3 | 0 | OH | H |
| 197 | O | H | = | | OH | H | $CH_2$ | | 4 | 0 | OH | H |
| 198 | O | H | = | | OH | H | $CH_2$ | | 0 | 1 | OH | H |

TABLE 10-continued

| Compound No. | X | R2 | R3 | R4 | R5 | R6 | A | (Steric configuration) | m | n | R7 | R8 |
|---|---|---|---|---|---|---|---|---|---|---|---|---|
| 199 | O | H | = | | OH | H | $CH_2$ | | 1 | 1 | OH | H |
| 200 | O | H | = | | OH | H | $CH_2$ | | 2 | 1 | OH | H |
| 201 | O | H | = | | OH | H | $CH_2$ | | 3 | 1 | OH | H |
| 202 | O | H | = | | OH | H | $CH_2$ | | 4 | 1 | OH | H |
| 203 | O | H | = | | OH | H | $CH_2$ | | 0 | 2 | OH | H |
| 204 | O | H | = | | OH | H | $CH_2$ | | 1 | 2 | OH | H |
| 205 | O | H | = | | OH | H | $CH_2$ | | 2 | 2 | OH | H |
| 206 | O | H | = | | OH | H | $CH_2$ | | 3 | 2 | OH | H |
| 207 | O | H | = | | OH | H | $CH_2$ | | 4 | 2 | OH | H |
| 208 | O | H | = | | OH | H | CH(OH) | R | 1 | 0 | H | H |
| 209 | O | H | = | | OH | H | CH(OH) | S | 1 | 0 | H | H |
| 210 | O | H | = | | OH | H | CH(OH) | R | 1 | 1 | H | H |
| 211 | O | H | = | | OH | H | CH(OH) | S | 1 | 1 | H | H |
| 212 | O | H | = | | OH | H | CH(OH) | R | 2 | 0 | H | H |
| 213 | O | H | = | | OH | H | CH(OH) | S | 2 | 0 | H | H |
| 214 | O | H | = | | OH | H | CH(OH) | R | 2 | 1 | H | H |
| 215 | O | H | = | | OH | H | CH(OH) | S | 2 | 1 | H | H |
| 216 | O | H | = | | OH | H | CH(OH) | R | 3 | 0 | H | H |
| 217 | O | H | = | | OH | H | CH(OH) | S | 3 | 0 | H | H |
| 218 | O | H | = | | OH | H | CH(OH) | R | 3 | 1 | H | H |
| 219 | O | H | = | | OH | H | CH(OH) | S | 3 | 1 | H | H |

TABLE 11

| Compound No. | X | R2 | R3 | R4 | R5 | R6 | A | (Steric configuration) | m | n | R7 | R8 |
|---|---|---|---|---|---|---|---|---|---|---|---|---|
| 220 | O | H | = | | OH | H | C=O | | 1 | 0 | H | H |
| 221 | O | H | = | | OH | H | C=O | | 1 | 0 | OH | H |
| 222 | O | H | = | | OH | H | CH=CH | E | 1 | 0 | OH | H |
| 223 | O | H | = | | OH | H | CH=CH | Z | 1 | 0 | OH | H |
| 224 | O | H | = | | OH | H | CH=CH | E | 2 | 0 | OH | H |
| 225 | O | H | = | | OH | H | CH=CH | Z | 2 | 0 | OH | H |
| 226 | O | H | = | | OH | H | CH=CH | E | 3 | 0 | OH | H |
| 227 | O | H | = | | OH | H | CH=CH | Z | 3 | 0 | OH | H |
| 228 | O | H | = | | OH | H | CH=CH | E | 1 | 1 | OH | H |
| 229 | O | H | = | | OH | H | CH=CH | Z | 1 | 1 | OH | H |
| 230 | O | H | = | | OH | H | CH=CH | E | 2 | 1 | OH | H |
| 231 | O | H | = | | OH | H | CH=CH | Z | 2 | 1 | OH | H |
| 232 | O | H | = | | OH | H | CH=CH | E | 3 | 1 | OH | H |
| 233 | O | H | = | | OH | H | CH=CH | Z | 3 | 1 | OH | H |
| 234 | O | H | = | | OH | H | C≡C | | 1 | 0 | OH | H |
| 235 | O | H | = | | OH | H | C≡C | | 2 | 0 | OH | H |
| 235 | O | H | = | | OH | H | C≡C | | 3 | 0 | OH | H |
| 237 | O | H | = | | OH | H | C≡C | | 1 | 1 | OH | H |
| 238 | O | H | = | | OH | H | C≡C | | 2 | 1 | OH | H |
| 239 | O | H | = | | OH | H | C≡C | | 3 | 1 | OH | H |
| 240 | O | $CH_3$ | = | | OH | H | $CH_2$ | | 0 | 0 | OH | H |
| 241 | O | $CH_3$ | = | | OH | H | $CH_2$ | | 1 | 0 | OH | H |
| 242 | O | $CH_3$ | = | | OH | H | $CH_2$ | | 2 | 0 | OH | H |
| 243 | O | $CH_3$ | = | | OH | H | $CH_2$ | | 3 | 0 | OH | H |

TABLE 12

| Compound No. | X | R2 | R3 | R4 | R5 | R6 | A | (Steric configuration) | m | n | R7 | R8 |
|---|---|---|---|---|---|---|---|---|---|---|---|---|
| 244 | O | $CH_3$ | = | | OH | H | $CH_2$ | | 4 | 0 | OH | H |
| 245 | O | $CH_3$ | = | | OH | H | $CH_2$ | | 0 | 1 | OH | H |
| 246 | O | $CH_3$ | = | | OH | H | $CH_2$ | | 1 | 1 | OH | H |
| 247 | O | $CH_3$ | = | | OH | H | $CH_2$ | | 2 | 1 | OH | H |
| 246 | O | $CH_3$ | = | | OH | H | $CH_2$ | | 3 | 1 | OH | H |
| 249 | O | $CH_3$ | = | | OH | H | $CH_2$ | | 4 | 1 | OH | H |
| 250 | O | $CH_3$ | = | | OH | H | $CH_2$ | | 0 | 2 | OH | H |
| 251 | O | $CH_3$ | = | | OH | H | $CH_2$ | | 1 | 2 | OH | H |
| 252 | O | $CH_3$ | = | | OH | H | $CH_2$ | | 2 | 2 | OH | H |
| 253 | O | $CH_3$ | = | | OH | H | $CH_2$ | | 3 | 2 | OH | H |
| 254 | O | $CH_3$ | = | | OH | H | $CH_2$ | | 4 | 2 | OH | H |
| 255 | O | $CH_3$ | = | | OH | H | CH(OH) | R | 1 | 0 | H | H |
| 256 | O | $CH_3$ | = | | OH | H | CH(OH) | S | 1 | 0 | H | H |
| 257 | O | $CH_3$ | = | | OH | H | CH(OH) | R | 1 | 1 | H | H |

TABLE 12-continued

| Compound No. | X | R2 | R3 | R4 | R5 | R6 | A | (Steric configuration) | m | n | R7 | R8 |
|---|---|---|---|---|---|---|---|---|---|---|---|---|
| 258 | O | $CH_3$ | = |  | OH | H | CH(OH) | S | 1 | 1 | H | H |
| 259 | O | $CH_3$ | = |  | OH | H | CH(OH) | R | 2 | 0 | H | H |
| 260 | O | $CH_3$ | = |  | OH | H | CH(OH) | S | 2 | 0 | H | H |
| 261 | O | $CH_3$ | = |  | OH | H | CH(OH) | R | 2 | 1 | H | H |
| 262 | O | $CH_3$ | = |  | OH | H | CH(OH) | S | 2 | 1 | H | H |
| 263 | O | $CH_3$ | = |  | OH | H | CH(OH) | R | 3 | 0 | H | H |
| 264 | O | $CH_3$ | = |  | OH | H | CH(OH) | S | 3 | 0 | H | H |
| 265 | O | $CH_3$ | = |  | OH | H | CH(OH) | R | 3 | 1 | H | H |
| 266 | O | $CH_3$ | = |  | OH | H | CH(OH) | S | 3 | 1 | H | H |
| 267 | O | $CH_3$ | = |  | OH | H | C=O |  | 1 | 0 | H | H |

TABLE 13

| Compound No. | X | R2 | R3 | R4 | R5 | R6 | A | (Steric configuration) | m | n | R7 | R8 |
|---|---|---|---|---|---|---|---|---|---|---|---|---|
| 268 | O | $CH_3$ | = |  | OH | H | C=O |  | 1 | 0 | OH | H |
| 269 | O | $CH_3$ | = |  | OH | H | CH=CH | E | 1 | 0 | OH | H |
| 270 | O | $CH_3$ | = |  | OH | H | CH=CH | Z | 1 | 0 | OH | H |
| 271 | O | $CH_3$ | = |  | OH | H | CH=CH | E | 2 | 0 | OH | H |
| 272 | O | $CH_3$ | = |  | OH | H | CH=CH | Z | 2 | 0 | OH | H |
| 273 | O | $CH_3$ | = |  | OH | H | CH=CH | E | 3 | 0 | OH | H |
| 274 | O | $CH_3$ | = |  | OH | H | CH=CH | Z | 3 | 0 | OH | H |
| 275 | O | $CH_3$ | = |  | OH | H | CH=CH | E | 1 | 1 | OH | H |
| 276 | O | $CH_3$ | = |  | OH | H | CH=CH | Z | 1 | 1 | OH | H |
| 277 | O | $CH_3$ | = |  | OH | H | CH=CH | E | 2 | 1 | OH | H |
| 278 | O | $CH_3$ | = |  | OH | H | CH=CH | Z | 2 | 1 | OH | H |
| 279 | O | $CH_3$ | = |  | OH | H | CH=CH | E | 3 | 1 | OH | H |
| 280 | O | $CH_3$ | = |  | OH | H | CH=CH | Z | 3 | 1 | OH | H |
| 281 | O | $CH_3$ | = |  | OH | H | C≡C |  | 1 | 0 | OH | H |
| 282 | O | $CH_3$ | = |  | OH | H | C≡C |  | 2 | 0 | OH | H |
| 283 | O | $CH_3$ | = |  | OH | H | C≡C |  | 3 | 0 | OH | H |
| 284 | O | $CH_3$ | = |  | OH | H | C≡C |  | 1 | 1 | OH | H |
| 285 | O | $CH_3$ | = |  | OH | H | C≡C |  | 2 | 1 | OH | H |
| 286 | O | $CH_3$ | = |  | OH | H | C≡C |  | 3 | 1 | OH | H |
| 287 | S | H | = |  | OH | H | $CH_2$ |  | 0 | 0 | OH | H |
| 288 | S | H | = |  | OH | H | $CH_2$ |  | 1 | 0 | OH | H |
| 289 | S | H | = |  | OH | H | $CH_2$ |  | 2 | 0 | OH | H |
| 290 | S | H | = |  | OH | H | $CH_2$ |  | 3 | 0 | OH | H |
| 291 | S | H | = |  | OH | H | $CH_2$ |  | 4 | 0 | OH | H |

TABLE 14

| Compound No. | X | R2 | R3 | R4 | R5 | R6 | A | (Steric configuration) | m | n | R7 | R8 |
|---|---|---|---|---|---|---|---|---|---|---|---|---|
| 292 | S | H | = |  | OH | H | $CH_2$ |  | 0 | 1 | OH | H |
| 293 | S | H | = |  | OH | H | $CH_2$ |  | 1 | 1 | OH | H |
| 294 | S | H | = |  | OH | H | $CH_2$ |  | 2 | 1 | OH | H |
| 295 | S | H | = |  | OH | H | $CH_2$ |  | 3 | 1 | OH | H |
| 296 | S | H | = |  | OH | H | $CH_2$ |  | 4 | 1 | OH | H |
| 297 | S | H | = |  | OH | H | $CH_2$ |  | 0 | 2 | OH | H |
| 298 | S | H | = |  | OH | H | $CH_2$ |  | 1 | 2 | OH | H |
| 299 | S | H | = |  | OH | H | $CH_2$ |  | 2 | 2 | OH | H |
| 300 | S | H | = |  | OH | H | $CH_2$ |  | 3 | 2 | OH | H |
| 301 | S | H | = |  | OH | H | $CH_2$ |  | 4 | 2 | OH | H |
| 302 | S | H | = |  | OH | H | CH(OH) | R | 1 | 0 | H | H |
| 303 | S | H | = |  | OH | H | CH(OH) | S | 1 | 0 | H | H |
| 304 | S | H | = |  | OH | H | CH(OH) | R | 1 | 1 | H | H |
| 305 | S | H | = |  | OH | H | CH(OH) | S | 1 | 1 | H | H |
| 306 | S | H | = |  | OH | H | CH(OH) | R | 2 | 0 | H | H |
| 307 | S | H | = |  | OH | H | CH(OH) | S | 2 | 0 | H | H |
| 308 | S | H | = |  | OH | H | CH(OH) | R | 2 | 1 | H | H |
| 309 | S | H | = |  | OH | H | CH(OH) | S | 2 | 1 | H | H |
| 310 | S | H | = |  | OH | H | CH(OH) | R | 3 | 0 | H | H |
| 311 | S | H | = |  | OH | H | CH(OH) | S | 3 | 0 | H | H |
| 312 | S | H | = |  | OH | H | CH(OH) | R | 3 | 1 | H | H |
| 313 | S | H | = |  | OH | H | CH(OH) | S | 3 | 1 | H | H |
| 314 | S | H | = |  | OH | H | C=O |  | 1 | 0 | H | H |
| 315 | S | H | = |  | OH | H | C=O |  | 1 | 0 | OH | H |

TABLE 15

| Compound No. | X | R2 | R3 R4 | R5 | R6 | A | (Steric configuration) | m | n | R7 | R8 |
|---|---|---|---|---|---|---|---|---|---|---|---|
| 316 | S | H | = | OH | H | CH=CH | E | 1 | 0 | OH | H |
| 317 | S | H | = | OH | H | CH=CH | Z | 1 | 0 | OH | H |
| 318 | S | H | = | OH | H | CH=CH | E | 2 | 0 | OH | H |
| 319 | S | H | = | OH | H | CH=CH | Z | 2 | 0 | OH | H |
| 320 | S | H | = | OH | H | CH=CH | E | 3 | 0 | OH | H |
| 321 | S | H | = | OH | H | CH=CH | Z | 3 | 0 | OH | H |
| 322 | S | H | = | OH | H | CH=CH | E | 1 | 1 | OH | H |
| 323 | S | H | = | OH | H | CH=CH | Z | 1 | 1 | OH | H |
| 324 | S | H | = | OH | H | CH=CH | E | 2 | 1 | OH | H |
| 325 | S | H | = | OH | H | CH=CH | Z | 2 | 1 | OH | H |
| 326 | S | H | = | OH | H | CH=CH | E | 3 | 1 | OH | H |
| 327 | S | H | = | OH | H | CH=CH | Z | 3 | 1 | OH | H |
| 328 | S | H | = | OH | H | C≡C | | 1 | 0 | OH | H |
| 329 | S | H | = | OH | H | C≡C | | 2 | 0 | OH | H |
| 330 | S | H | = | OH | H | C≡C | | 3 | 0 | OH | H |
| 331 | S | H | = | OH | H | C≡C | | 1 | 1 | OH | H |
| 332 | S | H | = | OH | H | C≡C | | 2 | 1 | OH | H |
| 333 | S | H | = | OH | H | C≡C | | 3 | 1 | OH | H |
| 334 | S | CH$_3$ | = | OH | H | CH$_2$ | | 0 | 0 | OH | H |
| 335 | S | CH$_3$ | = | OH | H | CH$_2$ | | 1 | 0 | OH | H |
| 336 | S | CH$_3$ | = | OH | H | CH$_2$ | | 2 | 0 | OH | H |
| 337 | S | CH$_3$ | = | OH | H | CH$_2$ | | 3 | 0 | OH | H |
| 338 | S | CH$_3$ | = | OH | H | CH$_2$ | | 4 | 0 | OH | H |
| 339 | S | CH$_3$ | = | OH | H | CH$_2$ | | 0 | 1 | OH | H |

TABLE 16

| Compound No. | X | R2 | R3 R4 | R5 | R6 | A | (Steric configuration) | m | n | R7 | R8 |
|---|---|---|---|---|---|---|---|---|---|---|---|
| 340 | S | CH$_3$ | = | OH | H | CH$_2$ | | 1 | 1 | OH | H |
| 341 | S | CH$_3$ | = | OH | H | CH$_2$ | | 2 | 1 | OH | H |
| 342 | S | CH$_3$ | = | OH | H | CH$_2$ | | 3 | 1 | OH | H |
| 343 | S | CH$_3$ | = | OH | H | CH$_2$ | | 4 | 1 | OH | H |
| 344 | S | CH$_3$ | = | OH | H | CH$_2$ | | 0 | 2 | OH | H |
| 345 | S | CH$_3$ | = | OH | H | CH$_2$ | | 1 | 2 | OH | H |
| 346 | S | CH$_3$ | = | OH | H | CH$_2$ | | 2 | 2 | OH | H |
| 347 | S | CH$_3$ | = | OH | H | CH$_2$ | | 3 | 2 | OH | H |
| 348 | S | CH$_3$ | = | OH | H | CH$_2$ | | 4 | 2 | OH | H |
| 349 | S | CH$_3$ | = | OH | H | CH(OH) | R | 1 | 0 | H | H |
| 350 | S | CH$_3$ | = | OH | H | CH(OH) | S | 1 | 0 | H | H |
| 351 | S | CH$_3$ | = | OH | H | CH(OH) | R | 1 | 1 | H | H |
| 352 | S | CH$_3$ | = | OH | H | CH(OH) | S | 1 | 1 | H | H |
| 353 | S | CH$_3$ | = | OH | H | CH(OH) | R | 2 | 0 | H | H |
| 354 | S | CH$_3$ | = | OH | H | CH(OH) | S | 2 | 0 | H | H |
| 355 | S | CH$_3$ | = | OH | H | CH(OH) | R | 2 | 1 | H | H |
| 356 | S | CH$_3$ | = | OH | H | CH(OH) | S | 2 | 1 | H | H |
| 357 | S | CH$_3$ | = | OH | H | CH(OH) | R | 3 | 0 | H | H |
| 358 | S | CH$_3$ | = | OH | H | CH(OH) | S | 3 | 0 | H | H |
| 359 | S | CH$_3$ | = | OH | H | CH(OH) | R | 3 | 1 | H | H |
| 360 | S | CH$_3$ | = | OH | H | CH(OH) | S | 3 | 1 | H | H |
| 361 | S | CH$_3$ | = | OH | H | C=O | | 1 | 0 | H | H |
| 362 | S | CH$_3$ | = | OH | H | C=O | | 1 | 0 | OH | H |
| 363 | S | CH$_3$ | = | OH | H | CH=CH | E | 1 | 0 | OH | H |

TABLE 17

| Compound No. | X | R2 | R3 R4 | R5 | R6 | A | (Steric configuration) | m | n | R7 | R8 |
|---|---|---|---|---|---|---|---|---|---|---|---|
| 364 | S | CH$_3$ | = | OH | H | CH=CH | Z | 1 | 0 | OH | H |
| 365 | S | CH$_3$ | = | OH | H | CH=CH | E | 2 | 0 | OH | H |
| 366 | S | CH$_3$ | = | OH | H | CH=CH | Z | 2 | 0 | OH | H |
| 367 | S | CH$_3$ | = | OH | H | CH=CH | E | 3 | 0 | OH | H |
| 368 | S | CH$_3$ | = | OH | H | CH=CH | Z | 3 | 0 | OH | H |
| 369 | S | CH$_3$ | = | OH | H | CH=CH | E | 1 | 1 | OH | H |
| 370 | S | CH$_3$ | = | OH | H | CH=CH | Z | 1 | 1 | OH | H |
| 371 | S | CH$_3$ | = | OH | H | CH=CH | E | 2 | 1 | OH | H |
| 372 | S | CH$_3$ | = | OH | H | CH=CH | Z | 2 | 1 | OH | H |
| 373 | S | CH$_3$ | = | OH | H | CH=CH | E | 3 | 1 | OH | H |
| 374 | S | CH$_3$ | = | OH | H | CH=CH | Z | 3 | 1 | OH | H |

TABLE 17-continued

| Compound No. | X | R2 | R3 | R4 | R5 | R6 | A | (Steric configuration) | m | n | R7 | R8 |
|---|---|---|---|---|---|---|---|---|---|---|---|---|
| 375 | S | CH₃ | = |   | OH | H | C≡C |   | 1 | 0 | OH | H |
| 376 | S | CH₃ | = |   | OH | H | C≡C |   | 2 | 0 | OH | H |
| 377 | S | CH₃ | = |   | OH | H | C≡C |   | 3 | 0 | OH | H |
| 378 | S | CH₃ | = |   | OH | H | C≡C |   | 1 | 1 | OH | H |
| 379 | S | CH₃ | = |   | OH | H | C≡C |   | 2 | 1 | OH | H |
| 380 | S | CH₃ | = |   | OH | H | C≡C |   | 3 | 1 | OH | H |

Although the vitamin D derivatives of Formula (1) of the present invention can be produced according to the following process, they can be synthesized by other processes known in the art and are therefore not limited to the following process.

I. Synthesis of Vitamin D Derivatives in which $R_3$ and $R_4$ Together Form a Double Bond in Formula (1)

I-1. Synthesis of Vitamin D Derivatives in which X is Oxygen in Formula (1)

Vitamin D derivatives in which X is oxygen, $R_2$ is hydrogen or methyl and $R_3$ and $R_4$ together form a double bond between the 16- and 17-positions in Formula (1) can be produced, for example, by the method shown in the following scheme using a compound of Formula (A) (described by E. Murayama, et al, Chem. Pharm. Bull., 34(10), 1986, JP No. 61-267550 A, etc.) as a starting material.

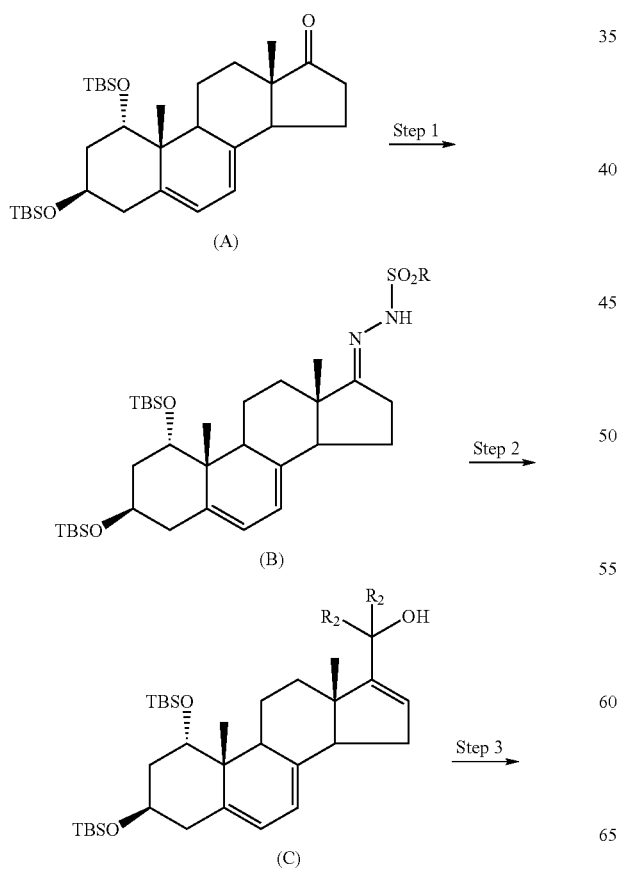

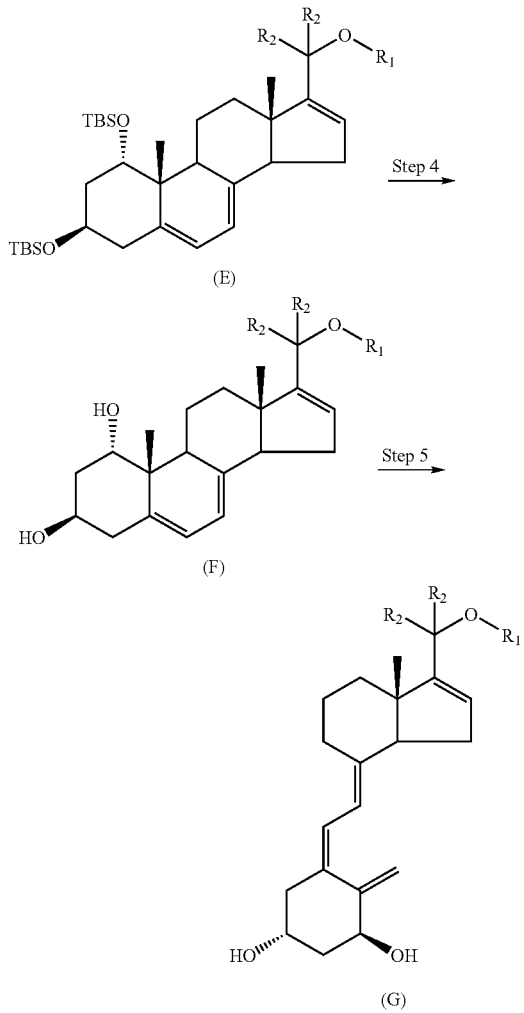

wherein
TBS is a t-butyldimethylsilyl group and each R is optionally substituted aryl or optionally substituted alkyl.

(Step 1) Formation of Hydrazone

In an appropriate solvent, Compound (A) is reacted with an arylsulfonyl or alkylsulfonyl hydrazide to synthesize Compound (B).

Examples of the arylsulfonyl or alkylsulfonyl hydrazide used for this reaction include benzenesulfonyl hydrazide, p-toluenesulfonyl hydrazide, m-toluenesulfonyl hydrazide, o-toluenesulfonyl hydrazide, 4-ethylbenzenesulfonyl hydrazide, 2-mesitylenesulfonyl hydrazide, 4-chlorobenzenesulfonyl hydrazide, 4-isopropylbenzenesulfonyl hydrazide, 2,4,6-triisopropylbenzenesulfonyl hydrazide, methanesulfonyl hydrazide, 2-methyl-2-propanesulfonyl hydrazide, 2-propanesulfonyl hydrazide, ethanesulfonyl hydrazide and the like, preferably benzenesulfonyl hydrazide, p-toluenesulfonyl hydrazide and 2,4,6-triisopropylbenzenesulfonyl hydrazide, and more preferably 2,4,6-triisopropylbenzenesulfonyl hydrazide.

Hydrocarbon-, ether-, halogen-, ester-, amide-, alcohol-, sulfoxide- and nitrile-based solvents can be used as the solvent used in this reaction. Examples of the solvent includes hexane, benzene, toluene, diethyl ether, tetrahydrofuran, 1,4-dioxane, 1,2-dimethoxyethane, t-butylmethyl ether, diisopropyl ether, dichloromethane, chloroform, 1,2-dichloroethane, chlorobenzene, ethyl acetate, methyl acetate, propyl acetate, N,N-dimethylformamide, N,N-dimethylacetamide, 1,3-dimethyl-2-imidazolidinone, 1,3-dimethyl-3,4,5,6-tetrahydro-2(1H)-pyrimidinone, methanol, ethanol, isopropanol, dimethylsulfoxide, acetonitrile, propionitrile and the like. Among them, toluene, diethyl ether, tetrahydrofuran, dichloromethane and ethyl acetate are preferred and tetrahydrofuran and ethyl acetate are more preferred.

The reaction temperature is not particularly limited unless the reaction can proceed; the reaction is preferably carried out in the range of 0 to 100° C. and more preferably at room temperature.

(Step 2) Alkylation

Compound (B) is reacted with a base in an appropriate solvent and then reacted with formaldehyde (or its equivalent such as 1,3,5-trioxane, paraformaldehyde, etc.) or acetone to synthesize Compound (C).

Examples of the base used in the above reaction include n-butyllithium, s-butyllithium, t-butyllithium, methyllithium, phenyllithium, methylmagnesium bromide, methylmagnesium chloride, methylmagnesium iodide, isopropylmagnesium bromide, diisopropylmagnesium, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride, potassium bis(trimethylsilyl)amide and the like. Among them, n-butyllithium, s-butyllithium, t-butyllithium, lithium diisopropylamide are preferred and n-butyllithium and s-butyllithium are more preferred.

In the above reaction, an appropriate metallic salt may be added after using the base. Examples of the metallic salt include cerium chloride, magnesium bromide, magnesium chloride, zinc chloride, titanium tetrachloride, chlorotitanium triisopropoxide, samarium chloride, indium chloride and the like, with cerium chloride being preferred.

Hydrocarbon- and ether-based solvents can be used as the solvent in the above reaction. Examples thereof include pentane, hexane, benzene, toluene, diethyl ether, t-butylmethyl ether, tetrahydrofuran, 1,2-dimethoxyethane, 1,4-dioxane, anisole and the like. Among them, hexane, diethyl ether and tetrahydrofuran are preferred and hexane and tetrahydrofuran are more preferred.

The above reaction may be carried out in the presence of an amide or amine compound. Examples of the amide or amine compound include 1,4-diazabicyclo[2,2,2]octane, N,N,N',N'-tetramethylethylenediamine, 1,3-dimethyl-2-imidazolidinone, 1,3-dimethyl-3,4,5,6-tetrahydro-2(1H)-pyrimidinone, N,N-dimethylformamide, N,N-dimethylacetamide, hexamethylphosphotriamide and the like. Among them, N,N,N',N'-tetramethylethylenediamine, 1,3-dimethyl-3,4,5,6-tetrahydro-2(1H)-pyrimidinone and hexamethylphosphotriamide are preferred and N,N,N',N'-tetramethylethylenediamine is more preferred.

Although the reaction temperature of using the base is not particularly limited unless the reaction can proceed, the reaction is preferably carried out in the range of −100° C. to 50° C. and more preferably in the range of −80° C. to 20° C.

In the above reaction, the reaction temperature using formaldehyde (or its equivalent such as 1,3,5-trioxane, paraformaldehyde, etc.) or acetone is not particularly limited unless the reaction can proceed; the reaction is preferably carried out in the range of −100° C. to 50° C. and more preferably in the range of −80° C. to 20° C.

Those compounds in which $R_2$ is hydrogen may also be synthesized by the following method.

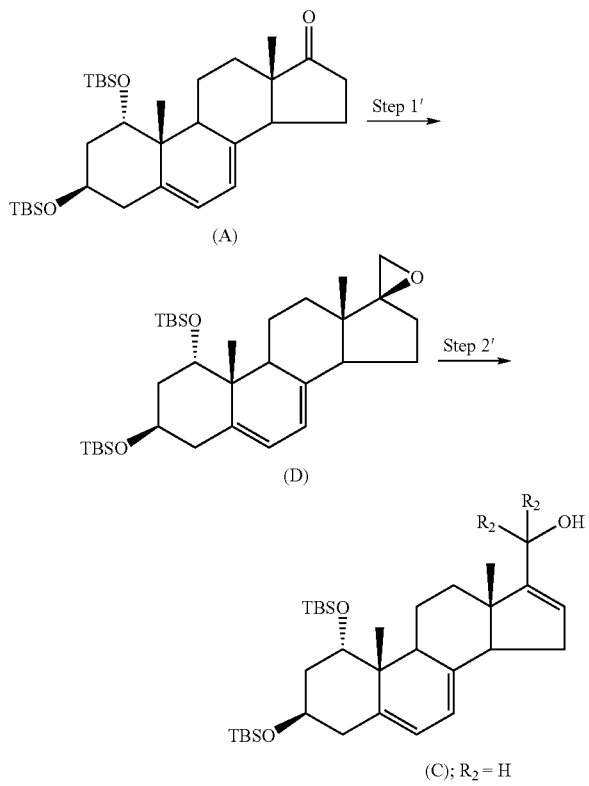

(Step 1') Epoxidation

In an appropriate solvent, Compound (A) is reacted with a trimethylsulfonium or trimethylsulfoxonium salt in the presence of a base to give Compound (D).

Examples of the trimethylsulfonium or trimethylsulfoxonium salt used in this reaction include trimethylsulfonium iodide, trimethylsulfonium bromide, trimethylsulfonium chloride, trimethylsulfonium methylsulfate, trimethylsulfonium tetrafluoroborate, trimethylsulfonium perchlorate, trimethylsulfoxonium iodide, trimethylsulfoxonium bromide, trimethylsulfoxonium chloride, trimethylsulfoxonium methylsulfate, trimethylsulfoxonium tetrafluoroborate, trimethylsulfoxonium perchlorate and the like, with trimethylsulfonium bromide and trimethylsulfoxonium iodide being preferred.

Examples of the base used in this reaction include n-butyllithium, s-butyllithium, t-butyllithium, methyllithium, phenyllithium, methylmagnesium bromide, methylmagnesium chloride, methylmagnesium iodide, isopropylmagnesium bromide, lithium diisopropylamide, lithium bis(triethylsilyl)amide, lithium 2,2,6,6-tetramethylpiperidide, lithium amide, sodium hydride, sodium bis(trimethylsilyl)amide, potassium hydride, potassium bis(trimethylsilyl)amide, sodium hydroxide, potassium hydroxide and the like. Among them, sodium hydride, potassium hydride, n-butyllithium, s-butyllithium, t-butyllithium, sodium hydroxide and potassium hydroxide are preferred and sodium hydride and potassium hydride are more preferred.

Hydrocarbon-, ether-, amide- and sulfoxide-based solvents can be used as the solvent in this reaction; examples thereof include pentane, hexane, benzene, toluene, diethyl ether, t-butylmethyl ether, tetrahydrofuran, 1,2-dimethoxyethane, 1,4-dioxane, anisol, diglyme, N,N-dimethylformamide, N,N-dimethylacetamide, 1,3-dimethyl-2-imidazolidinone, 1,3-dimethyl-3,4,5,6-tetrahydro-2(1H)-pyrimidinone, dimethylsulfoxide and the like, with dimethylsulfoxide being preferred. An ether-based solvent such as tetrahydrofuran can be added to the solvent, if desired.

The temperature of the above reaction is not particularly limited unless the reaction can proceed; the reaction is preferably carried out in the range of −20° C. to 20° C.

(Step 2') Ring Opening of the Epoxide

In an appropriate solvent, Compound (D) was reacted with an acid to synthesize Compound (C).

Examples of the acid used in this reaction include hydrochloric acid, sulfuric acid, acetic acid, phosphoric acid, aluminum trimethoxide, aluminum triethoxide, aluminum triisopropoxide, aluminum tri-t-butoxide, aluminum chloride, zinc chloride, tin(II) chloride, tin(IV) chloride, titanium tetrachloride, titanium tetramethoxide, titanium tetraethoxide, titanium tetraisopropoxide and the like. Among them, aluminum trimethoxide, aluminum triethoxide, aluminum triisopropoxide and aluminum tri-t-butoxide are preferred and aluminum triisopropoxide is more preferred.

Hydrocarbon-, ether-, halogen- and amide-based solvents can be used in this reaction; examples thereof include pentane, hexane, benzene, 1,2-dichlorobenzene, toluene, diethyl ether, tetrahydrofuran, 1,4-dioxane, t-butylmethyl ether, diglyme, 1,2-dimethoxyethane, 1,4-dioxane, anisole, dichloromethane, chloroform, carbon tetrachloride, 1,2-dichloromethane, N,N-dimethylformamide, N,N-dimethylacetamide, 1,3-dimethyl-2-imidazolidinone, 1,3-dimethyl-3,4,5,6-tetrahydro-2(1H)-pyrimidinone, dimethylsulfoxide and the like. Among them, benzene, 1,2-dichlorobenzene and toluene are preferred and 1,2-dichlorobenzene is more preferred.

The temperature of the above reaction is not particularly limited unless the reaction can proceed; the reaction is preferably carried out in the range of 0° C. to 200° C. and more preferably in the range of 80 to 180° C.

The above reaction may be carried out by using a base instead of an acid. Examples of the base include n-butyllithium, s-butyllithium, t-butyllithium, methyllithium, phenyllithium, methylmagnesium bromide, methylmagnesium chloride, methylmagnesium iodide, isopropylmagnesium bromide, lithium diethylamide, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride, potassium bis(trimethylsilyl)amide, diethylaluminum diisopropylamide, diethylaluminum 2,2,6,6-tetramethylpiperidide, sodium hydroxide, potassium hydroxide and the like. Among them, lithium diethylamide, diisopropyl magnesium, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride, potassium bis(trimethylsilyl)amide, diethylaluminum diisopropylamide, diethylaluminum 2,2,6,6-tetramethylpiperidide and the like are preferred and diethylamide is more preferred.

When a base is used, hydrocarbon-, ether-, halogen- and amide-based solvents can be used. Examples thereof include pentane, hexane, benzene, 1,2-dichlorobenzene, toluene, diethyl ether, tetrahydrofuran, 1,4-dioxane, t-butylmethyl ether, diglyme, 1,2-dimethoxyethane, 1,4-dioxane, anisole, dichloromethane, chloroform, carbon tetrachloride, 1,2-dichloromethane, N,N-dimethylformamide, N,N-dimethylacetamide, 1,3-dimethyl-2-imidazolidinone, 1,3-dimethyl-3,4,5,6-tetrahydro-2(1H)-pyrimidinone, dimethylsulfoxide and the like, with benzene, toluene, diethyl ether and tetrahydrofuran being preferred.

The reaction temperature when the base is used is not particularly limited unless the reaction can proceed; the reaction is preferably carried out in the range of −40° C. to 200° C. and more preferably in the range of 0 to 100° C.

(Step 3) Side Chain Introduction

For the introduction of a side chain, Compound (C) obtained from the above Steps (1) and (2), Steps (1') and (2'), etc. is reacted with an alkylation agent corresponding to the side chain in the presence of a base to give Compound (E).

An alkylation agent corresponding to the side chain $R_1$ of the vitamin D derivative of Formula (1) of the present invention is employed. That is, an alkylation agent of the following formula:

$R_{1a}$-Z (wherein Z is a leaving group such as halogen, mesyloxy, tosyloxy and trifluoromethanesulfonyloxy and $R_{1a}$ is a monovalent residual group of $R_1$) corresponding to $R_1$ of Formula (1).

Examples of $R_{1a}$-Z include 1-bromo-4-methyl-4-(triethylsilyloxy)pentane, 1-bromo-4-ethyl-4-(triethylsilyloxy)hexane, 1-bromo-5-triethylsilyloxy-5-methylhexane, 1-bromo-4-triethylsilyloxy-4-methyl-2-pentyne and the like.

Examples of the base include alkaline metal hydrides, alkaline metal alkoxides, metal dialkylamides, alkaline metals and the like; sodium hydride, potassium hydride, potassium t-butoxide, lithium diisopropylamide, lithium bis(trimethylsilyl)amide, methyllithium, n-butyllithium and ethylmagnesium bromide are preferred, and sodium hydride and potassium hydride are more preferred.

This reaction may be carried out in the presence of a crown ether. Examples of the crown ether include 15-crown-5, 18-crown-6, dibenzo-18-crown-6 and the like.

Hydrocarbon-, ether- and amide-based solvents and the like can be used as the solvent; specific examples thereof include benzene, toluene, diethyl ether, tetrahydrofuran, 1,2-dimethoxyethane, 1,4-dioxane, N,N-dimethylacetamide, N,N-dimethylformamide, 1,3-dimethyl-2-imidazolidinone, 1,3-dimethyl-3,4,5,6-tetrahydro-2(1H)-pyrimidinone and the like. Among them, tetrahydrofuran, 1,2-dimethoxyethane, N,N-dimethylformamide and 1,3-dimethyl-2-imidazolidinone are preferred and tetrahydrofuran is more preferred.

The reaction temperature depends on the substance; in general, the reaction is carried out in the range of −40° C. to the boiling or decomposition temperature of the solvent used in the reaction, preferably in the range of from 0 to 200° C. and more preferably from about room temperature to 120° C.

The side chain introduction is not limited to the above method and, for example, an epoxide such as isobutyleneoxide or 1,2-epoxy-2-ethylbutane may be used instead of an alkylhalide. Reaction using an epoxide can be carried out under similar conditions to those using an alkylhalide (JP No. 6-80626 A).

Furthermore, the side chain introduction may be carried out as follows: for example, ring opening of the epoxide is carried out using a reducing agent (e.g., lithium aluminum hydride, lithium borohydride, lithium tri-s-butylborohydride and lithium triethylborohydride) after alkylation using 1-bromo-2,3-epoxy-3-methylbutane as the alkylhalide in the presence of the above base. This reaction may be carried out by one step or two steps (the methods of WO 98/09935).

Moreover, the side chain introduction may be carried out by alkylation using an acrylic acid derivative such as ethyl acrylate or N,N-dimethylacrylamide or a haloacetate derivative such as t-butyl bromoacetate in the presence of the above base, followed by reaction with an alkaline metal reagent such as alkyllithium reagent or Grignard reagent (method of U.S. Pat. No. 5,436,401).

(Step 4) Deprotection

According to a conventional method, protecting groups are removed from Compound (E) to give Compound (F).

Hydrochloric acid, sulfuric acid, acetic acid, an acidic ion exchange resin, tetrabutylammonium fluoride, hydrogen fluoride/pyridine, hydrogen fluoride/triethylamine and hydrofluoric acid can be used as the reagent, with tetrabutylammonium fluoride being preferred.

Generally, an ether-based solvent is used as the solvent and preferably tetrahydrofuran is used. The reaction temperature depends on the substance; in general, the reaction is preferably carried out in the range of from room temperature to 65° C.

(Step 5) Photoreaction and Thermal Isomerization

According to a conventional method, Compound (F) is subjected to photoreaction and thermal isomerization to give Compound (G).

The order of Steps 3, 4 and 5 is not particularly limited to the above and Steps 3, 4 and 5 may be carried out in the order of [Step 3→Step 5→Step 4] or [Step 5→Step 3→Step 4]. However Step 4 is not carried out before Step 3.

If necessary, the side chain may be modified by a known method such as catalytic hydrogenation in each of the above Steps.

I-2. Synthesis of Vitamin D derivatives in which X is Sulfur in Formula (1)

Vitamin D derivatives in which X is sulfur, $R_2$ is hydrogen and $R_3$ and $R_4$ together form a double bond between the 16- and 17-positions in Formula (1) can be produced, for example, by the method shown in the following scheme.

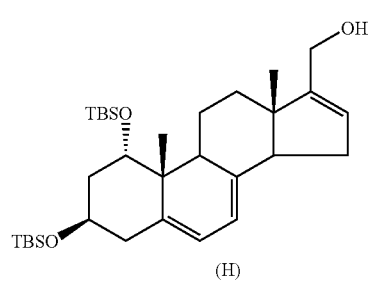

(H)

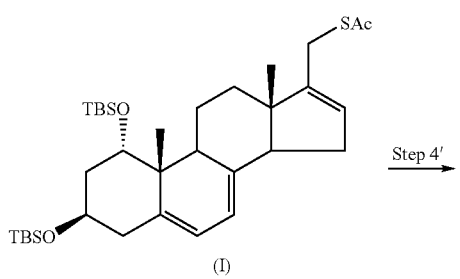

(I)

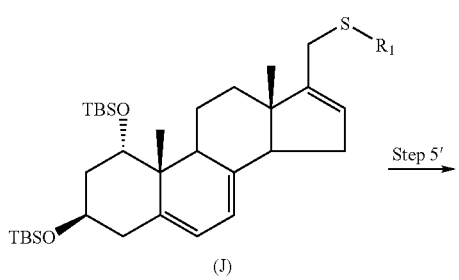

(J)

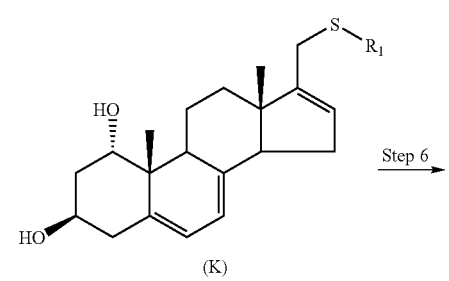

(K)

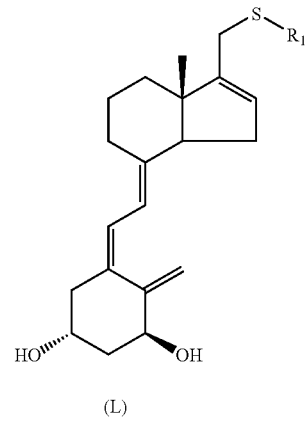

(L)

(Step 3') Introduction of Sulfur Functional Group

Compound (H) is subjected to the following two reactions to give Compound (I). Compound (H) corresponds to Compound (C), in which $R_2$ is hydrogen and which is obtainable by the above Steps (1) and (2) or Steps (1') and (2').

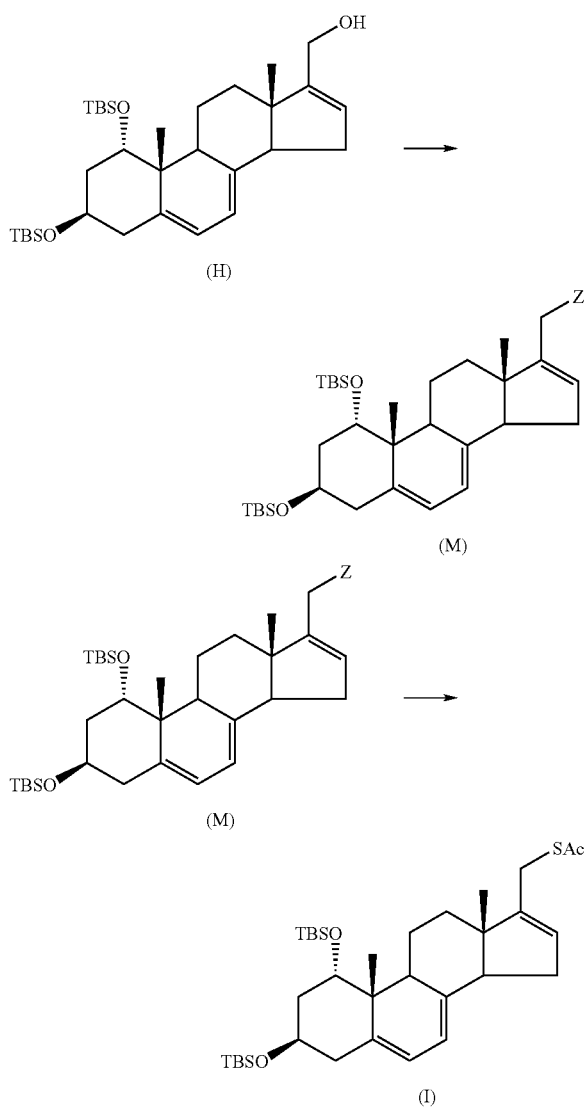

wherein Z is a leaving group, such as chloro, bromo, iodo, mesyloxy or tosyloxy.

Conversion of the leaving group of Compound (H) for obtaining Compound (M) can be carried out according to a conventional method (Larock, R. C. Comprehensive Organic Transformations, 2nd ed.; Wiley-VCH: New York, 1999).

Compound (I) was synthesized by reacting Compound (M) with a metallic salt of thiocarboxylic or dithiocarboxylic acid in an appropriate solvent.

Examples of the metallic salt of thiocarboxylic or dithiocarboxylic acid include sodium thioacetate, potassium thioacetate, sodium thiobenzoate, potassium thiobenzoate, sodium dithioacetate, potassium dithioacetate, sodium dithiobenzoate, potassium dithiobenzoate and the like, with potassium thioacetate being preferred.

Hydrocarbon-, ether-, halogen-, ketone-, ester-, amide-, sulfoxide- and nitrile-based solvents can be used as the solvent. Examples thereof include hexane, benzene, toluene, diethyl ether, tetrahydrofuran, 1,4-dioxane, 1,2-dimethoxyethane, dichloromethane, chloroform, carbon tetrachloride, acetone, ethyl acetate, N,N-dimethylformamide, N,N-dimethylacetamide, 1,3-dimethyl-2-imidazolidinone, 1,3-dimethyl-3,4,5,6-tetrahydro-2(1H)-pyrimidinone, dimethylsulfoxide, acetonitrile and the like. Among them, diethyl ether, tetrahydrofuran, 1,4-dioxane, 1,2-dimethoxyethane, acetone, N,N-dimethylformamide, N,N-dimethylacetamide, 1,3-dimethyl-2-imidazolidinone, dimethylsulfoxide and the like are preferred, and tetrahydrofuran, acetone and dimethylsulfoxide are more preferred. Mixtures of those solvents may also be used in the reaction.

The reaction temperature is not particularly limited unless the reaction can proceed; in general, the reaction is carried out in the range of from −50° C. to 100° C. and preferably from 0° C. to room temperature.

The above two reactions may be carried out continuously. In other words, after converting the hydroxy to a leaving group, the resulting compound may be reacted with a metallic salt of thiocarboxylic or dithiocarboxylic acid without work-up.

(Step 4') Alkaline Solvolysis and S-alkylation

To obtain Compound (J), Compound (I) was subjected to alkaline solvolysis simultaneously with S-alkylation.

Lithium hydroxide, sodium hydroxide, potassium hydroxide, sodium methoxide and potassium t-butoxide can be used for alkaline solvolysis and S-alkylation. Preferably, sodium hydroxide, potassium hydroxide or sodium methoxide is used.

Preferably, water or an alcohol-based solvent (e.g., methanol, ethanol, propanol, butanol, etc.) alone, or an ether-based solvent is used as the solvent. For example, the reaction may be carried out in a solvent system mixed with diethyl ether, tetrahydrofuran, 1,2-dimethoxyethane, 1,4-dioxane, diglyme and the like.

A compound of formula $R_{1a}$-Z (in which Z is a leaving group such as halogen, mesyloxy, tosyloxy or trifluoromethanesulfonyloxy, and $R_{1a}$ is as defined above) or an epoxide such as isobutyleneoxide, 1,2-epoxy-2-ethylbutane or 1,2-epoxy-3-methylbutane can be used as the alkylation agent.

Examples of the compound of $R_{1a}$-Z include 4-bromo-2-methyl-2-butanol, 1-bromo-4-methyl-4-triethylsilyl pentane, 1-bromo-4-hydroxy-4-methyl-2-pentene, 1-bromo-4-hydroxy-4-methyl-2-pentyne and the like.

The reaction temperature is generally in the range of from −40° C. to 100° C., preferably from 0 to 50° C. and more preferably at room temperature.

(Step 5') Deprotection

According to a conventional method, protecting groups are removed from Compound (J).

Hydrochloric acid, sulfuric acid, acetic acid, an acidic ion exchange resin, tetrabutylammonium fluoride, hydrogen fluoride/pyridine, hydrogen fluoride/triethylamine and hydrofluoric acid can be used as the reagent, with acidic ion exchange resin and tetrabutylammonium fluoride being preferred.

Generally, an ether-based solvent is used as the solvent and preferably tetrahydrofuran is used.

The reaction temperature depends on the substance; in general, the reaction is preferably carried out in the range of from room temperature to 65° C.

(Step 6) Photoreaction and Thermal Isomerization

According to a conventional method, Compound (K) is subjected to photoreaction and thermal isomerization to give Compound (L).

The order of Steps 3', 4', 5' and 6 is not particularly limited to that order, however Steps 4' and 5' are not carried out before Step 3'.

II-1. Synthesis of Vitamin D Derivatives in which $R_3$ and $R_4$ are Hydrogen in Formula (1)

Vitamin D derivatives in which $R_3$ and $R_4$ are hydrogen in Formula (1) can be produced, for example, by the method shown in the following scheme by using a compound of Formula (A') (described in E. Murayama, et al, Chem. Pharm. Bull., 34(10), 1986, and JP No. 61-267550 A) as the starting material.

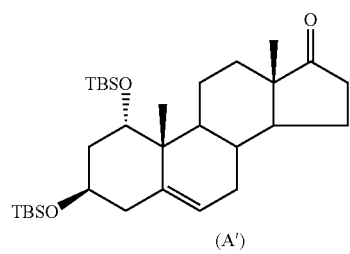

(A')

Step 1
Methylene formation
→

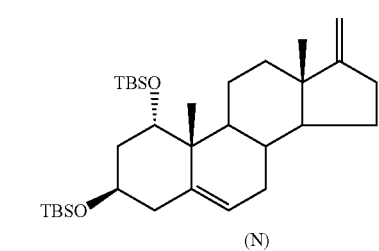

(N)

Step 2
Hydroboration-oxidation
→

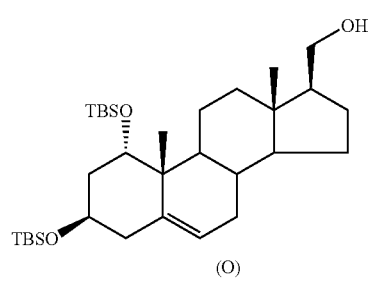

(O)

Step 3
Side chain introduction
→

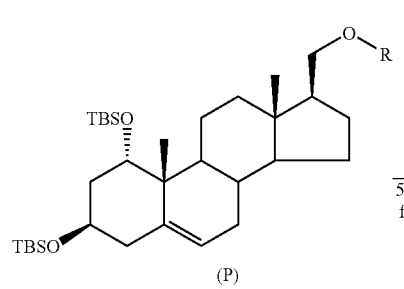

(P)

Step 4
5,7-Diene formation
→

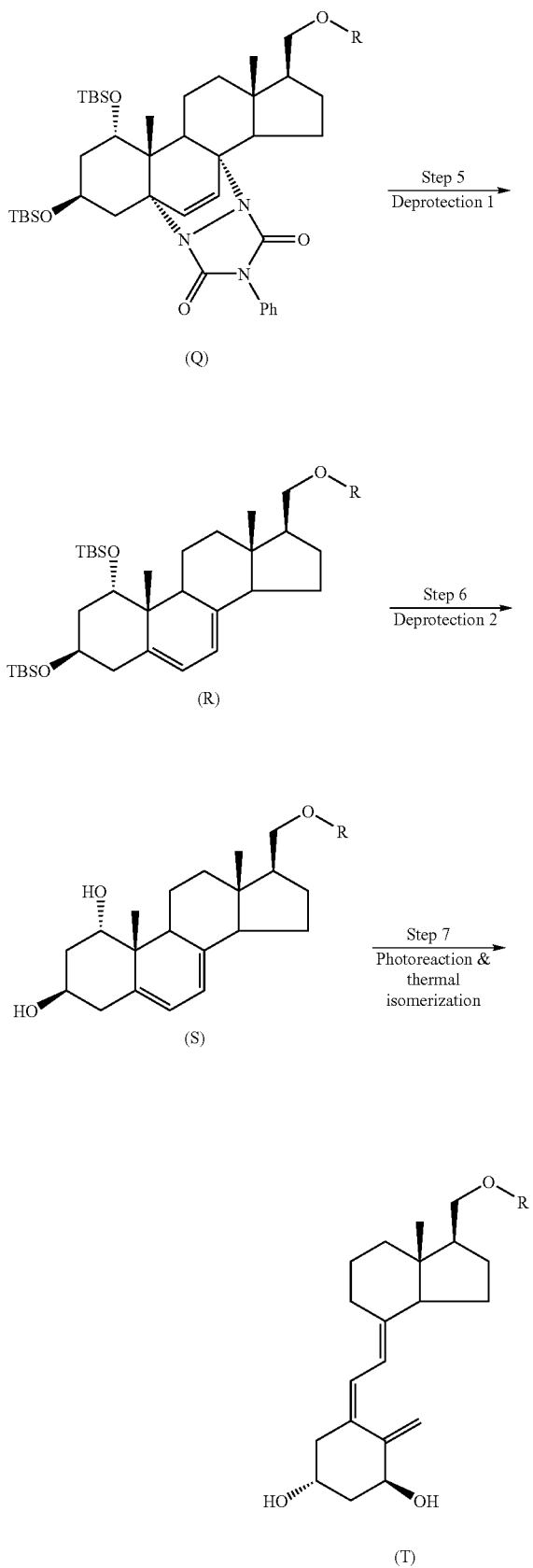

wherein TBS is a t-butyldimethylsilyl group and each R is optionally substituted aryl or optionally substituted alkyl.

(Step 1) Methylene Formation

Process for preparing a compound of Formula (N) from the compound of Formula (A') can be carried out, for example, by Wittig reaction using methyltriphenylphosphonium bromide and the like in the presence of a base.

Metallic hydroxides, metallic hydrides, alkaline metals, metallic dialkylamides and the like can be used as the base. Specific examples thereof include sodium hydroxide, sodium methoxide, sodium hydride, n-butyllithium, s-butyllithium, t-butyllithium, phenyllithium, potassium hydroxide, potassium hydride, potassium t-butoxide, lithium diisopropylamide, sodium diisopropylamide, potassium diisopropylamide, lithium bistrimethylsilylamide, sodium bistrimethylsilylamide, potassium bistrimethylsilylamide and the like, with potassium t-butoxide being preferred.

Hydrocarbon-, ether-, amide- and sulfoxide-based solvents can be used as the solvent; specific examples include pentane, hexane, benzene, toluene, diethyl ether, t-butylmethyl ether, tetrahydrofuran, 1,2-dimethoxyethane, 1,4-dioxane, anisole, 1,3-dimethyl-2-imidazolidinone, 1,3-dimethyl-3,4,5,6-tetrahydro-2(1H)-pyrimidinone, dimethylsulfoxide and the like, with toluene and tetrahydrofuran being preferred.

The reaction temperature is not particularly limited unless the reaction can proceed; generally the reaction is carried out in the range of –50° C. to 150° C. and preferably in the range of 0 to 100° C.

(Step 2) Hydroboration-oxidation

A compound of Formula (O) is produced by hydroboration-oxidation of the compound of Formula (N).

Borane, alkylboranes and dialkylboranes can be used in hydroboration. Examples thereof include diborane, borane-tetrahydrofuran complex, borane-dimethylsulfide complex, borane-triethylamine complex, borane-dimethylamine complex, borane-t-butylamine complex, borane-pyridine complex, disiamylborane, dithexylborane, 9-borabicyclo[3,3,1]nonane and the like, with 9-borabicyclo[3,3,1]nonane being preferred.

Ether- and halogen-based solvents can be used as the solvent. Examples thereof include diethyl ether, t-butylmethyl ether, tetrahydrofuran, 1,2-dimethoxyethane, 1,4-dioxane, anisole, dichloromethane, chloroform, 1,2-dichloroethane and the like, with tetrahydrofuran being preferred.

The reaction temperature is not particularly limited unless the reaction can proceed; generally the reaction is carried out in the range of 0 to 100° C. and preferably at room temperature. Oxidation is carried out by hydrogen peroxide solution and the like in alkaline conditions (e.g., using sodium hydroxide solution).

(Step 3) Side Chain Introduction

According to a similar method as in Step 3 of I-1, Compound (O) is reacted with an alkylation agent corresponding to the side chain in the presence of a base to give Compound (P).

(Step 4) Diene-formation at the 5,7-Positions and Protection.

According to a conventional method, diene-formation at the 5,7-positions of Compound (P) and protection of the formed dienes are carried out to give Compound (Q) (for example, according to the method described in JP No. 61-267550 A).

(Step 5) Deprotection of 5,7-Diene Moieties (Deprotection 1)

According to a conventional method, the diene moieties of the 5,7-positions of Compound (Q) were deprotected to give Compound (R) (for example, according to the method described in Kubodera et al., J. Org. Chem. 1992, 57, 5019).

(Step 6) Deprotection of Silyl Groups (Deprotection 2)

Similarly to Step 4 of I-1, the t-butyldimethylsilyl groups of Compound (R) are removed to give Compound (S) according to a conventional method.

(Step 7) Photoreaction and Thermal Isomerization

Similarly to Step 5 of I-1, Compound (S) is subjected to photoreaction and thermal isomerization to give Compound (T) according to a conventional method.

The order of Steps 3, 4, 5, 6 and 7 is not particularly limited to that order; Step 6 is not carried out before Steps 3 and 4. Step 7 is not carried out before Steps 4 and 5.

If necessary, the side chain of each intermediate may be modified as shown in the following scheme.

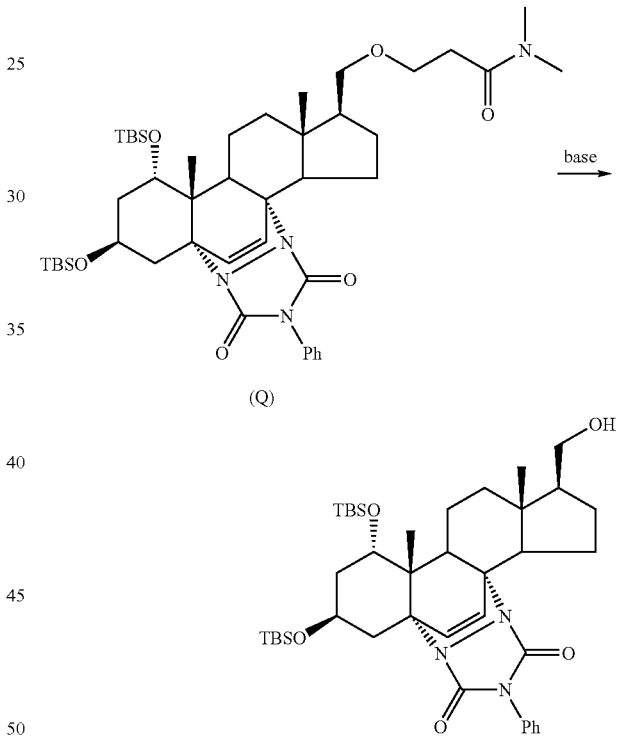

wherein TBS is a t-butyldimethylsilyl group.

In the above, the side chain is modified by reacting Compound (Q) (in which R is $(CH_2)_2CON(CH_3)_2$) with a base. Alkaline metal hydrides, alkaline metal alkoxides, metal dialkylamides, alkaline metals and the like can be used as the base. Preferably sodium hydride, potassium hydride, potassium t-butoxide, lithium diisopropylamide, lithium bis(trimethylsilyl)amide, methyllithium, n-butyllithium and ethylmagnesium bromide and the like are used, with potassium t-butoxide being preferred.

Hydrocarbon-, ether- and amide-based solvents can be used as the solvent. Specific examples thereof include benzene, toluene, diethyl ether, tetrahydrofuran, 1,2-dimethoxyethane, 1,4-dioxane, N,N-dimethylacetamide, N,N-dimethylformamide, 1,3-dimethyl-2-imidazolidinone, 1,3- dimethyl-3,4,5,6-tetrahydro-2(1H)-pyrimidinone and the like. Among them, tetrahydrofuran, 1,2-dimethoxyethane, N,N-dimethylformamide and 1,3-dimethyl-2-imidazolidinone are preferred and tetrahydrofuran is more preferred.

The reaction temperature depends on the substance; in general, the reaction is carried out in the range of −40° C. to the boiling or decomposition temperature of the solvent used in the reaction, preferably in the range of 0 to 100° C., and more preferably at room temperature.

If necessary, the side chain of each intermediate may be modified as shown in the following scheme.

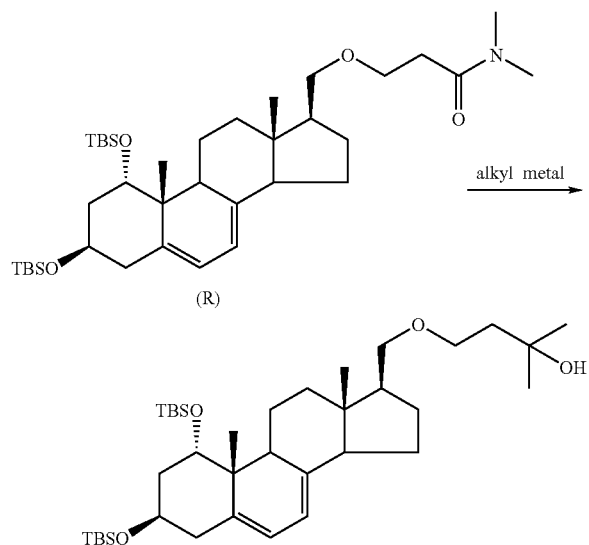

wherein TBS is a t-butyldimethylsilyl group.

In the above, the side chain is modified by reacting Compound (R) (in which R is $(CH_2)_2CON(CH_3)_2$) with an alkaline metal. This reaction may be carried out, for example, by the method described in JP No. 6-72994 A, however it is not specifically limited thereto and can be carried out by conventional methods.

In each of Steps I-1, I-2 and II, each of the intermediates and final products can be purified and isolated by conventional means such as silica gel chromatography, thin layer chromatography and recrystallization.

The thus obtained vitamin D derivatives of Formula (1) are useful as a medicine with a reduced hypercalcemic effect, as is shown in the following Test examples.

The pharmaceutical composition comprising the vitamin D derivative of the present invention may be formulated into desired dosage forms with pharmaceutically acceptable carriers, excipients, disintegrants, lubricants, binders, flavors, colorants, and the like; examples of the dosage forms include tablets, granules, fine granules, capsules, powders, injections, solutions, suspensions, emulsions, percutaneous absorption formulations, suppositories, and the like.

When the therapeutic agent for skin diseases, which contains the vitamin D derivative of the present invention as an active ingredient, is used for treating psoriasis, it may be formulated into external preparations such as ointments, creams and lotions.

The dosage of the therapeutic agent comprising a vitamin D derivative of the present invention as an active ingredient can be appropriately chosen depending on the target disease, the conditions, body type, constitution, age and sex of the patient, the administration route, the dosage form and other factors. In general, the dosage as the active ingredient is in the range of 0.001 μg/day to 10,000 μg/day, preferably 0.01 μg/day to 1,000 μg/day for oral administration, in the range of 0.01 μg/day to 10,000 μg/day, preferably 0.1 μg/day to 1,000 μg/day for injection, and in the range of 1 μg/day to 50,000 μg/day, preferably 10 μg/day to 5,000 μg/day for external preparation, which doses may be administered at a time or in divided portions twice or three times a day.

When the therapeutic agent for skin diseases containing a vitamin D derivative of the present invention as an active ingredient is used for treating psoriasis, topical application using external preparations and the like is preferred; systemic application using oral formulations or injections may be also employed.

EXAMPLES

The present invention will be described specifically by way of the following Examples, which in no way limit the invention. In Examples, NMR spectra were measured using tetramethylsilane or chloroform as the internal standard and unless otherwise specified, using $CDCl_3$ as the solvent. Mass spectra (MS) were measured by EI mode at an ionic voltage of 70 eV. Ultraviolet absorption spectra (UV) were measured in an ethanol solvent. Column chromatography was carried out using silica gel (75–150 μm or 40–63 μm) and thin layer chromatography was carried out using silica gel (1 mm, 0.5 mm or 0.25 mm thickness, each 20×20 cm).

Example 1

Synthesis of 17-acetylthiomethyl-1α,3β-bis(tert-butyldimethylsilyloxy)androsta-5,7,16-triene (1) Synthesis of 1α,3β-bis(tert-butyldimethylsilyloxy)-17-(2,4,6-triisopropylbenzenesulfonylhydrazono)androsta-5,7-diene 1α,3β-Bis(tert-butyldimethylsilyloxy)-17-oxoandrosta-5,7-diene (1.64 g, 3.08 mmol) and 2,4,6-triisopropylbenzenesulfonylhydrazide (1.01 g, 3.39 mmol) were dissolved in ethyl acetate (6 ml) and stirred at room temperature for 16 hours. The reaction mixture was concentrated under reduced pressure and the thus obtained residue was purified by column chromatography (hexane:ethyl acetate=15:1) to give the titled compound (1.86 g, 75%).

$^1$H NMR δ: 7.15(s, 2H), 6.98(brs, 1H), 5.58(d, J=5.8 Hz, 1H), 5.40–5.33(m, 1H), 4.28–4.20(m, 2H), 4.18–3.93(m, 1H), 3.70–3.63(m, 1H), 2.95–2.74(m, 2H), 1.30–1.22(m, 24H), 0.88(s, 9H), 0.85(s, 9H), 0.68(s, 3H), 0.09(s, 3H), 0.06(s, 3H), 0.04(s, 3H), 0.03(s, 3H).

IR(KBr): 3232, 2956, 2860, 1600, 1462, 1426, 1384, 1372, 1362, 1328, 1254, 1214, 1194, 1166, 1154, 1102, 1038, 1006, 968, 952, 938, 928, 916, 878, 834, 774, 716, 666, 548 $cm^{-1}$.

(2) Synthesis of 1α,3β-bis(tert-butyldimethylsilyloxy)-17-(hydroxymethyl)androsta-5,7,16-triene A solution of 1α,3β-bis(tert-butyldimethylsilyloxy)-17-(2,4,6-triisopropylbenzenesulfonylhydrazono)androsta-5,7-diene (32.7 mg, 0.0403 mmol) in hexane (0.8 ml) and tetramethylethylenediamine (0.16 ml) was cooled to −78° C. and 1.53M n-butyl lithium (0.106 ml, 0.161 mmol) was added. After stirring at −78° C. for 2 hours, the reaction mixture was warmed to 0° C., stirred for 15 min., paraformaldehyde (10 mg, 0.33 mmol) was added and stirred at 0° C. for 1 hour then at room temperature for 1 hour. After adding brine, the reaction mixture was extracted with dichloromethane, the extract was dried over anhydrous sodium sulfate and evaporated for removing the solvent. The thus obtained residue was purified by column chromatography (hexane:ethyl acetate=6:1) to give the titled compound (13.6 mg, 62%).

(3) Synthesis of 17-acetylthiomethyl-1α,3β-bis(tert-butyldimethylsilyloxy)androsta-5,7,16-triene To a solution of 1α,3β-bis(tert-butyldimethylsilyloxy)-17-(hydroxymethyl)androsta-5,7,16-triene (4.00 g, 7.34 mmol) in tetrahydrofuran (70 ml), was added triethylamine (4.10 ml, 29.4 mmol), followed by the dropwise addition of methanesulfonyl chloride (1.70 ml, 22.0 mmol) at −10° C. and stirring for 20 min. The reaction mixture was warmed to room temperature and a solution of potassium thioacetate (3.73 g, 29.4 mmol) in dimethylsulfoxide (70 ml) was added. After stirring for 30 min., the mixture was diluted with hexane, washed with water, the organic layer was dried over anhydrous magnesium sulfate and evaporated for removing the solvent. The thus obtained residue was purified by silica gel column chromatography (hexane:ethyl acetate=15:1) to give the titled compound (3.91 g, 88%) as a colorless oil.

IR(neat): 2954, 2929, 2897, 2856, 1695, 1471, 1462, 1371, 1360, 1254, 1099 cm$^{-1}$. $^1$H NMR δ: 0.05(s, 1H), 0.07(s, 3H), 0.07(s, 3H), 0.11(s, 3H), 0.82(s, 3H), 0.88(s, 18H), 0.94(s, 3H), 2.34(s, 3H), 2.79–2.90(m, 1H), 3.52–3.68 (m, 2H), 3.68–3.73(m, 1H), 3.98–4.12(m, 1H), 5.35–5.41 (m, 1H), 5.57–5.64(m, 2H). MS m/z: 602(M$^+$), 413(100%). UV λ$_{max}$ nm: 234, 261, 271, 281, 294.

Example 2

Synthesis of 1α,3β-bis(tert-butyldimethylsilyloxy)-20-hydroxy-20-methylpregna-5,7,16-triene After the procedure of Step (1) of Example 1, the following step was carried out instead of Step (2). A solution of 1α,3β-bis(tert-butyldimethylsilyloxy)-17-(2,4,6-triisopropylbenzenesulfonylhydrazono)androsta-5,7-diene (91.0 mg, 0.112 mmol) in hexane (2.5 ml) and tetramethylethylenediamine (0.50 ml) was cooled to −78° C. and 1.53M n-butyl lithium (0.293 ml, 0.449 mmol) was added. The reaction mixture was stirred at −78° C. for 2 hours, warmed to 0° C. and stirred for 15 min., followed by the addition of acetone (0.10 ml) and stirring at 0° C. for 20 min. After adding brine, the reaction mixture was extracted with dichloromethane; the extract was dried over anhydrous sodium sulfate and evaporated for removing the solvent. The thus obtained residue was purified by column chromatography (hexane:ethyl acetate=10:1) to give the titled compound (28.8 mg, 45%).

$^1$H NMR δ: 5.65(dd, J=2.2, 2.5 Hz, 1H), 5.61(d, J=5.5 Hz, 1H), 5.44–5.38(m, 1H), 4.12–3.99(m, 1H), 3.73–3.68(m, 1H), 2.90–2.80(m, 1H), 2.40–2.26(m, 3H), 2.20–2.08(m, 3H), 1.99–1.88(m, 1H), 1.41(s, 6H), 0.96(s, 3H), 0.94(s, 3H), 0.88(s, 18H), 0.11(s, 3H), 0.07(s, 6H), 0.05(s, 3H).

IR(KBr): 3480, 2952, 2928, 2892, 2856, 1470, 1460, 1372, 1360, 1254, 1100, 1084, 1066, 968, 878, 834, 812, 774 cm$^{-1}$.

Example 3

Instead of Steps (1) and (2) of Example 1, the following Steps (1) and (2) were carried out.

(1) Synthesis of 1α,3β-bis(tert-butyldimethylsilyloxy)androsta-5,7-diene-(17S)-spiro-2'-oxirane To dimethylsulfoxide (13 ml), was added sodium hydride (60% in oil, 0.2821 g, 7.06 mmol), followed by stirring at 80° C. for 1 hour. The thus obtained suspension was cooled to 0° C., diluted with tetrahydrofuran (19 ml) and a solution of trimethylsulfonium iodide (1.33 g, 6.50 mmol) in dimethylsulfoxide (9 ml) was added dropwise, followed by stirring at 0° C. for 35 min. After adding a solution of 1α,3β-bis(tert-butyldimethylsilyloxy)-17-oxoandrosta-5,7-diene (1.0 g, 1.88 mmol) in tetrahydrofuran (7 ml), the mixture was stirred at room temperature for 14 hours. The resulting reaction mixture was poured into a saturated aqueous ammonium chloride, extracted with ethyl acetate, the extract was washed with water and saturated brine, dried over anhydrous sodium sulfate and evaporated for removing the solvent. The thus obtained residue was purified by column chromatography (hexane:ethyl acetate=6:1) to give the titled compound (0.93 g, 91%) as a white foam.

$^1$H NMR δ: 0.05(s, 3H), 0.06(s, 3H), 0.07(s, 3H), 0.11(s, 3H), 0.88(s, 3H), 0.89(s, 3H), 2.65(d, J=4.9 Hz, 1H), 2.93(d, J=4.9 Hz, 1H), 3.71(brs, 1H), 3.98–4.12(m, 1H), 5.35–5.43 (m, 1H), 5.57–5.64(m, 1H).

(2) Synthesis of 1α,3β-bis(tert-butyldimethylsilyloxy)-17-(hydroxymethyl)androsta-5,7,16-triene To a solution of 1α,3β-bis(tert-butyldimethylsilyloxy)androsta-5,7-diene-(17S)-spiro-2'-oxirane (20 g, 36.7 mmol) in 1,2-dichlorobenzene (130 ml), was added aluminum isopropoxide (22 g, 108 mmol) under an argon atmosphere, followed by stirring at 130° C. for 1.5 hours. After adding Rochelle salt solution, the mixture was extracted with ethyl acetate (twice). The extracts were washed with water, dried over anhydrous sodium sulfate and evaporated to remove the solvent. The thus obtained residue was purified by column chromatography (hexane:ethyl acetate=6:1) to give the titled compound (10 g, 50%) as a white solid.

IR(neat): 3392, 2954, 2929, 2856, 1462, 1254, 1097, 1082 cm$^{-1}$.

$^1$H NMR δ: 0.05(s, 3H), 0.07(s, 6H), 0.11(s, 3H), 0.88(s, 3H), 0.89(s, 3H), 3.71(brs, 1H), 4.00(brs, 1H), 4.22(s, 2H), 5.40(brs, 1H), 5.57–5.66(m, 2H).

MS m/z: 544(M$^+$), 355(100%). UV λ$_{max}$ nm: 270, 281, 293.

Example 4

Synthesis of 17-acetylthiomethyl-1α,3β-bis(tert-butyldimethylsilyloxy)androsta-5,7,16-triene After the procedure of Steps (1) and (2) of Example 1, the following Step was carried out instead of Step (3) of Example 1.

To a solution of 1α,3β-bis(tert-butyldimethylsilyloxy)-17-(hydroxymethyl)androsta-5,7,16-triene (100 mg, 0.183 mmol), triphenylphosphine (96.0 mg, 0.366 mmol) and imidazole (49.8 mg, 0.732 mmol) in dichloromethane (2 ml), was added N-bromosuccinimide (65.1 mg, 0.366 mmol) at 0° C., followed by stirring at room temperature. After 1 hour, hexane was added to the mixture and washed with water and then saturated brine. The organic layer was dried over anhydrous magnesium sulfate and evaporated under reduced pressure to remove the solvent, giving a mixture (150 mg) containing 1α,3β-bis(tert-butyldimethylsilyloxy)-17-(bromomethyl)androsta-5,7,16-triene. The mixture was dissolved in acetone (1.5 ml), to which potassium thioacetate (31.4 mg, 0.275 mmol) was added, followed by stirring for 30 min. The reaction mixture was diluted with hexane, filtered and the resulting filtrate was evaporated under reduced pressure to remove the solvent. The residue was purified by preparative thin layer chromatography (2 sheets (each 0.5 mm thickness), hexane:ethyl acetate=20:1, developed once) to give the titled compound (70.2 mg, 64%) as a colorless oil.

Example 5

(1) Synthesis of 1α,3β-bis(tert-butyldimethylsilyloxy)-17-(4-triethylsilyloxy-4-methylpentyloxymethyl)androsta-5,7,16-triene To a solution of 1α,3β-bis(tert-butyldimethylsilyloxy)-17-(hydroxymethyl)androsta-5,7,16-triene (200 mg, 0.367 mmol), sodium hydride (60% in oil, 45 mg, 1.125 mmol) and 15-crown-5 (80 mg, 0.363 mmol) in tetrahydrofuran (1 ml), was added 1-bromo-4-methyl-4-(triethylsilyloxy)pentane (220 mg, 0.745 mmol) at room temperature, followed by reflux under heating for 1 hour. The reaction solution was diluted with ethyl acetate, followed by the dropwise addition of water under cooling with ice and washing with saturated brine. The organic layer was dried over anhydrous magnesium sulfate. After distilling off the solvent under reduced pressure, the thus obtained residue was purified by column chromatography (hexane:ethyl acetate=15:1) to give the titled compound (278.7 mg, quant.) as a colorless oil.

IR(neat): 2932, 1460, 1364, 1252, 1068, 834, 774 cm$^{-1}$.
$^1$H NMR δ: 0.05(s, 3H), 0.06(s, 6H), 0.11(s, 3H), 0.56(q, J=8.0 Hz, 6H), 0.83(s, 3H), 0.88(s, 21H), 0.94(t, J=8.0 Hz, 9H), 1.20(s, 6H), 2.80–2.92(m, 1H), 3.34–3.48(m, 2H), 3.70(brs, 1H), 4.01(brs, 1H), 3.99–4.13(m, 1H), 5.36–5.43 (m, 1H), 5.61(d, J=5.8 Hz, 1H), 5.64(s, 1H).

MS m/z: 759(M$^+$+1), 73(100%). UV λ$_{max}$ nm: 271, 281, 294.

(2) Synthesis of 1α,3β-dihydroxy-17-(4-hydroxy-4-methylpentyloxymethyl)androsta-5,7,16-triene To a solution of 1α,3β-bis(tert-butyldimethylsilyloxy)-17-(4-triethylsilyloxy-4-methylpentyloxymethyl)androsta-5,7,16-triene (278.7 mg, 0.367 mmol) in tetrahydrofuran (2 ml), was added a 1M tetra-n-butylammonium fluoride tetrahydrofuran solution (3.3 ml, 3.3 mmol), followed by reflux under heating for 14 hours. The reaction solution was diluted with ethyl acetate, washed with 5% hydrochloric acid, a saturated aqueous sodium bicarbonate solution and saturated brine in that order, the organic layer was dried over anhydrous magnesium sulfate and evaporated under reduced pressure to remove the solvent. The thus obtained residue was purified by column chromatography (dichloromethane:ethanol=10:1) and preparative thin layer chromatography (4 sheets (each 0.5 mm thickness), dichloromethane:ethanol=20:1, developed twice, and then dichloromethane:ethanol=10:1, developed twice) to give the titled compound (56.3 mg, 37%) as a colorless foam.

IR(neat): 3384, 2932, 1462, 1370, 1084, 1054, 944, 730 cm$^{-1}$.

$^1$H NMR δ: 0.84(s, 3H), 0.98(s, 3H), 1.22(s, 6H), 2.47–2.61(m, 1H), 2.73–2.86(m, 1H), 3.36–3.55(m, 2H), 3.77(brs, 1H), 3.94–4.16(m, 2H), 5.40–5.50(m, 1H), 5.64(s, 1H), 5.59–5.79(m, 1H).

MS m/z: 298(M$^+$-HOCH$_2$CH$_2$CH$_2$C(CH$_3$)$_2$OH), 83(100%). UV λ$_{max}$ nm: 271, 281, 293.

(3) Synthesis of 1α,3β-dihydroxy-17-(4-hydroxy-4-methylpentyloxymethyl)-9,10-secoandrosta-5,7,10(19),16-tetraene 1α,3β-Dihydroxy-17-(4-hydroxy-4-methylpentyloxymethyl)androsta-5,7,16-triene (55.0 mg, 0.132 mmol) was dissolved in ethanol (200 ml). While stirring the solution and bubbling argon thereinto at 0° C., the solution was irradiated using a 400 W high-pressure mercury lamp with a Vycor filter for 4.5 min. and then subjected to reflux under heating for 1.5 hours. The reaction mixture was cooled to room temperature, evaporated under reduced pressure to remove the solvent and the thus obtained residue was purified by preparative thin layer chromatography (1 sheet (0.5 mm thickness), dichloromethane:ethanol=20:1, developed once, and dichloromethane:ethanol=10:1, developed twice; 1 sheet (0.25 mm thickness), hexane:ethyl acetate:ethanol=10:5:1, developed three times; and 1 sheet (0.25 mm thickness), dichloromethane:ethyl acetate=3:1 developed once, and dichloromethane:ethyl acetate=2:1, developed twice), giving the titled compound (1.802 mg, 3%) as a colorless oil.

IR(neat): 3400, 2936, 1446, 1364, 1058, 730 cm$^{-1}$.
$^1$H NMR δ: 0.73(s, 3H), 1.22(s, 6H), 2.26–2.38(m, 1H), 2.39–2.49(m, 1H), 2.55–2.65(m, 1H), 2.76–2.87(m, 1H), 3.36–3.53(m, 2H), 3.94–4.08(m, 2H), 4.19–4.30(m, 1H), 4.40–4.48(m, 1H), 5.01(s, 1H), 5.34(s, 1H), 5.60(s, 1H), 6.09(d, J=11.6 Hz, 1H), 6.37(d, J=11.6 Hz, 1H).

MS m/z: 416(M$^+$), 134(100%). UV λ$_{max}$ nm: 263.

Example 6

(1) Synthesis of 1α,3β-bis(tert-butyldimethylsilyloxy)-17-{4-ethyl-4-(triethylsilyloxy)hexyloxymethyl}androsta-5,7,16-triene 1α,3β-Bis(tert-butyldimethylsilyloxy)-17-(hydroxymethyl)androsta-5,7,16-triene (400 mg, 0.734 mmol), 1-bromo-4-ethyl-4-(triethylsilyloxy)hexane (475 mg, 1.47 mmol), sodium hydride (60% in oil, 88 mg, 2.20 mmol), 15-crown-5 (162 mg, 0.735 mmol) and tetrahydrofuran (1 ml) were subjected to reaction using a procedure similar to that of Example 5(1) (reflux under heating for 1 hour), worked up and purified by column chromatography (hexane:toluene=3:2) to give the titled compound (569 mg, 98%) as a colorless oil.

IR(neat): 2954, 1462, 1373, 1254, 1099, 1072 cm$^{-1}$.
$^1$H NMR δ: 0.05(s, 3H), 0.07(s, 6H), 0.11(s, 3H), 0.57(q, J=7.9 Hz, 6H), 0.88(s, 9H), 0.88(s, 9H), 0.94(s, 3H), 0.94(q, J=7.9 Hz, 9H), 1.46(q, J=7.6 Hz, 4H), 2.81–2.90(m, 1H), 3.35–3.46(m, 2H), 3.69–3.73(br, 1H), 3.97–4.11(m, 3H), 5.36–5.42(m, 1H), 5.57–5.62(m, 1H), 5.64(brs, 1H).

MS m/z: 654(M$^+$-HOTBS), 73(100%). UV λ$_{max}$ nm: 270, 281, 293.

(2) Synthesis of 17-(4-ethyl-4-hydroxyhexyloxymethyl)-1α,3β-dihydroxyandrosta-5,7,16-triene 1α,3β-Bis(tert-butyldimethylsilyloxy)-17-{4-ethyl-4-(triethylsilyloxy)hexyloxymethyl}androsta-5,7,16-triene (559 mg, 0.710 mmol) and a 1M tetra-n-butylammonium fluoride tetrahydrofuran solution (6 ml) were subjected to reaction using a procedure similar to that of Example 5(2) (4 hours), worked up and purified by column chromatography (ethyl acetate:dichloromethane=4:1 and then ethyl acetate) to give the titled compound (292 mg, 93%) as a colorless foam.

IR(neat): 3369, 2964, 2937, 2879, 2854, 1460, 1369, 1149, 1036 cm$^{-1}$.

$^1$H NMR δ: 0.89(s, 3H), 0.99(s, 3H), 1.47(q, J=7.6 Hz, 4H), 2.74–2.85(m, 1H), 3.39–3.50(m, 2H), 3.79(brs, 1H), 3.96–4.17(m, 3H), 5.43–5.49(m, 1H), 5.65(brs, 1H), 5.75 (brd, J=5.9 Hz, 1H).

MS m/z: 444(M$^+$), 69(100%). UV λ$_{max}$ nm: 271, 281, 293.

(3) Synthesis of 17-(4-ethyl-4-hydroxyhexyloxymethyl)-1α,3β-dihydroxy-9,10-secoandrosta-5,7,10(19),16-tetraene 17-(4-ethyl-4-hydroxyhexyloxymethyl)-1α,3β-dihydroxyandrosta-5,7,16-triene (261 mg, 0.587 mmol) and ethanol (200 ml) were subjected to reaction using a procedure similar to that of Example 5(3) (irradiation for 12 min. 15 sec., reflux under heating for 2 hours) and purified by preparative thin layer chromatography (7 sheets (each 0.5 mm thickness), dichloromethane:ethanol=10:1, developed twice; 1 sheet (0.5 mm thickness), toluene:ethyl acetate=1:1, developed three times; and then 1 sheet (0.5 mm thickness), dichloromethane:ethyl acetate=1:1, developed twice) to give the titled compound (2.48 mg, 1%) as a colorless glassy substance.

IR(neat): 3367, 2931, 2879, 2850, 1456, 1367, 1350, 1055 cm$^{-1}$.

$^1$H NMR δ: 0.73(s, 3H), 1.47(q, J=7.3 Hz, 4H), 2.77–2.88 (m, 1H), 3.39–3.50(m, 2H), 3.93–4.07(m, 2H), 4.17–4.30 (br, 1H), 4.40–4.49(m, 1H), 5.01(brs, 1H), 5.34(brs, 1H), 5.60(brs, 1H), 6.10(d, J=11.2 Hz, 1H), 6.37(d, J=11.2 Hz, 1H).

MS m/z: 426(M$^+$-H$_2$O), 134(100%). UV λ$_{max}$ nm: 264.

Example 7

(1) Synthesis of 1α,3β-bis(tert-butyldimethylsilyloxy)-17-(5-triethylsilyloxy-5-methylhexyloxymethyl)androsta-5,7,16-triene 1α,3β-Bis(tert-butyldimethylsilyloxy)-17-(hydroxymethyl)androsta-5,7,16-triene (200 mg, 0.367 mmol), 1-bromo-5-triethylsilyloxy-5-methylhexane (227 mg, 0.734 mmol), sodium hydride (60% in oil, 44 mg, 1.10 mmol), 15-crown-5 (81 mg, 0.368 mmol) and tetrahydrofuran (0.5 ml) were subjected to reaction using a procedure similar to that of Example 5(1) (reflux under heating for 1 hour), worked up and purified by column chromatography (hexane:toluene=3:2) to give the titled compound (270 mg, 95%) as a colorless oil.

IR(neat): 2954, 2931, 2858, 1462, 1362, 1254, 1099, 1080 cm$^{-1}$.

$^1$H NMR δ: 0.05(s, 3H), 0.06(s, 6H), 0.11(s, 3H), 0.56(q, J=7.9 Hz, 6H), 0.84(s, 3H), 0.88(s, 9H), 0.88(s, 9H), 0.94(s, 3H), 0.94(q, J=7.9 Hz, 9H), 1.18(s, 6H), 2.80–2.91(m, 1H), 3.37–3.47(m, 2H), 3.71(brs, 1H), 3.96–4.11(m, 3H), 5.36–5.41(m, 1H), 5.57–5.62(m, 1H), 5.64(brs, 1H).

MS m/z: 773(M$^+$+1), 73(100%). UV λ$_{max}$ nm: 270, 281, 293.

(2) Synthesis of 1α,3β-dihydroxy-17-(5-hydroxy-5-methylhexyloxymethyl)androsta-5,7,16-triene 1α,3β-Bis(tert-butyldimethylsilyloxy)-17-(5-triethylsilyloxy-5-methylhexyloxymethyl)androsta-5,7,16-triene (420 mg, 0.543 mmol) and a 1M tetra-n-butylammonium fluoride tetrahydrofuran solution (6 ml) were subjected to reaction using a procedure similar to that of Example 5(2) (4 hours), worked up and purified by column chromatography (ethyl acetate:dichloromethane=4:1) to give the titled compound (220 mg, 94%) as a colorless foam.

IR(neat): 3360, 2964, 2937, 2862, 1462, 1369, 1198, 1059 cm$^{-1}$.

$^1$H NMR δ: 0.84(s, 3H), 0.99(s, 3H), 1.21(s, 6H), 3.38–3.50(m, 1H), 3.80(brs, 1H), 3.96–4.18(m, 3H), 5.43–5.51(m, 1H), 5.65(brs, 1H), 5.73–5.79(m, 1H).

MS m/z: 412(M$^+$-H$_2$O), 59(100%). UV λ$_{max}$ nm: 271, 281, 293.

(3) Synthesis of 1α,3β-dihydroxy-17-(5-hydroxy-5-methylhexyloxymethyl)-9,10-secoandrosta-5,7,10(19),16-tetraene 1α,3β-Dihydroxy-17-(5-hydroxy-5-methylhexyloxymethyl)androsta-5,7,16-triene (201 mg, 0.467 mmol) and ethanol (200 ml) were subjected to reaction using a procedure similar to that of Example 5(3) (irradiation for 11 min. 15 sec., reflux under heating for 2 hours) and purified by preparative thin layer chromatography (5 sheets (each 0.5 mm thickness), dichloromethane:ethanol=10:1, developed twice; 2 sheets (each 0.5 mm thickness), toluene:ethyl acetate=1:1, developed three times; and 2 sheets (each 0.5 mm thickness), dichloromethane:ethyl acetate=1:1, developed three times) to give the titled compound (19.3 mg, 10%) as a colorless glassy substance.

IR(neat): 3369, 2935, 2864, 2848, 1435, 1367, 1209, 1157, 1059 cm$^{-1}$.

$^1$H NMR δ: 0.74(s, 3H), 1.21(s, 6H), 2.76–2.87(m, 1H), 3.36–3.50(m, 2H), 3.93–4.07(m, 2H), 4.18–4.29(br, 1H), 4.39–4.49(br, 1H), 5.01(brs, 1H), 5.34(brs, 1H), 5.60(brs, 1H), 6.10(d, J=11.2 Hz, 1H), 6.37(d, J=11.2 Hz, 1H).

MS m/z: 430(M$^+$), 134(100%). UV λ$_{max}$ nm: 264.

Example 8

(1) Synthesis of 1α,3β-bis(tert-butyldimethylsilyloxy)-17-(4-triethylsilyloxy-4-methyl-2-pentynyloxymethyl)androsta-5,7,16-triene 1α,3β-Bis(tert-butyldimethylsilyloxy)-17-(hydroxymethyl)androsta-5,7,16-triene (200 mg, 0.367 mmol), 1-bromo-4-triethylsilyloxy-4-methyl-2-pentyne (216 mg, 0.741 mmol), sodium hydride (60% in oil, 44 mg, 1.10 mmol) 15-crown-5 (81 mg, 0.368 mmol) and tetrahydrofuran (1 ml) were subjected to reaction using a procedure similar to that of Example 5(1) (at room temperature 17 hours), worked up and purified by column chromatography (hexane:toluene=3:2) to give the titled compound (183 mg, 66%) as a pale yellow oil.

IR(neat): 2954, 2931, 2877, 2856, 1458, 1375, 1360, 1252, 1163, 1082, 1038 cm$^{-1}$.

$^1$H NMR δ: 0.06(s, 3H), 0.07(s, 6H), 0.11(s, 3H), 0.67(q, J=7.9 Hz, 6H), 0.84(s, 3H), 0.88(s, 9H), 0.89(s, 9H), 0.96(t, J=7.6 Hz, 9H), 1.49(s, 6H), 2.80–2.92(m, 1H), 3.98–4.10(br,

1H), 4.10(brs, 2H), 4.16(s, 2H), 5.35–5.43(m, 1H), 5.61(brd, J=5.3 Hz, 1H), 5.69(brs, 1H).

MS m/z: 754(M$^+$), 73(100%). UV $\lambda_{max}$ nm: 271, 282, 294.

(2) Synthesis of 1α,3β-dihydroxy-17-(4-hydroxy-4-methyl-2-pentynyloxymethyl)androsta-5,7,16-triene 1α,3β-Bis(tert-butyldimethylsilyloxy)-17-(4-triethylsilyloxy-4-methyl-2-pentynyloxymethyl)androsta-5,7,16-triene (480 mg, 0.635 mmol) and 1M tetra-n-butylammonium fluoride tetrahydrofuran solution (6 ml) were subjected to reaction using a procedure similar to that of Example 5(2) (4 hours), worked up and purified by column chromatography (ethyl acetate:dichloromethane=4:1 followed by ethyl acetate) to give the titled compound (240 mg, 92%) as a pale yellow foam.

IR(neat): 3330, 2974, 2933, 2852, 1458, 1369, 1234, 1167, 1059 cm$^{-1}$.

$^1$H NMR δ: 0.85(s, 3H), 0.99(s, 3H), 1.53(s, 6H), 2.73–2.87(m, 1H), 3.76–3.82(br, 1H), 4.01–4.17(m, 4H), 5.43–5.50(m, 1H), 5.70(brs, 1H), 5.75(dd, J=5.6, 2.0 Hz, 1H).

MS m/z: 412(M$^+$), 105(100%). UV $\lambda_{max}$ nm: 271, 282, 294.

(3) Synthesis of 1α,3β-dihydroxy-17-(4-hydroxy-4-methyl-2-pentynyloxymethyl)-9,10-secoandrosta-5,7,10(19),16-tetraene 1α,3β-Dihydroxy-17-(4-hydroxy-4-methyl-2-pentynyloxymethyl)androsta-5,7,16-triene (143 mg, 0.347 mmol) and ethanol (200 ml) were subjected to reaction using a procedure similar to that of Example 5(3) (irradiation for 7 min., reflux under heating for 2 hours) and purified by preparative thin layer chromatography (3 sheets (each 0.5 mm thickness), dichloromethane:ethanol=10:1, developed twice; 2 sheets (each 0.5 mm thickness), toluene:ethyl acetate=1:1, developed twice; and 2 sheets (each 0.5 mm thickness), dichloromethane:ethyl acetate=1:1, developed three times) to give the titled compound (6.00 mg, 4%) as a colorless glassy substance.

IR(neat): 3363, 2978, 2931, 2848, 1437, 1363, 1234, 1167, 1061 cm$^{-1}$.

$^1$H NMR δ: 0.74(s, 3H), 1.53(s, 6H), 2.76–2.87(m, 1H), 4.08(brs, 2H), 4.15(brs, 2H), 4.18–4.29(m, 1H), 4.38–4.50(m, 1H), 5.01(brs, 1H), 5.34(brs, 1H), 5.66(brs, 1H), 6.10(d, J=11.2 Hz, 1H), 6.37(d, J=11.2 Hz, 1H).

MS m/z: 412(M$^+$), 134(100%). UV $\lambda_{max}$ nm: 264.

Example 9

(1) Synthesis of 1α,3β-bis(tert-butyldimethylsilyloxy)-17-{4-triethylsilyloxy-4-methyl-(2E)-pentenyloxymethyl}androsta-5,7,16-triene 1α,3β-Bis(tert-butyldimethylsilyloxy)-17-(hydroxymethyl)androsta-5,7,16-triene (400 mg, 0.734 mmol), 1-bromo-4-triethylsilyloxy-4-methyl-(2E)-pentene (431 mg, 1.47 mmol), sodium hydride (60% in oil, 88 mg, 2.20 mmol), 15-crown-5 (162 mg, 0.735 mmol) and tetrahydrofuran (1 ml) were subjected to reaction using a procedure similar to that of Example 5(1) (at room temperature for 2 hours), worked up and purified by column chromatography (hexane:toluene=3:2) to give the titled compound (556 mg, 100%) as a colorless oil.

IR(neat): 2954, 2929, 2856, 1462, 1371, 1360, 1254, 1149, 1099, 1074, 1051 cm$^{-1}$.

$^1$H NMR δ: 0.05(s, 3H), 0.07(s, 6H), 0.11(s, 3H), 0.57(q, J=7.9 Hz, 6H), 0.84(s, 3H), 0.88(s, 9H), 0.88(s, 9H), 0.94(s, 3H), 0.94(t, J=7.9 Hz, 9H), 1.31(s, 6H), 2.79–2.92(m, 1H), 3.71(brs, 1H), 3.89–4.11(m, 5H), 5.35–5.41(m, 1H), 5.55–5.85(m, 4H).

MS m/z: 756(M$^+$), 73(100%). UV $\lambda_{max}$ nm: 271, 282, 294.

(2) Synthesis of 1α,3β-dihydroxy-17-(4-hydroxy-4-methyl-(2E)-pentenyloxymethyl)androsta-5,7,16-triene 1α,3β-Bis(tert-butyldimethylsilyloxy)-17-{4-triethylsilyloxy-4-methyl-(2E)-pentenyloxymethyl}androsta-5,7,16-triene (550 mg, 0.726 mmol) and a 1M tetra-n-butylammonium fluoride tetrahydrofuran solution (7 ml) were subjected to reaction using a procedure similar to that of Example 5(2) (4 hours), worked up and purified by column chromatography (using ethyl acetate:dichloromethane=4:1 and then ethyl acetate) to give the titled compound (238 mg, 79%) as a colorless foam.

IR(neat): 3371, 2970, 2931, 2852, 1458, 1369, 1232, 1151, 1113, 1055 cm$^{-1}$.

$^1$H NMR δ: 0.85(s, 3H), 0.99(s, 3H), 1.33(s, 6H), 2.73–2.87(m, 1H), 3.78(brs, 1H), 3.89–4.14(m, 4H), 5.43–5.50(m, 1H), 5.62–5.92(m, 4H).

MS m/z: 396(M$^+$-H$_2$O), 55(100%). UV $\lambda_{max}$ nm: 271, 281, 293.

(3) Synthesis of 1α,3β-dihydroxy-17-{4-hydroxy-4-methyl-(2E)-pentenyloxymethyl}-9,10-secoandrosta-5,7,10(19),16-tetraene 1α,3β-Dihydroxy-17-{4-hydroxy-4-methyl-(2E)-pentenyloxymethyl}androsta-5,7,16-triene (210 mg, 0.507 mmol) and ethanol (200 ml) were subjected to reaction using a procedure similar to that of Example 5(3) (irradiation for 11 min. 30 sec, reflux under heating for 2 hours) and purified by preparative thin layer chromatography (4 sheets (each 0.5 mm thickness), dichloromethane:ethanol=10:1, developed twice; 2 sheets (each 0.5 mm thickness), toluene:ethyl acetate=1:1, developed three times; and 1 sheet (0.5 mm thickness), dichloromethane:ethyl acetate=1:1, developed twice) to give the titled compound (6.42 mg, 3%) as a colorless glassy substance.

IR(neat): 3370, 2970, 2929, 2848, 1446, 1367, 1211, 1147, 1111, 1055 cm$^{-1}$.

$^1$H NMR δ: 0.74(s, 3H), 1.33(s, 6H), 2.76–2.86(m, 1H), 3.97(d, J=5.6 Hz, 2H), 4.02(brs, 2H), 4.15–4.30(m, 1H), 4.39–4.49(m, 1H), 5.01(brs, 1H), 5.34(brs, 1H), 5.62(brs, 1H), 5.69–5.93(m, 2H), 6.11(d, J=11.2 Hz, 1H), 6.37(d, J=11.2 Hz, 1H).

MS m/z: 396(M$^+$-H$_2$O), 91(100%). UV $\lambda_{max}$ nm: 263.

Example 10

(1) Synthesis of 1α,3β-bis(tert-butyldimethylsilyloxy)-17-{4-ethyl-4-triethylsilyloxy-(2E)-hexenyloxymethyl}androsta-5,7,16-triene 1α,3β-Bis(tert-butyldimethylsilyloxy)-17-(hydroxymethyl)androsta-5,7,16-triene (500 mg, 0.917 mmol), 1-bromo-4-ethyl-4-triethylsilyloxy-(2E)-hexene (0.59 g, 1.83 mmol), sodium hydride (60% in oil, 0.11 g, 2.75 mmol), 15-crown-5 (0.18 ml, 0.917 mmol) and tetrahydrofuran (1.2 ml) were subjected to reaction using a procedure similar to that of Example 5(1) (2 hours) and worked up to give a mixture (540 mg) containing the titled compound.

(2) Synthesis of 17-{4-ethyl-4-hydroxy-(2E)-hexenyloxymethyl}-1α,3β-dihydroxyandrosta-5,7,16-triene The mixture (540 mg) containing the 1α,3β-bis(tert-butyldimethylsilyloxy)-17-{4-ethyl-4-triethylsilyloxy-(2E)-hexenyloxymethyl}androsta-5,7,16-triene obtained in Example 10(1) and a 1M tetra-n-butylammonium fluoride tetrahydrofuran solution (7 ml) were subjected to reaction using a procedure similar to that of Example 5(2) (3 hours), worked up and purified by column chromatography (dichloromethane:ethyl acetate=1:4) to give the titled compound (222 mg, 73%) as a white foam.

$^1$H NMR δ: 0.84(s, 3H), 0.87(t, J=7.6 Hz, 6H), 3.78(brs, 1H), 3.93–4.15(m, 5H), 5.46(brs, 1H), 5.63–5.79(m, 4H). MS m/z: 424($M^+$-$H_2O$), 57(100%).

(3) Synthesis of 17-{4-ethyl-4-hydroxy-(2E)-hexenyloxymethyl}1α,3β-dihydroxy-9,10-secoandrosta-5,7,10(19),16-tetraene 17-{4-Ethyl-4-hydroxy-(2E)-hexenyloxymethyl}-1α,3β-dihydroxyandrosta-5,7,16-triene (0.222 g, 0.502 mmol) and ethanol (200 ml) were subjected to reaction using a procedure similar to that of Example 5(3) (irradiation for 11 min. 45 sec., reflux under heating for 2 hours) and purified by preparative thin layer chromatography (10 sheets (each 0.5 mm thickness), dichloromethane:ethanol 9:1, developed once; and 5 sheets (each 0.5 mm thickness), ethyl acetate:toluene=1:1, developed three times) to give the titled compound (3.65 mg, 2%) as a colorless oil.

IR(neat): 3421, 2966, 2933, 1653, 1047 $cm^{-1}$.

$^1$H NMR δ: 0.74(s, 3H), 0.86(t, J=7.6 Hz, 6H), 4.00(brs, 2H), 4.01(brs, 2H), 4.23(brs, 1H), 4.44(brs, 1H), 5.03(s, 1H), 5.34(s, 1H), 5.62(s, 1H), 5.68–5.74(m, 2H), 6.10(d, J=11.2 Hz, 1H), 6.37(d, J=11.2 Hz, 1H).

MS m/z: 424($M^+$-$H_2O$), 57(100%). UV $λ_{max}$ nm: 264.

Example 11

(1) Synthesis of 1α,3β-bis(tert-butyldimethylsilyloxy)-17-(4-ethyl-4-triethylsilyloxy-2-hexynyloxymethyl)androsta-5,7,16-triene 1α,3β-Bis(tert-butyldimethylsilyloxy)-17-(hydroxymethyl)androsta-5,7,16-triene (1.0 g, 1.84 mmol), 1-bromo-4-ethyl-4-triethylsilyloxy-2-hexyne (1.172 g, 3.70 mmol), sodium hydride (60% in oil, 0.22 g, 5.51 mmol), 15-crown-5 (0.36 ml, 1.84 mmol) and tetrahydrofuran (2.5 ml) were subjected to reaction using a procedure similar to that of Example 5(1) (2 hours) and worked up to give a mixture (1.32 g) containing the titled compound.

(2) Synthesis of 17-(4-ethyl-4-hydroxy-2-hexynyloxymethyl)-1α,3β-dihydroxyandrosta-5,7,16-triene The mixture (1.0 g) containing the 1α,3β-bis(tert-butyldimethylsilyloxy)-17-(4-ethyl-4-triethylsilyloxy-2-hexynyloxymethyl)androsta-5,7,16-triene obtained in the above (1) and a 1M tetra-n-butylammonium fluoride tetrahydrofuran solution (12 ml) were subjected to reaction using a procedure similar to that of Example 5(2) (3 hours), worked up and purified by column chromatography (dichloromethane:ethyl acetate=1:4) to give a fraction (0.46 g) containing the titled compound.

(3) Synthesis of 17-(4-ethyl-4-hydroxy-2-hexynyloxymethyl)-1α,3β-dihydroxy-9,10-secoandrosta-5,7,10(19),16-tetraene The fraction (0.17 g) containing the 17-(4-ethyl-4-hydroxy-2-hexynyloxymethyl)-1α,3β-dihydroxyandrosta-5,7,16-triene obtained in the above (2) and ethanol (200 ml) were subjected to reaction using a procedure similar to that of Example 5(3) (irradiation for 9 min., reflux under heating for 2 hours) and purified by preparative thin layer chromatography (8 sheets (each 0.5 mm thickness), dichloromethane:ethanol=10:1, developed once; and 5 sheets (each 0.5 mm thickness), ethyl acetate:toluene=1:1, developed once) to give the titled compound (2.62 mg, 2%) as a colorless oil.

IR(neat): 3384, 2966, 2931, 1716, 1458, 1373, 1240, 1053 $cm^{-1}$. $^1$H NMR δ: 0.74(s, 3H), 1.04(t, J=7.6 Hz, 6H), 4.10(brs, 2H), 4.18(s, 2H), 4.46(brs, 1H), 5.01(s, 1H), 5.34(s, 1H), 5.65(s, 1H), 6.10(d, J=11.2 Hz, 1H), 6.37(d, J=11.2 Hz, 1H). MS m/z: 422($M^+$-$H_2O$), 57(100%). UV $λ_{max}$ nm: 261.

Example 12

Synthesis of 1α,3β-dihydroxy-20-(4-hydroxy-4-methylpentyloxy)-20-methyl-9,10-secopregna-5,7,10(19),16-tetraene 1α,3β-Bis(tert-butyldimethylsilyloxy)-20-hydroxy-20-methylpregna-5,7,16-triene (100 mg, 0.17 mmol), sodium hydride (60% in oil, 41 mg, 1.01 mmol), tetrahydrofuran (3.0 ml), 15-crown-5 (37 mg, 0.17 mmol) and 1-bromo-4-methyl-4-(triethylsilyloxy)pentane (306 mg, 1.04 mmol) were subjected to reaction using a procedure similar to that of Example 5(1), worked up and purified by preparative thin layer chromatography (4 sheets (each 1 mm thickness), hexane:toluene=1:1) to give a compound (133 mg) as white powder.

Then, the compound (196 mg), tetrahydrofuran (10.0 ml) and a 1M tetra-n-butylammonium fluoride tetrahydrofuran solution (3.8 ml) were subjected to reaction using a procedure similar to that of Example 5(2) (2 hours), worked up and purified by preparative thin layer chromatography (3 sheets (each 1.0 mm thickness), dichloromethane:ethyl acetate=2:8) to give a compound (111 mg) as a yellow oil.

Then the compound (111 mg) and ethanol (200 ml) were subjected to reaction using a procedure similar to that of Example 5(3) (irradiation for 7 min. 30 sec., reflux under heating for 2 hours) and purified by preparative thin layer chromatography (5 sheets (each 0.5 mm thickness), dichloromethane:ethanol=20:1, developed twice; 2 sheets (each 0.5 mm thickness), hexane:ethyl acetate:ethanol=3:7:0.5, developed twice; and 1 sheet (0.5 mm thickness), toluene: ethyl acetate=1:4, developed twice) to give the titled compound (7.789 mg, 7.02%, in three steps) as a colorless oil.

IR(neat): 3340, 2970, 2933, 2871, 1365, 1155, 1055 $cm^{-1}$.

$^1$H NMR δ: 0.84(s, 3H), 1.22(s, 6H), 1.34(s, 3H), 1.35(s, 3H), 2.55–2.66(m, 1H), 2.75–2.85(m, 1H), 3.23–3.34(m, 2H), 4.15–4.30(m, 1H), 4.39–4.50(m, 1H), 5.01(brs, 1H), 5.34(brs, 1H), 5.61(brs, 1H), 6.11(d, J=11.2 Hz, 1H), 6.38(d, J=11.2 Hz, 1H).

MS m/z: 326($M^+$-$HO(CH_2)_3CMe_2OH$), 59(100%). UV $λ_{max}$ nm: 266.

Example 13

(1) Synthesis of 1α,3β-bis(tert-butyldimethylsilyloxy)-20-{4-ethyl-4-(triethylsilyloxy)hexyloxy}-20-methylpregna-5,7,16-triene 1α,3β-Bis(tert-butyldimethylsilyloxy)-20-hydroxy-20-methylpregna-5,7,16-triene (100 mg, 0.175 mmol), 1-bromo-4-ethyl-4-(triethylsilyloxy)hexane (225 mg, 0.696 mmol), sodium hydride (60% in oil, 42 mg, 1.05 mmol), 15-crown-5 (38 mg, 0.173 mmol) and tetrahydrofuran (3 ml) were subjected to reaction using a procedure similar to that of Example 5(1) (reflux under heating for 3 hours), worked up and purified by column chromatography (hexane:toluene=2:1) to give the titled compound (143 mg, 100%) as a colorless solid.

IR(neat): 2954, 2935, 2879, 2856, 1458, 1375, 1254, 1151, 1066 cm$^{-1}$.

$^1$H NMR δ: 0.06(s, 3H), 0.07(s, 6H), 0.11(s, 3H), 0.56(q, J=7.6 Hz, 6H), 0.82(q, J=6.9 Hz, 6H), 0.88(s, 18H), 1.33(s, 3H), 1.34(s, 3H), 1.45(q, J=7.6 Hz, 4H), 2.78–2.90(m, 1H), 3.19(t, J=6.9 Hz, 2H), 3.71(brs, 1H), 3.97–4.14(m, 1H), 5.36–5.43(m, 1H), 5.58–5.65(m, 2H).

MS m/z: 815(M$^+$+1), 73(100%). UV λ$_{max}$ nm: 271, 282, 294.

(2) Synthesis of 1α,3β-dihydroxy-20-(4-ethyl-4-hydroxyhexyloxy)-20-methylpregna-5,7,16-triene 1α,3β-Bis(tert-butyldimethylsilyloxy)-20-{4-ethyl-4-(triethylsilyloxy)hexyloxy}-20-methylpregna-5,7,16-triene (140 mg, 0.172 mmol) and a 1M tetra-n-butylammonium fluoride tetrahydrofuran solution (3 ml) were subjected to reaction using a procedure similar to that of Example 5(2) (3 hours), worked up and purified by column chromatography (ethyl acetate) to give the titled compound (81 mg, 100%) as a colorless foam.

IR(neat): 3363, 2966, 2935, 2879, 1458, 1236, 1236, 1151, 1038 cm$^{-1}$.

$^1$H NMR δ: 0.81–0.90(m, 6H), 0.95(s, 3H), 0.98(s, 3H), 1.35(s, 3H), 1.37(s, 1H), 2.72–2.83(m, 1H), 3.25(t, J=5.9 Hz, 2H), 3.79(brs, 1H), 3.99–4.16(m, 1H), 5.43–5.50(m, 1H), 5.62–5.66(m, 1H), 5.76(brd, J=5.3 Hz, 1H).

MS m/z: 326(M$^+$-HO(CH$_2$)$_3$C(C$_2$H$_5$)$_2$OH), 57(100%). UV λ$_{max}$ nm: 271, 282, 293.

(3) Synthesis of 1α,3β-dihydroxy-20-(4-ethyl-4-hydroxyhexyloxy)-20-methyl-9,10-secopregna-5,7,10(19),16-tetraene 1α,3β-Dihydroxy-20-(4-ethyl-4-hydroxyhexyloxy)-20-methylpregna-5,7,16-triene (81 mg, 0.587 mmol) and ethanol (200 ml) were subjected to reaction using a procedure similar to that of Example 5(3) (irradiation for 5 min., reflux under heating for 2 hours) and purified by preparative thin layer chromatography (3 sheets (each 0.5 mm thickness), dichloromethane:ethanol=10:1, developed twice; and 1 sheet (0.5 mm thickness), toluene:ethyl acetate=9:11, developed three times) to give the titled compound (7.34 mg, 9%) as a colorless glassy substance.

IR(neat): 3369, 2966, 2933, 2879, 1452, 1367, 1242, 1149, 1055 cm$^{-1}$.

$^1$H NMR δ: 0.81–0.91(m, 9H), 1.34(s, 3H), 1.35(s, 1H), 2.76–2.86(m, 1H), 3.27(t, J=6.3 Hz, 2H), 4.17–4.30(m, 1H), 4.39–4.51(br, 1H), 5.01(brs, 1H), 5.34(brs, 1H), 5.60(brs, 1H), 6.11(d, J=11.2 Hz, 1H), 6.38(d, J=11.2 Hz, 1H). MS m/z: 326(M$^+$-HO(CH$_2$)$_3$C(C$_2$H$_5$)$_2$OH), 57(100%). UV λ$_{max}$ nm: 264.

Example 14

Synthesis of 1α,3β-dihydroxy-20-(5-hydroxy-5-methylhexyloxy)-20-methyl-9,10-secopregna-5,7,10(19),16-tetraene 1α,3β-bis(tert-butyldimethylsilyloxy)-20-hydroxy-20-methylpregna-5,7,16-triene (200 mg, 0.34 mmol), sodium hydride (60% in oil, 82 mg, 2.02 mmol), tetrahydrofuran (6.0 ml), 15-crown-5 (74 mg, 0.34 mmol) and 1-bromo-5-methyl-5-(triethylsilyloxy)hexane (642 mg, 2.08 mmol) were subjected to reaction using a procedure similar to that of Example 5(1), worked up and purified by preparative thin layer chromatography (5 sheets (each 1 mm thickness), hexane:toluene=1:1) to give a compound (247 mg) as a yellow oil.

Then the compound (247 mg), tetrahydrofuran (12.0 ml) and a 1M tetra-n-butylammonium fluoride tetrahydrofuran solution (4.7 ml) were subjected to reaction using a procedure similar to that of Example 5(2) (2 hours), worked up and purified by preparative thin layer chromatography (3 sheets (each 1.0 mm thickness), dichloromethane:ethyl acetate=2:8) to give a compound (92 mg) as a yellow oil.

The compound (92 mg) and ethanol (200 ml) were subjected to reaction using a procedure similar to that of Example 5(3) (irradiation for 5 min. 15 sec., reflux under heating for 2 hours) and purified by preparative thin layer chromatography (3 sheets (each 0.5 mm thickness), dichloromethane:ethanol=20:1, developed three times; and 1 sheet (0.5 mm thickness), toluene:ethyl acetate=1:4, developed three times) to give the titled compound (5.848 mg, 3.74%, in three steps) as a colorless oil.

IR(neat): 3336, 2968, 2933, 2866, 1437, 1362, 1153, 1059 cm$^{-1}$.

$^1$H NMR δ: 0.84(s, 3H), 1.21(s, 6H), 1.33(s, 3H), 1.34(s, 3H), 2.54–2.65(m, 1H), 2.75–2.84(m, 1H), 3.25(t, J=6.6 Hz, 2H), 4.17–4.30(m, 1H), 4.39–4.49(m, 1H), 5.01(brs, 1H), 5.34(brs, 1H), 5.58(brs, 1H), 6.11(d, J=11.2 Hz, 1H), 6.38(d, J=11.2 Hz, 1H).

MS m/z: 326(M$^+$-HO(CH$_2$)$_4$CMe$_2$OH), 59(100%). UV λ$_{max}$ nm: 265.

Example 15

(1) Synthesis of 1α,3β-bis(tert-butyldimethylsilyloxy)-20-(4-triethylsilyloxy-4-methyl-2-pentynyloxy)-20-methylpregna-5,7,16-triene 1α,3β-Bis(tert-Butyldimethylsilyloxy)-20-hydroxy-20-methylpregna-5,7,16-triene (100 mg, 0.175 mmol), 1-bromo-4-triethylsilyloxy-4-methyl-2-pentyne (203 mg, 0.697 mmol), sodium hydride (60% in oil, 42 mg, 1.05 mmol), 15-crown-5 (38 mg, 0.173 mmol) and tetrahydrofuran (3 ml) were reacted using a procedure similar to that of Example 5 (1) (reflux under heating for 17 hours), worked-up and purified by column chromatography (hexane:toluene=2:1) to give the titled compound (85 mg, 62%) as a colorless oil.

IR(neat): 2954, 2933, 2877, 2856, 1462, 1377, 1252, 1161, 1097, 1080, 1041, 1007 cm$^{-1}$.

$^1$H NMR δ: 0.06(s, 3H), 0.07(s, 6H), 0.11(s, 3H), 0.66(q, J=7.9 Hz, 6H), 0.89(s, 18H), 0.94(s, 3H), 0.96(t, J=7.6 Hz, 9H), 1.38(s, 3H), 1.39(s, 3H), 1.46(s, 6H), 2.78–2.89(m,

1H), 3.71(brs, 1H), 3.95(s, 2H), 3.98–4.14(m, 1H), 5.36–5.43(m, 1H), 5.61(d, J=5.6 Hz, 1H), 5.69(brs, 1H).

MS m/z: 783(M$^+$+1), 73(100%). UV $\lambda_{max}$ nm: 271, 282, 294.

(2) Synthesis of 1α,3β-dihydroxy-20-(4-hydroxy-4-methyl-2-pentynyloxy)-20-methylpregna-5,7,16-triene 1α,3β-Bis(tert-butyldimethylsilyloxy)-20-(4-triethylsilyloxy-4-methyl-2-pentynyloxy)-20-methylpregna-5,7,16-triene (82 mg, 0.105 mmol) and a 1M tetra-n-butylammonium fluoride tetrahydrofuran solution (3 ml) were subjected to reaction using a procedure similar to that of Example 5(2) (3 hours), worked up and purified by column chromatography (ethyl acetate) to give the titled compound (51 mg, quantitative) as a colorless foam.

IR(neat): 3376, 2976, 2931, 2860, 1369, 1236, 1147, 1061, 1039 cm$^{-1}$.

$^1$H NMR δ: 0.96(s, 3H), 0.98(s, 3H), 1.38(s, 3H), 1.40(s, 3H), 1.50(s, 6H), 2.71–2.85(m, 1H), 3.78(brs, 1H), 3.96(s, 2H), 4.00–4.17(m, 1H), 5.41–5.49(m, 1H), 5.66–5.78(m, 2H).

MS m/z: 440(M$^+$), 105(100%). UV $\lambda_{max}$ nm: 271, 282, 294.

(3) Synthesis of 1α,3β-dihydroxy-20-(4-hydroxy-4-methyl-2-pentynyloxy)-20-methyl-9,10-secopregna-5,7,10(19),16-tetraene 1α,3β-Dihydroxy-20-(4-hydroxy-4-methyl-2-pentynyloxy)-20-methylpregna-5,7,16-triene (48 mg, 0.109 mmol) and ethanol (200 ml) were subjected to reaction using a procedure similar to that of Example 5(3) (irradiation for 4 min. 30 sec., reflux under heating for 2 hours) and purified by preparative thin layer chromatography (2 sheets (each 0.5 mm thickness), dichloromethane:ethanol=10:1, developed twice; and 1 sheet (0.5 mm thickness), toluene:ethyl acetate=5:6, developed twice) to give the titled compound as a colorless glassy substance (0.640 mg, 1%).

IR(neat): 3378, 1462, 1362, 1240, 1144, 1066, 1030 cm$^{-1}$.

$^1$H NMR δ: 0.85(s, 3H), 1.38(brs, 6H), 1.51(s, 6H), 2.77–2.87(m, 1H), 3.97(s, 2H), 4.17–4.30(m, 1H), 4.39–4.50(br, 1H), 5.02(brs, 1H), 5.34(brs, 1H), 5.65–5.69 (m, 1H), 6.11(d, J=11.2 Hz, 1H), 6.38(d, J=11.2 Hz, 1H).

MS m/z: 326(M$^+$-HOCH$_2$CCC(CH$_3$)$_2$OH), 55(100%). UV $\lambda_{max}$ nm: 263.

Example 16

(1) Synthesis of 1α,3β-bis(tert-butyldimethylsilyloxy)-20-{4-triethylsilyloxy-4-methyl-(2E)-pentenyloxy}-20-methylpregna-5,7,16-triene 1α,3β-Bis(tert-butyldimethylsilyloxy)-20-hydroxy-20-methylpregna-5,7,16-triene (103 mg, 0.180 mmol), 1-bromo-4-triethylsilyloxy-4-methyl-(2E)-pentene (211 mg, 0.719 mmol), sodium hydride (60% in oil, 43 mg, 1.08 mmol), 15-crown-5 (40 mg, 0.182 mmol) and tetrahydrofuran (3 ml) were subjected to reaction using a procedure similar to that of Example 5(1) (reflux under heating for 6 hours), worked up and purified by column chromatography (hexane:toluene=2:1) to give the titled compound (140 mg, 99%) as a colorless solid.

IR(neat): 2954, 2927, 2877, 2856, 1458, 1375, 1254, 1149, 1109, 1084, 1041 cm$^{-1}$.

$^1$H NMR δ: 0.05(s, 3H), 0.06(s, 6H), 0.11(s, 3H), 0.50–0.63(m, 6H), 0.88(s, 18H), 1.29(brs, 3H), 1.31(s, 3H), 2.78–2.89(m, 1H), 3.68–3.74(br, 1H), 3.77(d, J=5.3 Hz, 1H), 3.96(d, J=5.3 Hz, 1H), 3.97–4.12(m, 1H), 5.37–5.43(m, 1H), 5.54–5.84(m, 4H).

MS m/z: 784(M$^+$), 73(100%). UV $\lambda_{max}$ nm: 271, 282, 294.

(2) Synthesis of 1α,3β-dihydroxy-20-{4-hydroxy-4-methyl-(2E)-pentenyloxy}-20-methylpregna-5,7,16-triene 1α,3β-Bis(tert-butyldimethylsilyloxy)-20-{4-triethylsilyloxy-4-methyl-(2E)-pentenyloxy}-20-methylpregna-5,7,16-triene (136 mg, 0.173 mmol) and a 1M tetra-n-butylammonium fluoride tetrahydrofuran solution (5 ml) were subjected to reaction using a procedure similar to that of Example 5(2) (3 hours), worked up and purified by column chromatography (ethyl acetate) to give the titled compound (74 mg, 97%) as a colorless foam.

IR(neat): 3400, 2970, 2929, 2858, 1653, 1369, 1279, 1234, 1149, 1039 cm$^{-1}$.

$^1$H NMR δ: 0.96(s, 3H), 0.98(s, 3H), 1.32(s, 6H), 1.37(s, 3H), 1.39(s, 3H), 2.73–2.82(m, 1H), 3.76–3.83(m, 3H), 4.00–4.16(m, 1H), 5.44–5.49(m, 1H), 5.66–5.88(m, 4H).

MS m/z: 424(M$^+$-H$_2$O), 59(100%). UV $\lambda_{max}$ nm: 271, 282, 294.

(3) Synthesis of 1α,3β-dihydroxy-20-{4-hydroxy-4-methyl-(2E)-pentenyloxy}-20-methyl-9,10-secopregna-5,7,10(19),16-tetraene 1α,3β-Dihydroxy-20-{4-hydroxy-4-methyl-(2E)-pentenyloxy}-20-methylpregna-5,7,16-triene (70 mg, 0.158 mmol) and ethanol (200 ml) were subjected to reaction using a procedure similar to that of Example 5(3) (irradiation for 5 min., reflux under heating for 2 hours) and purified by preparative thin layer chromatography (2 sheets (each 0.5 mm thickness), dichloromethane:ethanol=10:1, developed twice; 1 sheet (0.5 mm thickness), toluene:ethyl acetate=5:6, developed twice; and 1 sheet (0.5 mm thickness), hexane:ethyl acetate:ethanol=10:10:1, developed three times) to give the titled compound (6.80 mg, 10%) as a colorless glassy substance.

IR(neat): 3359, 2972, 2931, 2852, 1458, 1367, 1240, 1146, 1053 cm$^{-1}$.

$^1$H NMR δ: 0.85(s, 3H), 1.32(s, 6H), 1.36(s, 3H), 1.38(s, 3H), 2.75–2.87(m, 1H), 3.82(d, J=5.0 Hz, 1H), 4.19–4.30(m, 1H), 4.40–4.50(m, 1H), 5.02(brs, 1H), 5.34(brs, 1H), 5.61–5.89(m, 3H), 6.02(d, J=11.2 Hz, 1H), 6.38(d, J=11.2 Hz, 1H).

MS m/z: 424(M$^+$-H$_2$O), 59(100%). UV $\lambda_{max}$ nm: 263.

Example 17

(1) Synthesis of 1α,3β-bis(tert-butyldimethylsilyloxy)-20-{4-triethylsilyloxy-4-methyl-(2Z)-pentenyloxy}-20-ethylpregna-5,7,16-triene 1α,3β-Bis(tert-butyldimethylsilyloxy)-20-hydroxy-20-ethylpregna-5,7,16-triene (103 mg, 0.180 mmol), 1-bromo-4-triethylsilyloxy-4-methyl-(2Z)-pentene (211 mg, 0.719 mol), sodium hydride (60% in oil, 43 mg, 1.08 mmol), 15-crown-5 (40 mg, 0.182 mmol) and tetrahydrofuran (3 ml) were subjected to reaction using a procedure similar to that of Example 5(1) (reflux under heating for 1 hour), worked up and purified by column chromatography (hexane:toluene=1:1) to give the titled compound (141 mg, 100%) as a colorless solid.

IR(neat): 2956, 2931, 2877, 2856, 1462, 1375, 1254, 1169, 1097, 1066, 1041, 1007 cm$^{-1}$.

$^1$H NMR δ: 0.05(s, 3H), 0.06(s, 3H), 0.06(s, 3H), 0.10(s, 3H), 0.52–0.66(m, 6H), 0.87(s, 9H), 0.89(s, 9H), 1.30(s, 3H), 1.31(s, 3H), 2.76–2.87(m, 1H), 3.71(brs, 1H), 3.98–4.36(m, 3H), 5.29–5.44(m, 3H), 5.58–5.66(m, 2H).

MS m/z: 785(M$^+$+1), 73(100%). UV λ$_{max}$ nm: 271, 282, 294.

(2) Synthesis of 1α,3β-dihydroxy-20-{4-hydroxy-4-methyl-(2Z)-pentenyloxy}-20-methylpregna-5,7,16-triene 1α,3β-Bis(tert-butyldimethylsilyloxy)-20-{4-triethylsilyloxy-4-methyl-(2Z)-pentenyloxy}-20-methylpregna-5,7,16-triene (140 mg, 0.178 mmol) and a 1M tetra-n-butylammonium fluoride tetrahydrofuran solution (5 ml) were subjected to reaction using a procedure similar to that of Example 5(2) (4 hours), worked up and purified by column chromatography (ethyl acetate) to give the titled compound (63 mg, 80%) as a colorless foam.

IR(neat): 3377, 2972, 2931, 1460, 1369, 1236, 1149, 1039 cm$^{-1}$.

$^1$H NMR δ: 0.95(s, 3H), 0.97(s, 3H), 1.34(s, 6H), 1.41(s, 3H), 1.43(s, 3H), 2.71–2.83(m, 1H), 3.78(brs, 1H), 3.91(dd, J=12.9, 5.6 Hz, 1H), 3.99–4.17(m, 2H), 5.37–5.50(m, 2H), 5.56–5.78(m, 3H).

MS m/z:424(M$^+$-H$_2$O), 55(100%). UV λ$_{max}$ nm: 271, 282, 294.

(3) Synthesis of 1α,3β-dihydroxy-20-{4-hydroxy-4-methyl-(2Z)-pentenyloxy}-20-methyl-9,10-secopregna-5,7,10(19),16-tetraene 1α,3β-Dihydroxy-20-{4-hydroxy-4-methyl-(2Z)-pentenyloxy}-20-methylpregna-5,7,16-triene (61 mg, 0.138 mmol) and ethanol (200 ml) were subjected to reaction using a procedure similar to that of Example 5(3) (irradiation for 4 min. 45 sec., reflux under heating for 2 hours) and purified by preparative thin layer chromatography (2 sheets (each 0.5 mm thickness), dichloromethane:ethanol=10:1, developed twice; and 1 sheet (0.5 mm thickness), toluene:ethyl acetate=5:6, developed twice) to give the titled compound (2.90 mg, 5%) as a colorless glassy substance.

IR(neat): 3359, 2958, 2925, 2854, 1466, 1363, 1279, 1242, 1146, 1057 cm$^{-1}$.

$^1$H NMR δ: 0.85(s, 3H), 1.26(s, 6H), 1.34(s, 3H), 2.74–2.86(m, 1H), 3.89–4.35(m, 3H), 4.45(brs, 1H), 5.01 (brs, 1H), 5.34(brs, 1H), 5.30–5.62(m, 2H), 5.65(brs, 1H), 6.11(d, J=11.2 Hz, 1H), 6.38(d, J=11.2 Hz, 1H).

MS m/z: 424(M$^+$-H$_2$O), 55(100%). UV λ$_{max}$ nm: 264.

Example 18

(1) Synthesis of 1α,3β-bis(tert-butyldimethylsilyloxy)-20-(4-ethyl-4-triethylsilyloxy-2-hexynyloxy)-20-methylpregna-5,7,16-triene 1α,3β-Bis(tert-butyldimethylsilyloxy)-20-hydroxy-20-methylpregna-5,7,16-triene (100 mg, 0.17 mmol), 1-bromo-4-ethyl-4-triethylsilyloxy-2-hexyne (150 mg, 0.47 mmol), sodium hydride (60% in oil, 41 mg, 1.02 mmol), 15-crown-5 (37 mg, 0.17 mmol) and tetrahydrofuran (3 ml) were subjected to reaction using a procedure similar to that of Example 5(1) (at room temperature for 17 hours), worked up and purified by preparative thin layer chromatography (3 sheets (each 1.0 mm thickness), hexane:toluene=1:1) to give the titled compound (52 mg, 37.7%) as a yellow oil.

IR(neat): 2954, 2935, 2877, 2856, 1462, 1377, 1329, 1254, 1149, 1097, 1082, 1068, 1007 cm$^{-1}$.

$^1$H NMR δ: 0.06(s, 3H), 0.07(s, 6H), 0.11(s, 3H), 0.67(q, J=7.6 Hz, 6H), 0.89(s, 18H), 0.91–1.01(m, 21H), 1.38(s, 3H), 1.40(s, 3H), 2.77–2.90(m, 1H), 3.71(brs, 1H), 3.97(s, 2H), 4.00–4.14(m, 1H), 5.35–5.45(m, 1H), 5.57–5.63(m, 1H), 5.68(brs, 1H).

MS m/z: 782(M$^+$-CH$_2$CH$_3$), 73(100%). UV λ$_{max}$ nm: 271, 282, 294.

(2) Synthesis of 1α,3β-hydroxy-20-(4-ethyl-4-hydroxy-2-hexynyloxy)-20-methylpregna-5,7,16-triene 1α,3β-Bis(tert-butyldimethylsilyloxy)-20-(4-ethyl-4-triethylsilyloxy-2-hexynyloxy)-20-methylpregna-5,7,16-triene (52 mg, 0.064 mmol) and a 1M tetra-n-butylammonium fluoride tetrahydrofuran solution (0.96 ml) were subjected to reaction using a procedure similar to that of Example 5(2) (2 hours), worked up and purified by preparative thin layer chromatography (2 sheets (each 0.5 mm thickness), ethyl acetate:dichloromethane=4:1) to give the titled compound (27 mg, 90.0%) as a colorless foam.

IR(neat): 3400, 2970, 2935, 2879, 1462, 1369, 1236, 1147, 1041 cm$^{-1}$.

$^1$H NMR δ: 0.95(s, 3H), 0.97(s, 3H), 1.00(t, J=7.3 Hz, 6H), 1.38(s, 3H), 1.39(s, 3H), 2.71–2.85(m, 1H), 3.77(brs, 1H), 3.97(s, 2H), 4.00–4.14(m, 1H), 5.42–5.49(m, 1H), 5.66–5.77(m, 2H).

MS m/z: 450(M$^+$-H$_2$O), 57(100%). UV λ$_{max}$ nm: 272, 282, 294.

(3) Synthesis of 1α,3β-dihydroxy-20-(4-ethyl-4-hydroxy-2-hexynyloxy)-20-methyl-9,10-secopregna-5,7,10(19),16-tetraene 1α,3β-Hydroxy-20-(4-ethyl-4-hydroxy-2-hexynyloxy)-20-methylpregna-5,7,16-triene (27 mg, 0.058 mmol) and ethanol (200 ml) were subjected to reaction using a procedure similar to that of Example 5(3) (irradiation for 4 min., reflux under heating for 2 hours) and purified by preparative thin layer chromatography (2 sheets (each 0.5 mm thickness), dichloromethane:ethanol=20:1, developed three times; 2 sheets (each 0.5 mm thickness), toluene:ethyl acetate=1:4, developed three times; and 1 sheet (0.5 mm thickness), toluene:ethyl acetate=1, developed 1.5 times) to give the titled compound (1.635 mg, 6.1%) as a colorless oil.

IR(neat): 3390, 2966, 2925, 2850, 1732, 1462, 1379, 1288, 1144, 1047 cm$^{-1}$.

$^1$H NMR δ: 0.86(s, 3H), 1.02(t, J=7.6 Hz, 6H), 1.38(s, 6H), 2.56–2.66(m, 1H), 2.76–2.86(m, 1H), 4.00(s, 2H), 4.19–4.31(m, 1H), 4.40–4.50(m, 1H), 5.02(brs, 1H), 5.34 (brs, 1H), 5.66(brs, 1H), 6.11(d, J=11.5 Hz, 1H), 6.38(d, J=11.2 Hz, 1H).

MS m/z: 450(M$^+$-H$_2$O), 57(100%). UV λ$_{max}$ nm: 264.

Example 19

(1) Synthesis of 1α,3β-bis(tert-butyldimethylsilyloxy)-20-{4-ethyl-4-triethylsilyloxy-(2Z)-hexenyloxy}-20-methylpregna-5,7,16-triene 1α,3β-Bis(tert-butyldimethylsilyloxy)-20-hydroxy-20-methylpregna-5,7,16-triene (100 mg, 0.175 mmol), 1-bromo-4-ethyl-4-triethylsilyloxy-(2Z)-hexene (224 mg, 0.697 mmol), sodium hydride (60% in oil, 42 mg, 1.05 mmol), 15-crown-5 (38 mg, 0.173 mmol) and tetrahydrofuran (3 ml) were subjected to reaction using a procedure similar to that of Example 5(1) (reflux under heating for 17 hours), worked up and purified by column chromatography (hexane:toluene=2:1) to give the titled compound (102 mg, 72%) as a colorless solid.

IR(neat): 2956, 2931, 2877, 2856, 1462, 1375, 1360, 1254, 1151, 1097, 1080 cm$^{-1}$.

$^1$H NMR δ: 0.05(s, 3H), 0.06(s, 3H), 0.06(s, 3H), 0.10(s, 3H), 0.60(q, J=7.9 Hz, 6H), 0.87(s, 9H), 0.88(s, 9H), 1.35(s, 3H), 1.37(s, 3H), 2.75–2.88(m, 1H), 3.71(brs, 1H), 3.97–4.36(m, 3H), 5.03–5.11(m, 1H), 5.36–5.50(m, 2H), 5.58–5.67(m, 2H).

MS m/z: 813(M$^+$+1), 73(100%). UV λ$_{max}$ nm: 271, 282, 294.

(2) Synthesis of 20-{4-ethyl-4-hydroxy-(2Z)-hexenyloxy}-1α,3β-dihydroxy-20-methylpregna-5,7,16-triene 1α,3β-Bis(tert-butyldimethylsilyloxy)-20-{4-ethyl-4-triethylsilyloxy-(2Z)-hexenyloxy}-20-methylpregna-5,7,16-triene (99 mg, 0.122 mmol) and a 1M tetra-n-butylammonium fluoride tetrahydrofuran solution (5 ml) were subjected to reaction using a procedure similar to that of Example 5(2) (3 hours), worked up and purified by column chromatography (ethyl acetate) to give the titled compound (52 mg, 91%) as a colorless glassy substance.

IR(neat): 3400, 2968, 2933, 2877, 1458, 1369, 1151, 1041 cm$^{-1}$.

$^1$H NMR δ: 0.85–0.94(m, 6H), 0.95(s, 3H), 0.97(s, 3H), 1.39(s, 3H), 1.41(s, 3H), 2.70–2.83(m, 1H), 3.87(dd, J=12.5, 6.3 Hz, 1H), 4.00–4.16(m, 2H), 4.32–5.42(m, 1H), 5.42–5.49(m, 1H), 5.53–5.79(m, 3H).

MS m/z: 452(M$^+$-H$_2$O), 326(100%). UV λ$_{max}$ nm: 271, 282, 294.

(3) Synthesis of 20-{4-ethyl-4-hydroxy-(2Z)-hexenyloxy}-1α,3β-dihydroxy-20-methyl-9,10-secopregna-5,7,10(19),16-tetraene 20-{4-Ethyl-4-hydroxy-(2Z)-hexenyloxy}-1α,3β-dihydroxy-20-methylpregna-5,7,16-triene (51 mg, 0.108 mmol) and ethanol (200 ml) were subjected to reaction using a procedure similar to that of Example 5(3) (irradiation for 4 min. 30 sec., reflux under heating for 2 hours) and purified by preparative thin layer chromatography (2 sheets (each 0.5 mm thickness), dichloromethane:ethanol=10:1, developed twice; and 1 sheet (0.5 mm thickness), toluene:ethyl acetate=5:6, developed twice) to give the titled compound (1.69 mg, 3%) as a colorless glassy substance.

IR(neat): 2966, 2929, 2877, 2850, 1462, 1442, 1377, 1145, 1050 cm$^{-1}$.

$^1$H NMR δ: 0.85(s, 3H), 0.86–0.94(m, 6H), 1.39(s, 3H), 1.39(s, 3H), 2.74–2.85(m, 1H), 3.86–4.10(m, 2H), 4.19–4.29(br, 1H), 4.40–4.49(br, 1H), 5.01(brs, 1H), 5.32–5.72(m, 4H), 6.11(d, J=11.2 Hz, 1H), 6.38(d, J=11.2 Hz, 1H).

MS m/z: 470(M$^+$), 57(100%). UV λ$_{max}$ nm: 263.

Example 20

(1) Synthesis of 1α,3β-bis(tert-butyldimethylsilyloxy)-20-{4-ethyl-4-triethylsilyloxy-(2E)-hexenyloxy}-20-methylpregna-5,7,16-triene 1α,3β-Bis(tert-butyldimethylsilyloxy)-20-hydroxy-20-methylpregna-5,7,16-triene (400 mg, 0.698 mmol), 1-bromo-4-ethyl-4-triethylsilyloxy-(2E)-hexene (0.897 g, 2.79 mmol), sodium hydride (60% in oil, 0.168 g, 4.188 mmol), 15-crown-5 (0.14 ml, 0.698 mmol) and tetrahydrofuran (12 ml) were subjected to reaction using a procedure similar to that of Example 5(1) (3 hours), worked up and purified by column chromatography (hexane:toluene=2:1) to give the titled compound (0.35 g, 62%) as a yellow foam.

$^1$H NMR δ: 0.05(s, 3H), 0.07(s, 3H), 0.10(s, 3H), 0.11(s, 3H), 0.57(q, J=7.3 Hz, 6H), 0.81(t, J=7.6 Hz, 6H), 0.88(s, 9H), 0.89(s, 9H), 1.36(s, 3H), 1.37(s, 3H), 2.84(brs, 1H), 3.71(brs, 1H), 3.77–3.84(m, 2H), 4.05(brs, 1H), 5.40(brs, 1H), 5.57–5.66(m, 4H).

(2) Synthesis of 20-{4-ethyl-4-hydroxy-(2E)-hexenyloxy}-1α,3β-dihydroxy-20-methylpregna-5,7,16-triene 1α,3β-Bis(tert-butyldimethylsilyloxy)-20-{4-ethyl-4-triethylsilyloxy-(2E)-hexenyloxy}-20-methylpregna-5,7,16-triene (350 mg, 0.430 mmol) and a 1M tetra-n-butylammonium fluoride tetrahydrofuran solution (15 ml) were subjected to reaction using a procedure similar to that of Example 5(2) (3 hours), worked up and purified by column chromatography (ethyl acetate) to give the titled compound (200 mg, 100%) as a yellow foam.

$^1$H NMR δ: 0.86(t, J=5.6 Hz, 6H), 0.95(s, 3H), 0.98(s, 3H), 1.37(s, 3H), 1.39(s, 3H), 3.73–3.86(m, 3H), 4.10(m, 1H), 5.46(m, 1H), 5.61–5.78(m, 4H).

(3) Synthesis of 20-{4-ethyl-4-hydroxy-(2E)-hexenyloxy}-1α,3β-dihydroxy-20-methyl-9,10-secopregna-5,7,10(19),16-tetraene 20-{4-Ethyl-4-hydroxy-(2E)-hexenyloxy}-1α,3β-dihydroxy-20-methylpregna-5,7,16-triene (0.125 g, 0.266 mmol) and ethanol (200 ml) were subjected to reaction using a procedure similar to that of Example 5(3) (irradiation for 6 min., reflux under heating for 2 hours) and purified by preparative thin layer chromatography (1 sheet (0.5 mm thickness), dichloromethane:ethanol=10:1, developed once; and 1 sheet (0.5 mm thickness), ethyl acetate:toluene=1:1, developed twice) to give the titled compound (14.4 mg, 12%) as a colorless oil.

IR(neat): 3566, 2970, 2933, 1489, 1377, 1146, 1053 cm$^{-1}$.

$^1$H NMR δ: 0.85(t, J=10.8 Hz, 6H), 0.86(s, 3H), 1.36(s, 3H), 1.37(s, 3H), 3.84–3.85(m, 2H), 4.24(brs, 1H), 4.43(brs, 1H), 5.01(s, 1H), 5.34(s, 1H), 5.63–5.71(m, 3H), 6.11(d, J=11.5 Hz, 1H), 6.38(d, J=11.5 Hz, 1H).

MS m/z: 452(M$^+$-H$_2$O), 133(100%). UV λ$_{max}$ nm: 264.

Example 21

(1) Synthesis of 1α,3β-bis(tert-butyldimethylsilyloxy)-20-(2-hydroxy-2-methylpropoxy)-20-methylpregna-5,7,16-triene A solution of 1α,3β-bis(tert-butyldimethylsilyloxy)-20-hydroxy-20-methylpregna-5,7,16-triene (49.2 mg, 0.0859 mmol), potassium hydride (35% in oil, 0.1 ml, 0.873 mmol) and dibenzo-18-crown-6 (30 mg, 0.0832 mmol) in toluene (0.2 ml) was stirred at room temperature for 3 min., 1,2-epoxy-2-methylpropane (60 mg, 0.832 mmol) was added and stirred at external temperature of 45° C. for 1.5 hours.

The reaction solution was cooled with ice and water was added. The mixture was diluted with ethyl acetate, washed with saturated brine and the organic layer was dried over anhydrous magnesium sulfate. After evaporating under reduced pressure to remove the solvent, the thus obtained residue was purified by preparative thin layer chromatography (2 sheets (each 0.5 mm thickness), hexane:ethyl acetate=15:1, developed twice) to give the titled compound (10.4 mg, 19%) and 1α,3β-bis(tert-butyldimethylsilyloxy)-20-hydroxy-20-methylpregna-5,7,16-triene (18.6 mg, 38%), each as a colorless oil.

IR(neat): 3400, 2932, 2896, 2856, 1462, 1360, 1254, 1078, 836, 1774 cm$^{-1}$.

$^1$H NMR δ: 0.05(s, 3H), 0.06(s, 6H) 0.11(s, 3H), 0.88(s, 18H), 0.94(s, 3H), 0.95(s, 3H), 1.18(s, 3H), 1.19(s, 3H), 1.34(s, 3H), 1.37 (s, 3H), 1.87–1.99(m, 1H), 2.78–2.89(m, 1H), 3.07(d, J=8.5 Hz, 1H), 3.10(d, J=8.5 Hz, 1H), 3.72(brs, 1H), 3.98–4.12(m, 1H), 5.36–5.44(m, 1H), 5.57–5.66(m, 2H).

MS m/z: 644(M$^+$), 73(100%). UV λ$_{max}$ nm: 271, 282, 294.

(2) Synthesis of 1α,3β-dihydroxy-20-(2-hydroxy-2-methylpropoxy)-20-methylpregna-5,7,16-triene 1α,3β-Bis(tert-butyldimethylsilyloxy)-20-(2-hydroxy-2-methylpropoxy)-20-methylpregna-5,7,16-triene (35.6 mg, 0.0552 mmol), a 1M tetra-n-butylammonium fluoride tetrahydrofuran solution (0.35 ml) and tetrahydrofuran (0.5 ml) were subjected to reaction using a procedure similar to that of Example 5(2) (reflux under heating for 12 hours), worked up and the thus obtained residue was purified by preparative thin layer chromatography (1 sheet (0.5 mm thickness), dichloromethane:ethanol=15:1, developed three times) to give the titled compound (18.1 mg, 79%) as a colorless oil.

IR(neat): 3396, 2972, 2932, 1462, 1376, 1238, 1152, 1080 cm$^{-1}$.

$^1$H NMR δ: 0.96(s, 3H), 0.98(s, 6H), 1.19(s, 6H), 1.34(s, 3H), 1.38(s, 3H), 2.49–2.61(m, 1H), 2.70–2.84(m, 1H), 3.07(d, J=8.8 Hz, 1H), 3.11(d, J=8.8 Hz, 1H), 3.77(brs, 1H), 4.00–4.18(m, 1H), 5.41–5.50(m, 1H), 5.64(brs, 1H) 5.71–5.79(m, 1H).

MS m/z: 416(M$^+$), 59(100%). UV λ$_{max}$ nm: 271, 282, 294.

(3) Synthesis of 1α,3β-dihydroxy-20-(2-hydroxy-2-methylpropoxy)-20-methyl-9,10-secopregna-5,7,10(19),16-tetraene 1α,3β-Dihydroxy-20-(2-hydroxy-2-methylpropoxy)-20-methylpregna-5,7,16-triene (24.3 mg, 0.0583 mmol) and ethanol (200 ml) were subjected to reaction using a procedure similar to that of Example 5(3) (irradiation for 2.5 min., reflux under heating for 2 hours) and purified by preparative thin layer chromatography (1 sheet (0.5 mm thickness), dichloromethane:ethanol=15:1, developed three times; 1 sheet (0.25 mm thickness), hexane:ethyl acetate:ethanol=10:5:1, developed three times; and 1 sheet (0.25 mm thickness), dichloromethane:ethyl acetate=3:1, developed three times) to give the titled compound (1.199 mg, 5%) as a colorless foam.

IR(neat): 3356, 2968, 2932, 1434, 1360, 1240, 1150, 1074, 914 cm$^{-1}$.

$^1$H NMR δ: 0.85(s, 3H), 1.20(s, 6H), 1.34(s, 3H), 1.36(s, 3H), 2.56–2.68(m, 1H), 2.75–2.88(m, 1H), 3.10(s, 2H), 4.18–4.30(m, 1H), 4.39–4.50(m, 1H), 5.01(s, 1H), 5.34(s, 1H), 5.61(s, 1H), 6.11(d, J=11.2 Hz, 1H), 6.50(d, J=11.2 Hz, 1H).

MS m/z: 326(M$^+$-HOCH$_2$C(CH$_3$)$_2$OH), 59(100%). UV λ$_{max}$ nm: 264.

Example 22

(1) Synthesis of 1α,3β-bis(tert-butyldimethylsilyloxy)-20-(2-ethyl-2-hydroxybutoxy)-20-methylpregna-5,7,16-triene 1α,3β-Bis(tert-butyldimethylsilyloxy)-20-hydroxy-20-methylpregna-5,7,16-triene (261.4 mg, 0.456 mmol), potassium hydride (35% in oil, 0.53 ml, 4.625 mmol), dibenzo-18-crown-6 (165 mg, 0.458 mmol), toluene (0.75 ml) and 1,2-epoxy-2-ethylbutane (450 mg, 4.493 mmol) were subjected to reaction using a procedure similar to that of Example 21(1) (at external temperature of 95° C. for 2 hours and 10 min.), worked up and the thus obtained residue was purified by column chromatography (hexane:ethyl acetate=10:1) and preparative thin layer chromatography (1 sheet (0.5 mm thickness), hexane:ethyl acetate=20:1, developed twice) to give the titled compound (32.0 mg, 10%) and 1α,3β-bis(tert-butyldimethylsilyloxy)-20-hydroxy-20-methylpregna-5,7,16-triene (138.5 mg, 53%), each as a colorless oil.

IR(neat): 3336, 2932, 2888, 1462, 1254, 1084, 836, 774 cm$^{-1}$.

$^1$H NMR δ: 0.05(s, 3H), 0.06(s, 6H) 0.10(s, 3H), 0.85(t, J=7.7 Hz, 6H), 0.88(s, 9H), 0.89(s, 9H), 0.92(s, 3H), 0.94(s, 3H), 1.34(s, 3H), 1.36(s, 3H), 1.50(q, J=7.7 Hz, 4H), 2.78–2.90(m, 1H), 3.11(s, 2H), 3.70(brs, 1H), 3.95–4.12(m, 1H), 5.35–5.44(m, 1H), 5.57–5.65(m, 1H), 5.63(brs, 1H).

MS m/z: 554(M$^+$-HOCH$_2$C(CH$_2$CH$_3$)$_2$OH), 73(100%). UV λ$_{max}$ nm: 271, 282, 293.

(2) Synthesis of 20-(2-ethyl-2-hydroxybutoxy)-1α,3β-dihydroxy-20-methylpregna-5,7,16-triene 1α,3β-Bis(tert-butyldimethylsilyloxy)-20-(2-ethyl-2-hydroxybutoxy)-20-methylpregna-5,7,16-triene (32.0 mg, 0.0475 mmol), a 1M tetra-n-butylammonium fluoride tetrahydrofuran solution (0.3 ml, 0.3 mmol) and tetrahydrofuran (0.5 ml) were subjected to reaction using a procedure similar to that of Example 5(2) (reflux under heating for 16 hours), worked up and the thus obtained residue was purified by preparative thin layer chromatography (1 sheet (0.5 mm thickness), hexane:ethyl acetate:ethanol=10:5:1, developed twice) to give the titled compound (19.8 mg, 94%) as a colorless oil.

IR(neat): 3400, 2964, 2932, 1460, 1376, 1274, 1136, 1072, 1040, 736 cm$^{-1}$.

$^1$H NMR δ: 0.84(t, J=7.3 Hz, 3H), 0.86(t, J=7.3 Hz, 3H), 0.95(s, 3H), 0.96(s, 3H), 1.34(s, 3H), 1.37(s, 3H), 1.48(q, J=7.3 Hz, 4H), 2.46–2.62(m, 1H), 2.70–2.88(m, 1H), 3.09(d, J=8.7 Hz, 1H), 3.14(d, J=8.7 Hz, 1H), 3.76(brs, 1H), 3.98–4.14(m, 3H), 5.40–5.53(m, 1H), 5.64(brs, 1H), 5.70–5.82(m, 1H).

MS m/z: 326(M$^+$-HOCH$_2$C(CH$_2$CH$_3$)$_2$OH), 87(100%). UV λ$_{max}$ nm: 271, 282, 294.

(3) Synthesis of 20-(2-ethyl-2-hydroxypropoxy)-1α, 3β-dihydroxy-20-methyl-9,10-secopregna-5,7,10(19),16-tetraene 20-(2-Ethyl-2-hydroxybutoxy)-1α,3β-dihydroxy-20-methylpregna-5,7,16-triene (19.8 mg, 0.0445 mmol) and ethanol (200 ml) were subjected to reaction using a procedure similar to that of Example 5(3) (irradiation for 2 min. 15 sec., reflux under heating for 2 hours) and purified by preparative thin layer chromatography (1 sheet (0.25 mm thickness), dichloromethane:ethanol=15:1, developed twice; and 1 sheet (0.25 mm thickness), dichloromethane:ethyl acetate=3:1, developed three times) to give the titled compound (1.150 mg, 6%) as a colorless foam.

IR(neat): 3368, 2928, 1460, 1376, 1244, 1056, 912 cm$^{-1}$.
$^1$H NMR δ: 0.84(s, 3H), 0.82–0.92(m, 6H), 1.33(s, 3H), 1.35(s, 3H), 1.44–1.63(m, 4H), 2.55–2.66(m, 1H), 2.74–2.85(m, 1H), 3.12(s, 2H), 4.19–4.30(m, 1H), 4.39–4.59(m, 1H), 5.01(s, H), 5.33(s, 1H), 5.59(s, 1H), 6.10(d, J=11.5 Hz, 1H), 6.38(d, J=11.5 Hz, 1H).
MS m/z: 326(M$^+$-HOCH$_2$C(CH$_2$CH$_3$)$_2$OH), 87(100%). UV λ$_{max}$ nm: 264.

Example 23

(1) Synthesis of 1α,3β-bis(tert-butyldimethylsilyloxy)-17-(2,3-epoxy-3-methylbutoxymethyl)androsta-5,7,16-triene A solution of 1α,3β-bis(tert-butyldimethylsilyloxy)-17-(hydroxymethyl)androsta-5,7,16-triene (51.6 mg, 0.0947 mmol), sodium hydride (95%, 21.1 mg, 0.879 mmol) and 1-bromo-2,3-epoxy-3-methylbutane (91.2 mg, 0.553 mmol) in tetrahydrofuran (1 ml) was stirred at room temperature for 20 min. and refluxed under heating for 20 min. The reaction solution was diluted with ethyl acetate and washed with water and saturated brine. The organic layer was dried over anhydrous magnesium sulfate, evaporated under reduced pressure to remove the solvent, and the thus obtained residue was purified by preparative thin layer chromatography (1 sheet (0.5 mm thickness), hexane:ethyl acetate=10:1, developed twice) to give the titled compound (48.3 mg, 81%) as a pale yellow oil.

IR(neat): 3036, 2928, 2856, 1460, 1376, 1252, 1068, 832, 774 cm$^{-1}$.
$^1$H NMR δ: 0.05(s, 3H), 0.06(s, 6H), 0.11(s, 3H), 0.84(s, 3H), 0.88(s, 18H), 0.94(s, 3H), 1.29(s, 3H), 1.34(s, 3H), 2.81–2.91(m, 1H), 2.97(t, J=5.4 Hz, 1H), 3.45–3.57(m, 1H), 3.63(dd, J=5.0, 11.1 Hz, 1H), 3.70(brs, 1H), 3.96–4.20(m, 3H), 5.35–5.43(m, 1H), 5.60(d, J=5.4 Hz, 1H), 5.68(brs, 1H). UV λ$_{max}$ nm: 269, 281, 293.

(2) Synthesis of 1α,3β-bis(tert-butyldimethylsilyloxy)-17-(3-hydroxy-3-methylbutoxymethyl)androsta-5,7,16-triene At room temperature, a solution of 1.0M L-SELECTRIDE in tetrahydrofuran (0.25 ml, 0.25 mmol) was added to a solution of 1α,3β-bis(tert-butyldimethylsilyloxy)-17-(2,3-epoxy-3-methylbutoxymethyl)androsta-5,7,16-triene (48.3 mg, 0.0768 mmol) in tetrahydrofuran (2 ml) and stirred at the same temperature for 1 hour. To the solution, was further added a solution of 1.0M L-SELECTRIDE in tetrahydrofuran (0.2 ml, 0.2 mmol), followed by stirring at the same temperature for 1 hour. After cooling the reaction solution with ice, a 3N aqueous sodium hydroxide solution and then hydrogen peroxide solution were added. Immediately after the addition, the mixture was diluted with ethyl acetate and washed with water and saturated brine. The organic layer was dried over anhydrous magnesium sulfate and evaporated to remove the solvent under reduced pressure; the thus obtained residue was purified by preparative thin layer chromatography (1 sheet (0.5 mm thickness), hexane:ethyl acetate=10:1, developed twice) to give the titled compound (42.0 mg, 87%) as a colorless oil.

IR(neat): 3500, 3036, 2952, 2856, 1462, 1372, 1254, 1096, 838, 772 cm$^{-1}$.
$^1$H NMR δ: 0.05(s, 3H), 0.06(s, 6H), 0.10(s, 3H), 0.83(s, 3H), 0.87(s, 9H), 0.88(s, 9H), 0.94(s, 3H), 1.25(s, 6H), 1.77(t, J=5.9 Hz, 2H), 2.79–2.91(m, 1H), 3.60–3.75(m, 3H), 3.94–4.12(m, 3H), 5.35–5.44(m, 1H), 5.60(d, J=5.4 Hz, 1H), 5.63(brs, 1H).
MS m/z: 630(M$^+$), 73(100%). UV λ$_{max}$ nm: 269, 281, 293.

(3) Synthesis of 1α,3β-dihydroxy-17-(3-hydroxy-3-methylbutoxymethyl)androsta-5,7,16-triene 1α,3β-Bis(tert-butyldimethylsilyloxy)-17-(3-hydroxy-3-methylbutoxymethyl)androsta-5,7,16-triene (40.0 mg, 0.0634 mmol) and a 1M tetra-n-butylammonium fluoride tetrahydrofuran solution (0.4 ml, 0.4 mmol) were subjected to reaction using a procedure similar to that of Example 5(2) (reflux under heating for 1 hour), worked up and the thus obtained residue was purified by preparative thin layer chromatography (dichloromethane:ethanol=10:1, developed once) to give the titled compound (20.9 mg, 82%) as a colorless oil.

IR(neat): 3392, 2968, 2932, 1460, 1370, 1154, 1056, 732 cm$^{-1}$.
$^1$H NMR δ: 0.83(s, 3H), 0.96(s, 3H), 1.24(s, 6H), 2.46–2.59(m, 1H), 2.73–2.86(m, $_1$H), 3.60–3.73(m, 2H), 3.76(brs, 1H), 3.99(d, J=12.9 Hz, 1H), 4.06(d, J=12.9 Hz, 1H), 5.39–5.48(m, 1H), 5.64(s, 1H), 5.67–5.76(m, 1H).
MS m/z: 401(M$^+$-1), 298(100%), UV λ$_{max}$ nm: 270, 282, 293.

(4) Synthesis of 1α,3β-dihydroxy-17-(3-hydroxy-3-methylbutoxymethyl)-9,10-secoandrosta-5,7,10(19),16-tetraene 1α,3β-Dihydroxy-17-(3-hydroxy-3-methylbutoxymethyl)androsta-5,7,16-triene (20.0 mg, 0.0497 mmol) and ethanol (200 ml) were subjected to reaction using a procedure similar to that of Example 5(3) (irradiation for 2 min. 15 sec., reflux under heating for 1.5 hours) and purified by preparative thin layer chromatography (1 sheet (0.25 mm thickness), dichloromethane:ethanol=10:1, developed twice; and 1 sheet (0.25 mm thickness), hexane:ethyl acetate: ethanol=10:5:1, developed twice) to give the titled compound (2.135 mg, 11%) as a colorless oil.

IR(neat): 3376, 2928, 1452, 1368, 1056, 960, 800, 728 cm$^{-1}$.
$^1$H NMR δ: 0.73(s, 3H), 1.25(s, 6H), 1.78(t, J=5.9 Hz, 2H), 2.53–2.68(m, 1H), 2.74–2.87(m, 1H), 3.35(s, 1H), 3.59–3.77(m, 2H), 3.97(d, J=13.7 Hz, 1H), 4.04(d, J=13.7 Hz, 1H), 4.17–4.30(m, 1H), 4.38–4.51(m, 1H), 5.01(s, 1H), 5.33(s, 1H), 5.60(s, 1H), 6.09(d, J=11.2 Hz, 1H), 6.37(d, J=11.2 Hz, 1H).
MS m/z: 298(M$^+$-HOCH$_2$CH$_2$C(CH$_3$)$_2$OH), 59(100%). UV λ$_{max}$ nm: 264.

Example 24

(1) Synthesis of 1α,3β-bis(tert-butyldimethylsilyloxy)-20-(3-hydroxy-3-methylbutoxy)-20-methyl-pregna-5,7,16-triene A solution of 1α,3β-bis(tert-butyldimethylsilyloxy)-20-hydroxy-20-methylpregna-5,7,16-triene (67.7 mg, 0.118 mmol), sodium hydride (60% in oil, 40.0 mg, 1.00 mmol) and 1-bromo-2,3-epoxy-3-methylbutane (100 mg, 0.606 mmol) in tetrahydrofuran (1 ml) was refluxed under heating for 1.5 hours. To the thus obtained reaction solution, was added 1.0M L-SELECTRIDE/tetrahydrofuran solution (1.2 ml, 1.2 mmol) at room temperature, followed by stirring at the same temperature for 12 hours. After cooling the reaction solution with ice, a 3N aqueous sodium hydroxide solution and then hydrogen peroxide solution were added to the reaction solution. Immediately after the addition, the mixture was diluted with ethyl acetate and washed with water and saturated brine. The organic layer was dried over anhydrous magnesium sulfate and evaporated to remove the solvent under reduced pressure; the thus obtained residue was purified by preparative thin layer chromatography (2 sheets (each 0.5 mm thickness), hexane:ethyl acetate=15:1, developed once) to give the titled compound (72.5 mg, 93%) as a colorless oil.

IR(neat): 3528, 2952, 2932, 2888, 2856, 1462, 1374, 1360, 1254, 1150, 1080, 968, 834, 774 cm$^{-1}$.

$^1$H NMR δ: 0.05(s, 3H), 0.06(s, 3H), 0.07(s, 3H), 0.10(s, 3H), 0.88(s, 21H), 0.93(s, 3H), 1.21(s, 3H), 1.22(s, 3H), 1.37(s, 6H), 2.75–2.89(m, 1H), 3.37–3.49(m, 1H), 3.49–3.61(s, 1H), 3.70(brs, 1H), 3.81(brs, 1H), 3.95–4.13 (m, 1H), 5.35–5.44(m, 1H), 5.60(d, J=5.4 Hz, 1H), 5.66(brs, 1H).

MS m/z: 658(M$^+$), 73(100%). UV $\lambda_{max}$ nm: 271, 282, 294.

(2) Synthesis of 1α,3β-hydroxy-20-(3-hydroxy-3-methylbutoxy)-20-methylpregna-5,7,16-triene 1α,3β-Bis(tert-butyldimethylsilyloxy)-20-(3-hydroxy-3-methylbutoxy)-20-methylpregna-5,7,16-triene (98.0 mg, 0.149 mmol), a 1M tetra-n-butylammonium fluoride tetrahydrofuran solution (1.0 ml, 1.0 mmol) and tetrahydrofuran (1 ml) were subjected to reaction using a procedure similar to that of Example 5(2) (reflux under heating for 4.5 hours), worked up and the thus obtained residue was purified by preparative thin layer chromatography (1 sheet (0.5 mm thickness), dichloromethane:ethanol=15:1, developed twice) to give the titled compound (52.9 mg, 83%) as a colorless oil.

IR(neat): 3408, 2968, 2932, 1462, 1378, 1148, 1056, 1040, 910, 732 cm$^{-1}$.

$^1$H NMR δ: 0.93(s, 3H), 0.96(s, 3H), 1.21(s, 3H), 1.22(s, 3H), 1.37(s, 3H), 1.38(s, 3H), 2.46–2.59(m, 1H), 2.71–2.84 (m, 1H), 3.39–3.50(m, 1H), 3.50–3.62(m, 1H), 3.77(brs, 1H), 3.98–4.16(m, 2H), 5.38–5.50(m, 1H), 5.66(s, 1H), 5.69–5.76(m, 1H).

MS m/z: 371(M$^+$-C(CH$_3$)$_2$OH), 326(100%). UV $\lambda_{max}$ nm: 271, 282, 294.

(3) Synthesis of 1α,3β-dihydroxy-20-(3-hydroxy-3-methylbutoxy)-20-methyl-9,10-secopregna-5,7,10(19),16-tetraene 1α,3β-Hydroxy-20-(3-hydroxy-3-methylbutoxy)-20-methylpregna-5,7,16-triene (52 mg, 0.121 mmol) and ethanol (200 ml) were subjected to reaction using a procedure similar to that of Example 5(3) (irradiation for 4.5 min., reflux under heating for 2 hours) and purified by preparative thin layer chromatography (1 sheet (0.5 mm thickness), dichloromethane:ethanol=20:1, developed twice, and dichloromethane:ethanol=15:1, developed twice; 1 sheet (0.25 mm thickness), hexane:ethyl acetate:ethanol=10:5:1, developed three times; and 1 sheet (0.25 mm thickness), dichloromethane:ethyl acetate=3:1, developed twice, dichloromethane:ethyl acetate=2:1, developed once and dichloromethane:ethyl acetate=1:1, developed once) to give the titled compound (2.903 mg, 6%) as a colorless foam.

IR(neat): 3392, 2968, 2932, 1438, 1364, 1146, 1060, 908, 732 cm$^{-1}$.

$^1$H NMR δ: 0.84(s, 3H), 1.23(s, 3H), 1.24(s, 3H), 1.36(s, 3H), 1.38(s, 3H), 2.53–2.68(m, 1H), 2.74–2.88(m, 1H), 3.40–3.53(m, 2H), 3.53–3.64(m, 1H), 4.16–4.30(m, 1H), 4.38–4.51(m, 1H), 5.01(s, 1H), 5.34(s, 1H), 5.64(s, 1H), 6.10(d, J=11.3 Hz, 1H), 6.38(d, J=11.3 Hz, 1H).

MS m/z: 326(M$^+$-HOCH$_2$CH$_2$C(CH$_3$)$_2$OH), 59(100%). UV $\lambda_{max}$ nm: 263.

Example 25

(1) Synthesis of 1α,3β-bis(tert-butyldimethylsilyloxy)-17-(N,N-dimethylaminocarbonylethoxymethyl)androsta-5,7,16-triene To a solution of 1α,3β-bis(tert-butyldimethylsilyloxy)-17-hydroxymethylandrosta-5,7,16-triene (951 mg, 1.75 mmol) in tetrahydrofuran (17.5 ml), was added sodium hydride (60% in oil, 105 mg, 2.62 mmol), followed by stirring under nitrogen stream at room temperature for 30 min. After adding N,N-dimethylacrylamide (540 mg, 5.44 mmol), the solution was stirred at 5° C. for 14 hours, poured into a saturated aqueous ammonium chloride solution, extracted with ethyl acetate (3 times) and washed with saturated brine and water. The organic layer was dried over anhydrous magnesium sulfate and evaporated to remove the solvent under reduced pressure; the thus obtained residue was purified by column chromatography (hexane:ethyl acetate 2:1) to give the titled compound (1.05 g, 92.7%) as a yellow oil.

IR(neat): 2954, 2929, 2895, 2856, 1653, 1462, 1398, 1371, 1254, 1097, 1074 cm$^{-1}$.

$^1$H NMR δ: 0.05(s, 3H), 0.06(s, 6H), 0.11(s, 3H), 0.82(s, 3H), 0.877(s, 9H), 0.881(s, 9H), 0.94(s, 3H), 2.62(t, J=6.6 Hz, 2H), 2.80–2.90(m, 1H), 2.94(s, 3H), 3.02(s, 3H), 3.70 (brs, 1H), 3.76(t, J=6.6Hz, 2H), 3.96–4.12(m, 4H), 5.34–5.42(m, 1H), 5.55–5.67(m, 2H).

MS m/z: 644(M$^+$–1), 73(100%). UV $\lambda_{max}$ nm: 271, 281, 293.

(2) Synthesis of 1α,3β-bis(tert-butyldimethylsilyloxy)-17-(3-ethyl-3-hydroxypentyloxymethyl)androsta-5,7,16-triene Tetrahydrofuran (11 ml) was mixed with anhydrous cerous (III) chloride (2.33 g, 9.46 mmol), stirred under nitrogen stream at room temperature for 30 min., cooled with ice, mixed with ethylmagnesium bromide (0.96 mol/l, 9.0 ml, 8.6 mmol) and stirred for 30 min. The reaction solution was mixed with a solution of 1α,3β-bis(tert-butyldimethylsilyloxy)-17-(N,N-dimethylaminocarbonylethoxymethyl)androsta-5,7,16-triene (553 mg, 0.86 mmol) in tetrahydrofuran (11 ml) at 0° C., followed by stirring for 1 hour at the same temperature. The reaction solution was poured into a saturated aqueous ammonium chloride solution, extracted with ethyl acetate (3 times), washed with saturated brine and water, dried over anhydrous magnesium sulfate and evaporated under reduced pressure to remove solvent, giving a reaction mixture containing a ketone body. The thus obtained mixture was again subjected to the same reaction and worked up; the thus obtained residue was purified by column chromatography (hexane:ethyl acetate=5:1) to give the titled compound (317 mg, 56.0%) as a yellow oil.

IR(neat): 3681, 2956, 2929, 2883, 2856, 1471, 1462, 1371, 1362, 1255, 1097, 1070 cm$^{-1}$.

$^1$H NMR δ: 0.05(s, 3H), 0.06(s, 6H), 0.11(s, 3H), 0.78–0.96(m, 30H), 2.79–2.92(m, 1H), 3.56–3.74(m, 1H), 3.93–4.11(m, 3H), 5.33–5.43(m, 1H), 5.55–5.66(m, 2H).

MS m/z: 658(M$^+$–1), 73(100%). UV $\lambda_{max}$ nm: 271, 281, 294.

(3) Synthesis of 1α,3β-dihydroxy-17-(3-ethyl-3-hydroxypentyloxymethyl)androsta-5,7,16-triene α,3β-Bis(tert-butyldimethylsilyloxy)-17-(3-ethyl-3-hydroxypentyloxymethyl)androsta-5,7,16-triene (377 mg, 0.57 mmol), a 1M tetra-n-butylammonium fluoride tetrahydrofuran solution (5.7 ml) and tetrahydrofuran (2.2 ml) were subjected to reaction using a procedure similar to that of Example 5(2) (2 hours), worked up and purified by preparative thin layer chromatography (4 sheets (each 1.0 mm thickness), ethyl acetate:dichloromethane=4:1) to give the titled compound (213 mg, 86.9%) as a brown foam.

IR(neat): 3400, 2964, 2937, 2879, 1460, 1371, 1271, 1142, 1061 cm$^{-1}$.

$^1$H NMR δ: 0.81–0.91(m, 9H), 0.98(s, 3H), 2.48–2.62(m, 1H), 2.72–2.87(m, 1H), 3.60–3.70(m, 2H), 3.78(brs, 1H), 3.95–4.15(m, 3H), 5.41–5.49(m, 1H), 5.64(brs, 1H), 5.71–5.77(m, 1H). MS m/z: 298(M$^+$-HO(CH$_2$)$_2$CEt$_2$OH), 57(100%). UV $\lambda_{max}$ nm: 271, 281, 294.

(4) Synthesis of 1α,3β-dihydroxy-17-(3-ethyl-3-hydroxypentyloxymethyl)-9,10-secoandrosta-5,7,10 (19),16-tetraene 1α,3β-Dihydroxy-17-(3-ethyl-3-hydroxypentyloxymethyl)androsta-5,7,16-triene (213 mg, 4.88 mmol) and ethanol (200 ml) were subjected to reaction using a procedure similar to that of Example 5(3) (irradiation for 11 min. 15 sec., reflux under heating for 2 hours) and purified by preparative thin layer chromatography (5 sheets (each 0.5 mm thickness), dichloromethane:ethanol=20:1, developed three times; and 2 sheets (each 0.5 mm thickness), hexane: ethyl acetate:ethanol=3:7:0.5, developed three times) to give the titled compound (24.798 mg, 11.6%) as a colorless oil.

IR(neat): 3400, 3035, 2964, 2879, 2850, 1460, 1450, 1369, 1092, 1061 cm$^{-1}$.

$^1$H NMR δ: 0.72(s, 3H), 0.86(t, J=7.6 Hz, 6H), 2.53–2.64 (m, 1H), 2.74–2.85(m, 1H), 3.58–3.67(m, 2H), 3.92–4.06 (m, 2H), 4.15–4.28(m, 1H), 4.37–4.48(m, 1H), 5.00(brs, 1H), 5.33(brs, 1H), 5.59(brs, 1H), 6.09(d, J=11.2 Hz, 1H), 6.35(d, J=10.9 Hz, 1H).

MS m/z: 298(M$^+$-HO(CH$_2$)$_2$CEt$_2$OH), 134(100%). UV $\lambda_{max}$ nm: 265.

Example 26

(1) Synthesis of 1α,3β-bis(tert-butyldimethylsilyloxy)-20-(N,N-dimethylaminocarbonylethoxy)-20-methylpregna-5,7,16-triene 1α,3β-Bis(tert-butyldimethylsilyloxy)-20-hydroxy-20-methylpregna-5,7,16-triene (200 mg, 0.36 mmol), N,N-dimethylacrylamide (107 mg, 1.08 mmol), sodium hydride (60% in oil, 23 mg, 0.56 mmol) and tetrahydrofuran (4 ml) were subjected to reaction using a procedure similar to that of Example 25(1) (17 hours at room temperature), worked up and purified by preparative thin layer chromatography (4 sheets (each 1.0 mm thickness), ethyl acetate) to give the titled compound (114 mg, 47.1%) as white powder.

IR(neat): 2954, 2929, 2884, 2856, 1651, 1462, 1414, 1252, 1151, 1084, 1063 cm$^{-1}$.

$^1$H NMR δ: 0.01–0.08(m, 9H), 0.10(s, 3H), 0.85–0.91(m, 2H), 0.87(s, 9H), 0.88(s, 9H), 0.93(s, 6H), 1.35(s, 6H), 2.46–2.63(m, 2H), 2.76–2.88(m, 1H), 2.92(s, 3H), 3.00(s, 3H), 3.46–3.68(m, 2H), 3.70(brs, 1H), 3.95–4.11(m, 1H), 5.34–5.43(m, 1H), 5.56–5.68(m, 2H).

MS m/z: 554(M$^+$–1–HO(CH$_2$)$_2$CONMe$_2$), 73(100%). UV $\lambda_{max}$ nm: 271, 282, 294.

(2) Synthesis of 1α,3β-bis(tert-butyldimethylsilyloxy)-20-(3-ethyl-3-hydroxypentyloxy)-20-methylpregna-5,7,16-triene 1α,3β-Bis(tert-butyldimethylsilyloxy)-20-(N,N-dimethylaminocarbonylethoxy)-20-methylpregna-5,7,16-triene (133 mg, 0.20 mmol), anhydrous cerous (III) chloride (2.17 g, 8.8 mmol), ethylmagnesium bromide (8.3 ml, 8.0 mmol) and tetrahydrofuran (10 ml) were subjected to reaction using a procedure similar to that of Example 25(2) (at 0° C. for 1 hour), worked up and purified by preparative thin layer chromatography (2 sheets (each 1.0 mm thickness), hexane: ethyl acetate=5:1) to give the titled compound (70.7 mg, 51.7%) as a colorless oil.

IR(neat): 3509, 2956, 2929, 2883, 2856, 1462, 1375, 1254, 1149, 1097, 1066 cm$^{-1}$.

$^1$H NMR δ: 0.05(s, 3H), 0.06(s, 3H), 0.07(s, 3H), 0.11(s, 3H), 0.79–0.98(m, 30H), 1.36(s, 6H), 2.77–2.89(m, 1H), 3.35–3.46(m, 1H), 3.47–3.56(m, 1H), 3.71(brs, 1H), 3.96–4.12(m, 1H), 5.37–5.43(m, 1H), 5.57–5.63(m, 1H), 5.66(brs, 1H).

MS m/z: 555(M$^+$-HOCH$_2$CH$_2$CEt$_2$OH), 73(100%). UV $\lambda_{max}$ nm: 271, 282, 294.

(3) Synthesis of 1α,3β-dihydroxy-20-(3-ethyl-3-hydroxypentyloxy)-20-methylpregna-5,7,16-triene 1α,3β-Bis(tert-butyldimethylsilyloxy)-20-(3-ethyl-3-hydroxypentyloxy)-20-methylpregna-5,7,16-triene (85 mg, 0.12 mmol), a 1M tetra-n-butylammonium fluoride tetrahydrofuran solution (1.2 ml) and tetrahydrofuran (4.6 ml) were subjected to reaction using a procedure similar to that of Example 5(2) (3 hours), worked up and purified by preparative thin layer chromatography (3 sheets (each 0.5 mm thickness), ethyl acetate:dichloromethane=4:1) to give the titled compound (55 mg, 100%) as a colorless oil.

IR(neat): 3399, 2968, 2935, 2879, 1653, 1458, 1377, 1149, 1061 cm$^{-1}$.

$^1$H NMR δ: 0.78–0.89(m, 6H), 0.93(s, 3H), 0.95(s, 3H), 1.36(s, 3H), 1.37(s, 3H), 2.71–2.84(m, 1H), 3.36–3.58(m,

2H), 3.76(brs, 1H), 3.97–4.14(m, 1H), 5.40–5.47(m, 1H), 5.65(brs, 1H), 5.68–5.75(m, 1H).

MS m/z: 344($M^+$-$CH_2CH_2CEt_2OH$), 326(100%). UV $\lambda_{max}$ nm: 271, 282, 294.

(4) Synthesis of 1α,3β-dihydroxy-20-(3-ethyl-3-hydroxypentyloxy)-20-methyl-9,10-secopregna-5,7,10(19),16-tetraene 1α,3β-Dihydroxy-20-(3-ethyl-3-hydroxypentyloxy)-20-methylpregna-5,7,16-triene (55 mg, 0.12 mmol) and ethanol (200 ml) were subjected to reaction using a procedure similar to that of Example 5(3) (irradiation for 4 min. 45 sec., reflux under heating for 2 hours) and purified by preparative thin layer chromatography (2 sheets (each 0.5 mm thickness), dichloromethane:ethanol=20:1, developed three times; 2 sheets (each 0.5 mm thickness), toluene:ethyl acetate=1:4, developed three times; and 2 sheets (each 0.25 mm thickness), toluene:ethyl acetate=1:1, developed twice) to give the titled compound (2.759 mg, 5.02%) as a colorless oil.

IR(neat): 3390, 2964, 2927, 2879, 2852, 1728, 1462, 1377, 1360 $cm^{-1}$.

$^1$H NMR δ: 0.81–0.92(m, 9H), 1.36(s, 3H), 1.37(s, 3H), 2.56–2.66(m, 1H), 2.76–2.86(m, 1H), 3.39–3.57(m, 2H), 4.19–4.30(m, 1H), 4.39–4.50(m, 1H), 5.01(brs, 1H), 5.34 (brs, 1H), 5.63(brs, 1H), 6.11(d, J=11.2 Hz, 1H), 6.38(d, J=11.2 Hz, 1H).

MS m/z: 343($M^+$-$(CH_2)_2CEt_2OH$), 57(100%). UV $\lambda_{max}$ nm: 265.

Example 27

(1) Synthesis of 1α,3β-bis(tert-butyldimethylsilyloxy)-17-(tert-butoxycarbonylmethoxymethyl)androsta-5,7,16-triene A solution of 1α,3β-bis(tert-butyldimethylsilyloxy)-17-(hydroxymethyl)androsta-5,7,16-triene (1.0 g, 1.84 mmol), sodium hydride (60% in oil, 220 mg, 5.50 mmol), 15-crown-5 (400 mg, 1.82 mmol) and t-butyl bromoacetate (0.55 ml, 3.69 mmol) in tetrahydrofuran (20 ml) was refluxed under heating for 1 hour and 15 min. The reaction solution was diluted with ethyl acetate and filtered with CELITE. Under cooling with ice, water was added dropwise to the filtrate which was then washed with saturated brine. The organic layer was dried over anhydrous magnesium sulfate, evaporated under reduced pressure to remove the solvent and the thus obtained residue was purified by column chromatography (hexane:ethyl acetate=20:1) to give the titled compound (946.6 mg, 78%) as a colorless oil.

IR(neat): 2952, 2928, 2892, 2856, 1748, 1460, 1370, 1252, 1098, 968, 834, 774 $cm^{-1}$.

$^1$H NMR δ: 0.05(s, 3H), 0.06(s, 6H), 0.11(s, 3H), 0.84(s, 3H), 0.88(s, 18H), 0.94(s, 3H), 1.48(s, 9H), 2.79–2.92(m, 1H), 3.70(brs, 1H), 3.95(s, 2H), 4.13(s, 2H), 3.97–4.20(m, 1H), 5.35–5.43(m, 1H), 5.60(d, J=5.4 Hz, 1H), 5.69(s, 1H).

MS m/z: 526($M^+$-$HOCH_2CO_2C(CH_3)_3$), 57(100%). UV $\lambda_{max}$ nm: 271, 281, 294.

(2) Synthesis of 1α,3β-bis(tert-butyldimethylsilyloxy)-17-(2-hydroxy-2-methylpropoxymethyl)androsta-5,7,16-triene To a solution of 1α,3β-bis(tert-butyldimethylsilyloxy)-17-(tert-butoxycarbonylmethoxymethyl)androsta-5,7,16-triene (175 mg, 0.266 mmol) in tetrahydrofuran (4 ml), was added dropwise a 0.93M methylmagnesium bromide/tetrahydrofuran solution (3 ml, 2.79 mmol) at external temperature of −30° C., followed by stirring at the same temperature for 1 hour and 30 min. At the same temperature, a saturated aqueous ammonium chloride solution was added to the reaction solution, which was then warmed to room temperature and stirred for 10 min. Water was added to the reaction solution, which was then extracted with ethyl acetate. The organic layer was washed with a saturated aqueous sodium bicarbonate solution and saturated brine, dried over anhydrous magnesium sulfate and evaporated to remove the solvent under reduced pressure; the thus obtained residue was purified by preparative thin layer chromatography (3 sheets (each 0.5 mm thickness), hexane:ethyl acetate=20:1, developed twice, hexane:ethyl acetate=15:1, developed twice, and hexane:ethyl acetate 10:1, developed once) to give the titled compound (115.3 mg, 70%) as a colorless oil.

IR(neat): 3400, 2952, 2928, 2892, 2856, 1462, 1372, 1254, 1096, 912, 834, 774 $cm^{-1}$.

$^1$H NMR δ: 0.05(s, 3H), 0.06(s, 6H), 0.11(s, 3H), 0.84(s, 3H), 0.88(s, 18H), 0.95(s, 3H), 1.21(s, 6H), 2.79–2.93(m, 1H), 3.26(d, J=8.8 Hz, 1H), 3.29(d, J=8.8 Hz, 1H), 3.70(brs, 1H), 3.96–4.17(m, 3H), 5.36–5.44(m, 1H), 5.61(d, J=5.4 Hz, 1H), 5.65(brs, 1H).

MS m/z: 616($M^+$), 73(100%). UV $\lambda_{max}$ nm: 271, 281, 294.

(3) Synthesis of 1α,3β-dihydroxy-17-(2-hydroxy-2-methylpropoxymethyl)androsta-5,7,16-triene 1α,30β-Bis(tert-butyldimethylsilyloxy)-17-(2-hydroxy-2-methylpropoxymethyl)androsta-5,7,16-triene (115 mg, 0.186 mmol), a 1M tetra-n-butylammonium fluoride tetrahydrofuran solution (1.2 ml, 1.2 mmol) and tetrahydrofuran (2.5 ml) were subjected to reaction using a procedure similar to that of Example 5(2) (14 hours), worked up and the thus obtained residue was purified by preparative thin layer chromatography (1 sheet (0.5 mm thickness), dichloromethane:ethanol=15:1, developed three times) to give the titled compound (52.7 mg, 73%) as a colorless oil.

IR(neat): 3416, 2932, 1452, 1372, 1240, 1084, 912, 734 $cm^{-1}$.

$^1$H NMR δ: 0.84(s, 3H), 0.98(s, 3H), 1.21(s, 6H), 2.46–2.61(m, 1H), 2.71–2.86(m, 1H), 3.23(d, J=8.7 Hz, 1H), 3.28(d, J=8.7 Hz, 1H), 3.77(brs, 1H), 3.97–4.18(m, 3H), 5.40–5.55(m, 1H), 5.65(s, 1H), 5.69–5.78(m, 1H).

MS m/z: 389($M^+$+1), 59(100%). UV $\lambda_{max}$ nm: 271, 281, 293.

(4) Synthesis of 1α,3β-dihydroxy-17-(2-hydroxy-2-methylpropoxymethyl)-9,10-secoandrosta-5,7,10(19),16-tetraene 1α,3β-Dihydroxy-17-(2-hydroxy-2-methylpropoxymethyl)androsta-5,7,16-triene (63.0 mg, 0.162 mmol) and ethanol (200 ml) were subjected to reaction using a procedure similar to that of Example 5(3) (irradiation for 6 min. 30 sec., reflux under heating for 1.5 hours) and purified by preparative thin layer chromatography (1 sheet (0.5 mm thickness), dichloromethane:ethanol=15:1, developed three times; 1 sheet (0.25 mm thickness), toluene:ethyl acetate=5:6, developed twice, and toluene:ethyl acetate=2:3, developed once; and 1 sheet (0.25 mm thickness), hexane:ethyl acetate:ethanol=10:5:1, developed three times) to give the titled compound (3.761 mg, 6%) as a colorless foam.

IR(neat): 3368, 2928, 1444, 1368, 1106, 1060, 912, 732 cm$^{-1}$.

$^1$H NMR δ: 0.74(s, 3H), 1.21(s, 3H), 2.54–2.67(m, 1H), 2.75–2.89(m, 1H), 3.23(d, J=8.8 Hz, 1H), 3.28(d, J=8.8 Hz, 1H), 3.96–4.17(m, 2H), 4.17–4.30(m, 2H), 4.37–4.51(m, 1H), 5.01(s, 1H), 5.34(s, 1H), 5.61(s, 1H), 6.10(d, J=11.2 Hz, 1H), 6.37(d, J=11.2 Hz, 1H).

MS m/z: 298(M$^+$-HOCH$_2$C(CH$_3$)$_2$OH), 59(100%). UV λ$_{max}$ nm: 263.

Example 28

(1) Synthesis of 1α,3β-bis(tert-butyldimethylsilyloxy)-17-(2-ethyl-2-hydroxybutoxymethyl)androsta-5,7,16-triene A solution of 1α,3β-bis(tert-butyldimethylsilyloxy)-17-(tert-butoxycarbonylmethoxymethyl)androsta-5,7,16-triene (175 mg, 0.266 mmol) in tetrahydrofuran (4 ml) was subjected to reaction with a 0.96M ethylmagnesium bromide/tetrahydrofuran solution (3 ml, 2.88 mmol) using a procedure similar to that of Example 27(2) (external temperature of −30° C. for 1.5 hours), worked up and purified by preparative thin layer chromatography (3 sheets (each 0.5 mm thickness), hexane:ethyl acetate=20:1, developed twice, hexane:ethyl acetate=15:1, developed twice, and hexane:ethyl acetate=10:1, developed once) to give the titled compound (139.5 mg, 81%) as a colorless oil.

IR(neat): 3480, 2952, 2856, 1462, 1372, 1252, 1072, 968, 836, 774 cm$^{-1}$.

$^1$H NMR δ: 0.05(s, 3H), 0.07(s, 6H), 0.11(s, 3H), 0.84(s, 3H), 0.88(s, 18H), 0.95(s, 3H), 1.52(q, J=7.3 Hz, 4H), 2.77–2.92(m, 1H), 3.26(d, J=9.1 Hz, 1H), 3.32(d, J=9.1 Hz, 1H), 3.71(brs, 1H), 3.94–4.17(m, 3H), 5.35–5.44(m, 1H), 5.61(d, J=5.6 Hz, 1H), 5.64(brs, 1H).

MS m/z: 644(M$^+$), 455(100%). UV λ$_{max}$ nm: 271, 281, 294.

(2) Synthesis of 17-(2-ethyl-2-hydroxybutoxymethyl)-1α,3β-dihydroxyandrosta-5,7,16-triene 1α,3β-Bis(tert-butyldimethylsilyloxy)-17-{2-ethyl-2-hydroxybutoxymethyl}androsta-5,7,16-triene (139 mg, 0.216 mmol), a 1M tetra-n-butylammonium fluoride tetrahydrofuran solution (1.3 ml, 1.3 mmol) and tetrahydrofuran (3 ml) were subjected to reaction using a procedure similar to that of Example 5(2) (4 hours), worked up and the thus obtained residue was purified by preparative thin layer chromatography (1 sheet (0.5 mm thickness), dichloromethane:ethanol=10:1, developed three times) to give the titled compound (64.4 mg, 72%) as a colorless oil.

IR(neat): 3388, 2968, 2932, 1462, 1370, 1058, 946, 736 cm$^{-1}$.

$^1$H NMR δ: 0.83(s, 3H), 0.87(t, J=7.4 Hz, 6H), 0.98(s, 3H), 1.52(q, J=7.4 Hz, 4H), 2.48–2.62(m, 1H), 2.76–2.87(m, 1H), 3.26(d, J=9.1 Hz, 1H), 3.32(d, J=9.1 Hz, 1H), 3.78(brs, 1H), 4.00–4.23(m, 3H), 5.40–5.52(m, 1H), 5.64(s, 1H), 5.70–5.77(m, 1H).

MS m/z: 416(M$^+$), 87(100%). UV λ$_{max}$ nm: 271, 281, 293.

(3) Synthesis of 17-(2-ethyl-2-hydroxybutoxymethyl)-1α,3β-dihydroxy-9,10-secoandrosta-5,7,10(19),16-tetraene 17-(2-Ethyl-2-hydroxybutoxymethyl)-1α,3β-dihydroxyandrosta-5,7,16-triene (89 mg, 0.214 mmol) and ethanol (200 ml) were subjected to reaction using a procedure similar to that of Example 5(3) (irradiation for 9 min., reflux under heating for 1.5 hours) and purified by preparative thin layer chromatography (1 sheet (0.5 mm thickness), dichloromethane:ethanol=15:1, developed three times; 1 sheet (0.25 mm thickness), toluene:ethyl acetate=5:6, developed twice, and toluene:ethyl acetate=2:3, developed once; and 1 sheet (0.25 mm thickness), hexane:ethyl acetate:ethanol=10:5:1, developed three times) to give the titled compound (4.941 mg, 6%) as a colorless foam.

IR(neat): 3375, 2928, 1454, 1342, 1056, 912, 730 cm$^{-1}$.

$^1$H NMR δ: 0.73(s, 3H), 0.87(s, 3H), 0.87(t, J=7.5 Hz, 6H), 1.52(q, J=7.5 Hz, 4H), 2.53–2.68(m, 1H), 2.75–2.90(m, 1H), 3.26(d, J=9.0 Hz, 1H), 3.31(d, J=9.0 Hz, 1H), 3.92–4.15(m, 2H), 4.17–4.32(m, 1H), 4.37–4.52(m, 1H), 5.01(s, 1H), 5.34(s, 1H), 5.60(s, 1H), 6.10(d, J=11.2 Hz, 1H), 6.37(d, J=11.2 Hz, 1H).

MS m/z: 298(M$^+$-HOCH$_2$C(CH$_2$CH$_3$)$_2$OH), 87(100%). UV λ$_{max}$ nm: 262.

Example 29

(1) Synthesis of 1α,3β-dihydroxy-17-{4-hydroxy-4-methyl-(2Z)-pentenyloxymethyl}androsta-5,7,16-triene 1α,3β-Dihydroxy-17-(4-hydroxy-4-methyl-2-pentynyloxymethyl)androsta-5,7,16-triene (78 mg, 0.189 mmol), quinoline (12.3 mg, 0.0952 mmol), 5% palladium/barium sulfate (16 mg) and methanol (5 ml) were stirred at room temperature for 2 hours under a hydrogen atmosphere. The reaction mixture was filtered, evaporated for remove the solvent and purified by column chromatography (dichloromethane:methanol=20:1) to give the titled compound (61 mg, 78%) as a colorless glassy substance.

IR(neat): 3369, 2970, 2929, 2852, 1458, 1369, 1173, 1151, 1080, 1055 cm$^{-1}$.

$^1$H NMR δ: 0.84(s, 3H), 0.98(s, 3H), 1.34(s, 6H), 2.73–2.85(m, 1H), 3.50–3.58(br, 1H), 3.75–3.81(br, 1H), 3.99–4.26(m, 5H), 5.42–5.52(m, 2H), 5.63(brs, 1H), 5.68(brs, 1H), 5.74(brd, J=5.9 Hz, 1H).

MS m/z: 396(M$^+$-H$_2$O), 55(100%). UV λ$_{max}$ nm: 271, 281, 293.

(2) Synthesis of 1α,3β-dihydroxy-17-{4-hydroxy-4-methyl-(2Z)-pentenyloxymethyl}-9,10-secoandrosta-5,7,10(19),16-tetraene 1α,3β-Dihydroxy-17-{4-hydroxy-4-methyl-(2Z)-pentenyloxymethyl}androsta-5,7,16-triene (60 mg, 0.145 mmol) and ethanol (200 ml) were subjected to reaction using a procedure similar to that of Example 5(3) (irradiation for 4 min. 45 sec., reflux under heating for 2 hours) and purified by preparative thin layer chromatography (2 sheets (each 0.5 mm thickness), dichloromethane:ethanol=10:1, developed twice; and 1 sheet (0.5 mm thickness), toluene:ethyl acetate 1:1, developed twice) to give the titled compound (4.00 mg, 7%) as a colorless glassy substance.

IR(neat): 3363, 2968, 2929, 2850, 1435, 1369, 1173, 1057 cm$^{-1}$.

$^1$H NMR δ: 0.74(s, 3H), 1.34(s, 6H), 2.75–2.87(m, 1H), 3.99–4.28(m, 5H), 4.39–4.49(br, 1H), 5.01(brs, 1H), 5.34(brs, 1H), 5.41–5.70(m, 3H), 6.10(d, J=11.2 Hz, 1H), 6.36(d, J=11.2 Hz, 1H).

MS m/z: 396(M$^+$-H$_2$O), 55(100%). UV λ$_{max}$ nm: 263.

Example 30

(1) Synthesis of 17-{4-ethyl-4-hydroxy-(2Z)-hexenyloxymethyl}-1α,3β-dihydroxyandrosta-5,7,16-triene The fraction (0.3 g) containing 17-(4-ethyl-4-hydroxy-2-hexynyloxymethyl)-1α,3β-dihydroxyandrosta-5,7,16-triene obtained in Example 11 (2), 5% palladium/barium sulfate (0.3 g), quinoline (0.03 ml, 0.2538 mmol) and methanol (6.8 ml) were subjected to reaction using a procedure similar to that of Example 29(1) (4 hours) and worked up to give a mixture (0.80 mg) containing the targeted compound.

(2) Synthesis of 17-{4-ethyl-4-hydroxy-(2Z)-hexenyloxymethyl}-1α,3β-dihydroxy-9,10-secoandrosta-5,7,10(19),16-tetraene Ethanol (200 ml) and the mixture (0.80 mg) containing 17-{4-ethyl-4-hydroxy-(2Z)-hexenyloxymethyl}-1α,3β-dihydroxyandrosta-5,7,16-triene obtained in the above (1) were subjected to reaction using a procedure similar to that of Example 5(3) (irradiation for 4 min. 45 sec., reflux under heating for 2 hours) and purified by preparative thin layer chromatography (4 sheets (each 0.5 mm thickness), dichloromethane:ethanol=9:1, developed once; and 4 sheets (each 0.5 mm thickness), ethyl acetate:toluene=1:1, developed once) to give the titled compound (3.41 mg, 4%) as a colorless oil.

IR(neat): 3566, 2854, 1458, 1257 cm$^{-1}$. $^1$H NMR δ: 0.73(s, 3H), 0.90(t, J=7.3 Hz, 6H), 4.04(brs, 2H), 4.18–4.28 (m, 3H), 4.44(brs, 1H), 5.01(s, 1H), 5.33(s, 1H), 5.41–5.67 (m, 3H), 6.09(d, J=11.6 Hz, 1H), 6.37(d, J=11.6 Hz, 1H). MS m/z: 424(M$^+$-H$_2$O), 57(100%). UV λ$_{max}$ nm: 264.

Example 31

(1) Synthesis of 1α,3β-bis(tert-butyldimethylsilyloxy)-17-{4-ethyl-4-(triethylsilyloxy)hexylthiomethyl}androsta-5,7,16-triene To a solution of 17-acetylthiomethyl-1α,3β-bis(tert-butyldimethylsilyloxy)androsta-5,7,16-triene (274 mg, 0.454 mmol) and 1-bromo-4-ethyl-4-(triethylsilyloxy)hexane (294 mg, 0.909 mmol) in tetrahydrofuran (2 ml), was added a 1M potassium hydroxide methanol solution (3 ml) under a nitrogen atmosphere, followed by stirring at room temperature for 5 min. The thus obtained reaction mixture was partitioned by adding ethyl acetate and water. The organic layer was washed with saturated brine, dried over anhydrous sodium sulfate and evaporated to remove the solvent under reduced pressure. The thus obtained residue was purified by column chromatography (hexane:toluene=6:1) to give the titled compound (333 mg, 91%) as a colorless oil.

IR(neat): 2954, 2929, 2879, 2856, 1462, 1371, 1254, 1099, 1072 cm$^{-1}$.

$^1$H NMR δ: 0.06(s, 3H), 0.07(s, 6H), 0.11(s, 3H), 0.57(q, J=7.9 Hz, 6H), 0.88(s, 18H), 0.95(t, J=7.9 Hz, 9H), 1.45(q, J=7.6 Hz, 4H), 2.78–2.91(m, 1H), 3.19(s, 2H), 3.71(brs, 1H), 3.97–4.13(m, 1H), 5.35–5.43(m, 1H), 5.54–5.56(m, 2H).

MS m/z: 803(M$^+$+1), 73(100%). UV λ$_{max}$ nm: 271, 281, 294.

(2) Synthesis of 17-(4-ethyl-4-hydroxyhexylthiomethyl)-1α,3β-dihydroxyandrosta-5,7,16-triene 1α,3β-Bis(tert-butyldimethylsilyloxy)-17-{4-ethyl-4-(triethylsilyloxy)hexylthiomethyl}androsta-5,7,16-triene (310 mg, 0.386 mmol) and a 1M tetra-n-butylammonium fluoride tetrahydrofuran solution (5 ml) were subjected to reaction using a procedure similar to that of Example 5(2) (3 hours), worked up and purified by column chromatography (ethyl acetate) to give the titled compound (136 mg, 77%) as a colorless foam.

IR(neat): 3370, 2964, 2935, 2879, 2850, 1458, 1369, 1196, 1109, 1053, 1032 cm$^{-1}$.

$^1$H NMR δ: 0.86(t, J=7.3 Hz, 6H), 0.99(s, 3H), 1.47(q, J=7.3 Hz, 4H), 2.73–2.86(m, 1H), 3.12–3.27(m, 2H), 3.79 (brs, 1H), 4.01–4.16(m, 1H), 5.43–5.49(m, 1H), 5.58(s, 1H), 5.75(dd, J=5.6, 1.7 Hz, 1H).

MS m/z: 460(M$^+$), 143(100%). UV λ$_{max}$ nm: 271, 281, 293.

(3) Synthesis of 17-(4-ethyl-4-hydroxyhexylthiomethyl)-1α,3β-dihydroxy-9,10-secoandrosta-5,7,10(19),16-tetraene 17-(4-Ethyl-4-hydroxyhexylthiomethyl)-1α,3β-dihydroxyandrosta-5,7,16-triene (130 mg, 0.282 mmol) and ethanol (200 ml) were subjected to reaction using a procedure similar to that of Example 5(3) (irradiation for 7 min., reflux under heating for 2 hours) and purified by preparative thin layer chromatography (3 sheets (each 0.5 mm thickness), dichloromethane:ethanol=10:1, developed twice; and 2 sheets (each 0.5 mm thickness), toluene:ethyl acetate=5:6, developed twice) to give the titled compound (6.52 mg, 5%) as a colorless foam.

IR(neat): 3350, 2962, 2929, 2879, 2846, 1456, 1367, 1338, 1055 cm$^{-1}$.

$^1$H NMR δ: 0.75(s, 3H), 0.86(t, J=7.6 Hz, 6H), 1.47(q, J=7.6 Hz, 4H), 2.74–2.89(m, 1H), 3.10–3.25(m, 2H), 4.19–4.29(m, 1H), 4.40–4.50(m, 1H), 5.01(brs, 1H), 5.34 (brs, 1H), 5.54(brs, 1H), 6.10(d, J=11.2 Hz, 1H), 6.37(d, J=11.2 Hz, 1H).

MS m/z: 442(M$^+$-H$_2$O), 57(100%). UV λ$_{max}$ nm: 263.

Example 32

(1) Synthesis of 1α,3β-bis(tert-butyldimethylsilyloxy)-17-{5-(triethylsilyloxy)-5-methylhexylthiomethyl}androsta-5,7,16-triene 17-Acetylthiomethyl-1α,3β-bis(tert-butyldimethylsilyloxy)androsta-5,7,16-triene (262 mg, 0.434 mmol), 1-bromo-5-triethylsilyloxy-5-methylhexane (266 mg, 0.860 mmol), a 1M potassium hydroxide methanol solution (3 ml) and tetrahydrofuran (2 ml) were subjected to reaction using a procedure similar to that of Example 31(1) (3 hours at room temperature), worked up and purified by column chromatography (hexane:toluene=4:1) to give the titled compound (320 mg, 93%) as a colorless oil.

IR(neat): 2954, 2931, 2856, 1458, 1363, 1254, 1099, 1072, 1053 cm$^{-1}$.

$^1$H NMR δ: 0.05(s, 6H), 0.07(s, 6H), 0.11(s, 3H), 0.56(q, J=7.9 Hz, 6H), 0.88(s, 18H), 1.19(s, 6H), 2.80–2.91(m, 1H), 3.19(s, 2H), 3.71(brs, 1H), 3.97–4.11(m, 1H), 5.36–5.42(m, 1H), 5.56–5.63(m, 2H).

MS m/z: 788(M$^+$+1), 73(100%). UV λ$_{max}$ nm: 271, 282, 294.

(2) Synthesis of 1α,3β-dihydroxy-17-(5-hydroxy-5-methylhexylthiomethyl)androsta-5,7,16-triene 1α,3β-Bis(tert-butyldimethylsilyloxy)-17-(5-triethylsilyloxy-5-methylhexylthiomethyl)androsta-5,7,16-triene (313 mg, 0.396 mmol) and a 1M tetra-n-butylammonium fluoride tetrahydrofuran solution (5 ml) were subjected to reaction using a procedure similar to that of Example 5(2) (3 hours), worked up and purified by column chromatography (ethyl acetate) to give the titled compound (152 mg, 86%) as a colorless solid.

IR(neat): 3370, 2968, 2935, 2846, 1462, 1367, 1228, 1194, 1149, 1055 cm$^{-1}$.

$^1$H NMR δ: 0.86(s, 3H), 0.99(s, 3H), 1.22(s, 6H), 2.73–2.85(m, 1H), 3.11–3.26(m, 2H), 3.79(brs, 1H), 3.99–4.15(m, 1H), 5.42–5.49(m, 1H), 5.58(brs, 1H), 5.75 (brd, J=5.6 Hz, 1H).

MS m/z: 446(M$^+$), 280(100%). UV $\lambda_{max}$ nm: 271, 282, 294.

(3) Synthesis of 1α,3β-dihydroxy-17-(5-hydroxy-5-methylhexylthiomethyl)-9,10-secoandrosta-5,7,10(19),16-tetraene 1α,3β-Dihydroxy-17-(5-hydroxy-5-methylhexylthiomethyl)androsta-5,7,16-triene (140 mg, 0.282 mmol) and ethanol (200 ml) were subjected to reaction using a procedure similar to that of Example 5(3) (irradiation for 7 min. 30 sec., reflux under heating for 2 hours) and purified by preparative thin layer chromatography (3 sheets (each 0.5 mm thickness), dichloromethane:ethanol=10:1, developed twice; and 2 sheets (each 0.5 mm thickness), toluene:ethyl acetate=5:6, developed three times) to give the titled compound (7.24 mg, 5%) as a colorless foam.

IR(neat): 3340, 2962, 2931, 2846, 1441, 1367, 1144, 1055 cm$^{-1}$.

$^1$H NMR δ: 0.75(s, 3H), 1.22(s, 6H), 2.75–2.89(m, 1H), 3.09–3.24(m, 2H), 4.19–4.29(br, 1H), 4.40–4.49(br, 1H), 5.01(brs, 1H), 5.34(brs, 1H), 5.54(brs, 1H), 6.10(d, J=11.2 Hz, 1H), 6.37(d, J=11.2 Hz, 1H).

MS m/z: 298(M$^+$-HS(CH$_2$)$_4$C(CH$_3$)$_2$OH), 59(100%). UV $\lambda_{max}$ nm: 263.

Example 33

(1) Synthesis of 1α,3β-bis(tert-butyldimethylsilyloxy)-17-{4-triethylsilyloxy-4-methyl-(2E)-pentenylthiomethyl}androsta-5,7,16-triene 17-Acetylthiomethyl-1α,3β-bis(tert-butyldimethylsilyloxy)androsta-5,7,16-triene (304 mg, 0.504 mmol), 1-bromo-4-triethylsilyloxy-4-methyl-(2E)-pentene (296 mg, 1.01 mmol), a 1M potassium hydroxide methanol solution (3 ml) and tetrahydrofuran (2 ml) were subjected to reaction using a procedure similar to that of Example 31(1) (at room temperature for 10 min.), worked up and purified by column chromatography (hexane:toluene=6:1) to give the titled compound (351 mg, 90%) as a pale yellow solid.

IR(neat): 2954, 2929, 2856, 1462, 1373, 1254, 1099, 1072, 1051, 1007 cm$^{-1}$.

$^1$H NMR δ: 0.05(s, 3H), 0.07(s, 6H), 0.11(s, 3H), 0.57(q, J=7.9 Hz, 6H), 0.85(s, 3H), 0.88(s, 18H), 0.94(t, J=7.9 Hz, 9H), 1.31(s, 6H), 2.80–2.90(m, 1H), 3.09(d, J=6.3 Hz, 2H), 3.13(brs, 2H), 3.71(brs, 1H), 3.98–4.11(m, 1H), 5.35–5.42(m, 1H), 5.48–5.70(m, 4H).

MS m/z: 772(M$^+$), 73(100%). UV $\lambda_{max}$ nm: 271, 282, 294.

(2) Synthesis of 1α,3β-dihydroxy-17-{4-hydroxy-4-methyl-(2E)-pentenylthiomethyl}androsta-5,7,16-triene 1α,3β-Bis(tert-butyldimethylsilyloxy)-17-{4-triethylsilyloxy-4-methyl-(2E)-pentenylthiomethyl}androsta-5,7,16-triene (115 mg, 0.149 mmol) and a 1M tetra-n-butylammonium fluoride tetrahydrofuran solution (4 ml) were subjected to reaction using a procedure similar to that of Example 5(2) (3 hours), worked up and purified by column chromatography (ethyl acetate) to give the titled compound (64 mg, 100%) as a pale yellow foam.

IR(neat): 3372, 3035, 2968, 2925, 2850, 1458, 1369, 1230, 1151, 1053, 1034 cm$^{-1}$.

$^1$H NMR δ: 0.86(s, 3H), 0.98(s, 3H), 1.34(s, 6H), 2.74–2.85(m, 1H), 3.10(d, J=6.3 Hz, 2H), 3.14(brs, 2H), 3.79(brs, 1H), 3.99–4.15(m, 1H), 5.43–5.49(m, 1H), 5.56–5.78(m, 4H).

MS m/z: 412(M$^+$-H$_2$O), 279(100%). UV $\lambda_{max}$ nm: 271, 282, 293.

(3) Synthesis of 1α,3β-dihydroxy-17-{4-hydroxy-4-methyl-(2E)-pentenylthiomethyl}-9,10-secoandrosta-5,7,10(19),16-tetraene 1α,3β-Dihydroxy-17-{4-hydroxy-4-methyl-(2E)-pentenylthiomethyl}androsta-5,7,16-triene (61 mg, 0.142 mmol) and ethanol (200 ml) were subjected to reaction using a procedure similar to that of Example 5(3) (irradiation for 4 min. 45 sec., reflux under heating for 2 hours) and purified by preparative thin layer chromatography (2 sheets (each 0.5 mm thickness), dichloromethane:ethanol=10:1, developed twice; 1 sheet (0.5 mm thickness), toluene:ethyl acetate=5:6, developed twice; and 1 sheet (0.5 mm thickness), hexane:ethyl acetate:ethanol=10:10:1, developed twice) to give the titled compound (7.24 mg, 5%) as a colorless foam.

IR(neat): 3380, 2924, 2850, 1590, 1363, 1120 cm$^{-1}$.

$^1$H NMR δ: 0.75(s, 3H), 1.34(s, 6H), 2.77–2.87(m, 1H), 3.07–3.13(m, 4H), 4.18–4.29(m, 1H), 4.40–4.50(m, 1H), 5.01(brs, 1H), 5.34(brs, 1H), 5.52–5.74(m, 3H), 6.10(d, J=11.2 Hz, 1H), 6.37(d, J=11.2 Hz, 1H).

MS m/z: 430(M$^+$), 91(100%). UV $\lambda_{max}$ nm: 264.

Example 34

(1) Synthesis of 1α,3β-bis(tert-butyldimethylsilyloxy)-17-(3-hydroxy-3-methylbutylthiomethyl)androsta-5,7,16-triene 17-Acetylthiomethyl-1α,3β-bis(tert-butyldimethylsilyloxy)androsta-5,7,16-triene (67.7 mg, 0.112 mmol), 1-bromo-3-hydroxy-3-methylbutane (93.5 mg, 0.560 mmol), 1M potassium hydroxide methanol solution (1 ml) and tetrahydrofuran (1 ml) were subjected to reaction using a procedure similar to that of Example 31(1) (at room temperature for 30 min.), worked up and purified by preparative thin layer chromatography (2 sheets (each 0.5 mm thickness), hexane:ethyl acetate=3:1, developed once) to give the titled compound (67.4 mg, 93%) as a colorless oil.

IR(neat): 3417, 2956, 2929, 2856, 1471, 1462, 1371, 1254, 1099, 1074 cm$^{-1}$.

$^1$H NMR δ: 0.05(s, 3H), 0.07(s, 3H), 0.07(s, 3H), 0.11(s, 3H), 0.85(s, 3H), 0.88(s, 9H), 0.89(s, 9H), 0.95(s, 3H), 1.24(s, 6H), 2.59(m, 2H), 2.85(m, 1H), 3.23(m, 2H), 3.71 (brs, 1H), 3.98–4.12(m, 1H), 5.36–5.42(m, 1H), 5.56–5.64 (m, 2H).

MS m/z: 646(M$^+$), 457(100%). UV $\lambda_{max}$ nm: 271, 281, 294.

(2) Synthesis of 1α,3β-dihydroxy-17-(3-hydroxy-3-methylbutylthiomethyl)androsta-5,7,16-triene 1α,3β-Bis(tert-butyldimethylsilyloxy)-17-(3-hydroxy-3-methylbutylthiomethyl)androsta-5,7,16-triene (63.5 mg, 0.0981 mmol), a 1M tetra-n-butylammonium fluoride tetrahydrofuran solution (1 ml) and tetrahydrofuran (1 ml) were subjected to reaction using a procedure similar to that of Example 5(2) (reflux under heating for 5.5 hours), worked up and purified by preparative thin layer chromatography (2 sheets (each 0.5 mm thickness), dichloromethane:ethanol=9:1, developed once) to give the titled compound (39.2 mg, 95%) as a colorless oil.

IR(neat): 3396, 2968, 2629, 2850, 1462, 1369, 1207, 1151, 1055 cm$^{-1}$.

$^1$H NMR δ: 0.86(s, 3H), 0.98(s, 3H), 1.24(s, 6H), 2.58(m, 2H), 2.79(m, 1H), 3.23(m, 2H), 3.78(brs, 1H), 3.99–4.11(m, 1H), 5.42–5.48(m, 1H), 5.59(brs, 1H), 5.73(brd, J=5.9 Hz, 1H).

MS m/z: 418(M$^+$), 298(100%). UV $\lambda_{max}$ nm: 271, 281, 293.

(3) Synthesis of 1α,3β-dihydroxy-17-(3-hydroxy-3-methylbutylthiomethyl)-9,10-secoandrosta-5,7,10(19),16-tetraene 1α,3β-Dihydroxy-17-(3-hydroxy-3-methylbutylthiomethyl)androsta-5,7,16-triene (37.0 mg, 0.0884 mmol) and ethanol (200 ml) were subjected to reaction using a procedure similar to that of Example 5(3) (irradiation for 4 min. 15 sec., reflux under heating for 2 hours) and purified by preparative thin layer chromatography (1 sheet (0.5 mm thickness), dichloromethane:ethanol=9:1, developed twice; 1 sheet (0.25 mm thickness), hexane:ethyl acetate:ethanol=5:5:1, developed twice; and 1 sheet (0.25 mm thickness), dichloromethane:ethyl acetate:ethanol=14:6:1, developed twice) to give the titled compound (0.764 mg, 2.1%) as a colorless oil.

IR(neat): 3367, 2925, 2850, 1437, 1367, 1288, 1209, 1146, 1055 cm$^{-1}$.

$^1$H NMR δ: 0.76(s, 3H), 1.24(s, 6H), 2.58(m, 2H), 2.82 (m, 1H), 3.21(m, 2H), 4.18–4.30(br, 1H), 4.38–4.49(br, 1H), 5.01(brs, 1H), 5.34(brs, 1H), 5.56(brs, 1H), 6.10(d, J=11.2 Hz, 1H), 6.37(d, J=11.2 Hz, 1H).

MS m/z: 418(M$^+$), 133(100%). UV $\lambda_{max}$ nm: 263.

Example 35

(1) Synthesis of 1α,3β-bis(tert-butyldimethylsilyloxy)-17-hydroxymethyl-9,10-secoandrosta-5,7,10(19),16-tetraene 1α,3β-Bis(tert-butyldimethylsilyloxy)-17-(hydroxymethyl)androsta-5,7,16-triene (750 mg, 1.38 mmol) and ethanol (600 ml) were subjected to reaction using a procedure similar to that of Example 5(3) (irradiation for 30 min., reflux under heating for 2 hours) and purified by column chromatography (hexane:ethyl acetate=10:1) to give a fraction (550 mg) containing the titled compound.

(2) Synthesis of 17-acetylthiomethyl-1α,3β-bis(tert-butyldimethylsilyloxy)-9,10-secoandrosta-5,7,10(19),16-tetraene The 1α,3β-bis(tert-butyldimethylsilyloxy)-17-hydroxymethyl-9,10-secoandrosta-5,7,10(19),16-tetraene-containing fraction (550 mg), methanesulfonyl chloride (0.23 ml, 2.97 mmol), triethylamine (0.56 ml, 4.02 mmol), tetrahydrofuran (5 ml), potassium thioacetate (0.457 g, 4.00 mmol) and dimethylsulfoxide (5 ml) were subjected to reaction using a procedure similar to that of Example 1(3) (mesylation for 15 min. and thioacetylation for 30 min.), worked up and purified by preparative thin layer chromatography (7 sheets (each 1.0 mm thickness), hexane:ethyl acetate=10:1, developed once) to give a fraction (430 mg) containing the titled compound.

(3) 17-acetylthiomethyl-1α,3β-dihydroxy-9,10-secoandrosta-5,7,10(19),16-tetraene The fraction (430 mg) containing 17-acetylthiomethyl-1α,3β-bis(tert-butyldimethylsilyloxy)-9,10-secoandrosta-5,7,10(19),16-tetraene obtained in the above (2) was dissolved in tetrahydrofuran (40 ml). The resulting solution was mixed with methanol (40 ml) and AMBERLYST 15 (18 g) under a nitrogen atmosphere, stirred at room temperature for 4 hours and filtered with CELITE. The thus obtained filtrate was mixed with sodium bicarbonate (100 mg) and stirred at room temperature for 5 min. After filtering off the sodium bicarbonate, the resulting filtrate was evaporated under reduced pressure to remove the solvent and purified by preparative thin layer chromatography (7 sheets (each 1.0 mm thickness), hexane:ethyl acetate:ethanol=5:5:1, developed once) to give the titled compound (30 mg, 5.8%, in 3 steps) as a colorless oil.

$^1$H NMR δ: 0.72(s, 3H), 2.33(s, 3H), 3.50–3.68(m, 2H), 4.10(brs, 1H), 4.43(brs, 1H), 5.00(s, 1H), 5.33(s, 1H), 5.57 (s, 1H), 6.10(d, J=11.2 Hz, 1H), 6.34(d, J=11.2 Hz, 1H).

(4) 17-(3-ethyl-3-hydroxypentylthiomethyl)-1α,3β-dihydroxy-9,10-secoandrosta-5,7,10(19),16-tetraene 17-Acetylthiomethyl-1α,3β-dihydroxy-9,10-secoandrosta-5,7,10(19),16-tetraene (10 mg, 0.0267 mmol), 1-bromo-3-ethyl-3-hydroxypentane (10 mg, 0.0513 mmol), a 1M potassium hydroxide methanol solution (0.5 ml) and tetrahydrofuran (0.5 ml) were subjected to reaction using a procedure similar to that of Example 31(1) (15 min.), worked up and purified by preparative thin layer chromatography (1 sheet (0.5 mm thickness), hexane:ethyl acetate=1:1, developed once; and 1 sheet (0.5 mm thickness), ethyl acetate:toluene=1:1, developed once) to give the titled compound (3.60 mg, 30%) as a colorless oil.

IR(neat): 3446, 2962, 2362, 1055 cm$^{-1}$.

$^1$H NMR δ: 0.76(s, 1H), 0.87(t, J=7.6 Hz, 6H), 3.20(brs, 2H), 4.25(brs, 1H), 4.44(brs, 1H), 5.01(s, 1H), 5.34(s, 1H), 5.56(brs, 1H), 6.10(d, J=11.2 Hz, 1H), 6.37(d, J=11.2 Hz, 1H).

MS m/z: 428(M$^+$-H$_2$O), 57(100%). UV $\lambda_{max}$ nm: 264.

Example 36

1α,3β-dihydroxy-17-(2-hydroxy-2-methylpropylthiomethyl)-9,10-secoandrosta-5,7,10(19),16-tetraene 17-Acetylthiomethyl-1α,3β-dihydroxy-9,10-secoandrosta-5,7,10(19),16-tetraene (5 mg, 0.0133 mmol), 1,2-epoxy-2-methylpropane (20 mg, 0.277 mmol), a 1M potassium hydroxide methanol solution (0.5 ml) and tetrahydrofuran (0.1 ml) were subjected to reaction using a procedure similar to that of Example 31(1) (at room temperature for 30 min.), worked up and purified by preparative thin layer chromatography (1 sheet (0.5 mm thickness), toluene:ethyl acetate=5:6, developed once) to give the titled compound (2.40 mg, 45%) as a colorless foam.

IR(neat): 3360, 2966, 2927, 2848, 1437, 1367, 1144, 1055 cm$^{-1}$.

$^1$H NMR δ: 0.75(s, 3H), 1.28(s, 6H), 2.62(s, 2H), 2.75–2.89(m, 1H), 3.16–3.33(m, 2H), 4.17–4.30(m, 1H), 4.40–4.51(br, 1H), 5.01(brs, 1H), 5.34(brs, 1H), 5.58(brs, 1H), 6.11(d, J=11.2 Hz, 1H), 6.37(d, J=11.2 Hz, 1H).

MS m/z: 404(M$^+$), 59(100%). UV λ$_{max}$ nm: 264.

Example 37

17-(2-ethyl-2-hydroxybutylthiomethyl)-1α,3β-dihydroxy-9,10-secoandrosta-5,7,10(19),16-tetraene 17-Acetylthiomethyl-1α,3β-dihydroxy-9,10-secoandrosta-5,7,10(19),16-tetraene (5 mg, 0.0133 mmol), 1,2-epoxy-2-ethylbutane (33 mg, 0.329 mmol), a 1M potassium hydroxide methanol solution (0.5 ml) and tetrahydrofuran (0.1 ml) were subjected to reaction using a procedure similar to that of Example 31(1) (at room temperature for 10 min.), worked up and purified by preparative thin layer chromatography (1 sheet (0.5 mm thickness), toluene:ethyl acetate=1:1, developed once) to give the titled compound (3.27 mg, 57%) as a colorless glassy substance.

IR(neat): 3370, 2962, 2927, 2879, 2848, 1456, 1417, 1367, 1140, 1055 cm$^{-1}$.

$^1$H NMR δ: 0.75(s, 3H), 0.88(t, J=7.6 Hz, 6H), 2.62(s, 2H), 2.77–2.90(m, 1H), 3.15–3.29(m, 2H), 4.18–4.30(br, 1H), 4.40–4.50(br, 1H), 5.01(brs, 1H), 5.34(brs, 1H), 5.58(brs, 1H), 6.10(d, J=11.2 Hz, 1H), 6.37(d, J=11.2 Hz, 1H).

MS m/z: 432(M$^+$), 87(100%). UV λ$_{max}$ nm: 264.

Example 38

1α,3β-dihydroxy-17-{(2R)-hydroxy-3-methylbutylthiomethyl}-9,10-secoandrosta-5,7,10(19),16-tetraene 17-Acetylthiomethyl-1α,3β-dihydroxy-9,10-secoandrosta-5,7,10(19),16-tetraene (5 mg, 0.0133 mmol), (2R)-1,2-epoxy-3-methylbutane (29 mg, 0.337 mmol), a 1M potassium hydroxide methanol solution (0.5 ml) and tetrahydrofuran (0.1 ml) were subjected to reaction using a procedure similar to that of Example 31(1) (at room temperature for 30 min.), worked up and purified by preparative thin layer chromatography (1 sheet (0.5 mm thickness), hexane:ethyl acetate=1:1, developed once) to give the titled compound (2.88 mg, 52%) as a colorless foam.

IR(neat): 3370, 2956, 2923, 2848, 1433, 1367, 1227, 1113, 1053, 1007 cm$^{-1}$.

$^1$H NMR δ: 0.73(s, 3H), 0.93(d, J=6.9 Hz, 3H), 0.97(d, J=6.9 Hz, 3H), 3.13(d, J=14.9 Hz, 1H), 3.23(d, J=14.9 Hz, 1H), 3.35–3.44(m, 1H), 4.18–4.29(m, 1H), 4.40–4.49(m, 1H), 5.01(brs, 1H), 5.34(brs, 1H), 5.55(brs, 1H), 6.10(d, J=11.2 Hz, 1H), 6.37(d, J=11.2 Hz, 1H).

MS m/z: 298(M$^+$-HSCH$_2$CH(OH)CH(CH$_3$)$_2$), 55(100%). UV λ$_{max}$ nm: 263.

Example 39

1α,3β-dihydroxy-17-(4-hydroxy-4-methyl-2-pentynylthiomethyl)-9,10-secoandrosta-5,7,10(19),16-tetraene 17-Acetylthiomethyl-1α,3β-dihydroxy-9,10-secoandrosta-5,7,10(19),16-tetraene (6 mg, 0.0160 mmol), 1-bromo-4-hydroxy-4-methyl-2-pentyne (10 mg, 0.0565 mmol), a 1M potassium hydroxide methanol solution (0.5 ml) and tetrahydrofuran (0.5 ml) were subjected to reaction using a procedure similar to that of Example 31(1) (at room temperature for 10 min.), worked up and purified by preparative thin layer chromatography (1 sheet (0.5 mm thickness), toluene:ethyl acetate=5:6, developed twice) to give the titled compound (4.99 mg, 73%) as a colorless glassy substance.

IR(neat): 3350, 2974, 2929, 2848, 1365, 1167, 1055 cm$^{-1}$.

$^1$H NMR δ: 0.76(s, 3H), 1.52(s, 6H), 2.76–2.87(m, 1H), 3.22(s, 2H), 3.24–3.40(m, 2H), 4.18–4.31(m, 1H), 4.40–4.49(m, 1H), 5.01(brs, 1H), 5.34(brs, 1H), 5.59(brs, 1H), 6.11(d, J=11.2 Hz, 1H), 6.37(d, J=11.2 Hz, 1H).

MS m/z: 410(M$^+$-H$_2$O), 91(100%). UV λ$_{max}$ nm: 264.

Example 40

17-(4-ethyl-4-hydroxy-2-hexynylthiomethyl)-1α,3β-dihydroxy-9,10-secoandrosta-5,7,10(19),16-tetraene 17-Acetylthiomethyl-1α,3β-dihydroxy-9,10-secoandrosta-5,7,10(19),16-tetraene (5 mg, 0.0134 mmol), 1-bromo-4-ethyl-4-hydroxy-2-hexyne (10 mg, 0.04876 mmol), a 1M potassium hydroxide methanol solution (0.5 ml) and tetrahydrofuran (0.5 ml) were subjected to reaction using a procedure similar to that of Example 31(1) (10 min.), worked up and purified by preparative thin layer chromatography (1 sheet (0.5 mm thickness), hexane:ethyl acetate=1:1, developed once; and 1 sheet (0.5 mm thickness), dichloromethane:ethanol=20:1, developed once) to give the titled compound (3.30 mg, 54%) as a colorless oil.

IR(neat): 3361, 2929, 1455, 1052 cm$^{-1}$.

$^1$H NMR δ: 0.76(s, 3H), 1.04(t, J=7.3 Hz, 6H), 3.24(s, 2H), 3.32(m, 2H), 4.22(m, 1H), 4.43(m, 1H), 5.01(s, 1H), 5.34(s, 1H), 5.59(brs, 1H), 6.11(d, J=11.5 Hz, 1H), 6.37(d, J=11.5 Hz, 1H).

MS m/z: 438(M$^+$-H$_2$O), 57(100%). UV λ$_{max}$ nm: 263.

Example 41

17-{4-ethyl-4-hydroxy-(2E)-hexenylthiomethyl}-1α,3β-dihydroxy-9,10-secoandrosta-5,7,10(19),16-tetraene 17-Acetylthiomethyl-1α,3β-dihydroxy-9,10-secoandrosta-5,7,10(19),16-tetraene (10 mg, 0.0267 mmol), 1-bromo-4-ethyl-4-hydroxy-(2E)-hexene (10 mg, 0.0483 mmol), a 1M potassium hydroxide methanol solution (0.5 ml) and tetrahydrofuran (0.5 ml) were subjected to reaction using a procedure similar to that of Example 31(1) (30 min.), worked up and purified by preparative thin layer chromatography (1 sheet (0.5 mm thickness), hexane:ethyl acetate=1:1, developed once; and 1 sheet (0.5 mm thickness), ethyl acetate:toluene=1:1, developed once) to give the titled compound (5.09 mg, 42%) as a colorless oil.

IR(neat): 3465, 2925, 2852 cm$^{-1}$.

$^1$H NMR δ: 0.75(s, 3H), 0.88(t, J=7.6 Hz, 6H), 3.01–3.16 (m, 4H), 4.24(m, 1H), 4.44(brs, 1H), 5.01(s, 1H), 5.34(s, 1H), 5.45–5.69(m, 3H), 6.10(d, J=11.2 Hz, 1H), 6.37(d, J=11.2 Hz, 1H).

MS m/z: 440(M$^+$-H$_2$O), 57(100%). UV λ$_{max}$ nm: 263.

Example 42

(1) 17-(4-triethylsilyloxy-4-methylpentylthiomethyl)-1α,3β-dihydroxy-9,10-secoandrosta-5,7,10 (19),16-tetraene 1α,3β-Dihydroxy-17-acetylthiomethyl-9,10-secoandrosta-5,7,10(19),16-tetraene (5 mg, 0.0133 mmol), 1-bromo-4-triethylsilyloxy-4-methylpentane (70 mg, 0.226 mmol), a 1M potassium hydroxide methanol solution (1 ml) and tetrahydrofuran (0.1 ml) were subjected to reaction using a procedure similar to that of Example 31(1) (at room temperature for 30 min.) and worked up to give a mixture (5 mg) containing the titled compound.

(2) 1α,3β-dihydroxy-17-(4-hydroxy-4-methylpentylthiomethyl)-9,10-secoandrosta-5,7,10(19),16-tetraene The mixture (5 mg) obtained in the above (1), AMBERLYST 15 (1 g), methanol (5 ml) and tetrahydrofuran (5 ml) were subjected to reaction using a procedure similar to that of Example 35(3) (at room temperature for 20 min.), worked up and purified by preparative thin layer chromatography (1 sheet (0.5 mm thickness), dichloromethane:ethanol=40:3, developed once) to give the titled compound (2.85 mg, 49%) as a colorless glassy substance.

IR(neat): 3380, 2962, 2848, 1435, 1367, 1296, 1146, 1055 cm$^{-1}$.

$^1$H NMR δ: 0.75(s, 3H), 1.22(s, 6H), 2.77–2.87(m, 1H), 3.11–3.25(m, 2H), 4.18–4.31(m, 1H), 4.39–4.50(m, 1H), 5.01(brs, 1H), 5.34(brs, 1H), 5.54(brs, 1H), 6.10(d, J=11.2 Hz, 1H), 6.37(d, J=11.2 Hz, 1H).

MS m/z: 298(M$^+$-HS(CH$_2$)$_3$C(CH$_3$)$_2$OH), 91(100%). UV λ$_{max}$ nm: 263.

Example 43

(1) 17-{4-triethylsilyloxy-4-methyl-(2Z)-pentenylthiomethyl}-1α,3β-dihydroxy-9,10-secoandrosta-5,7,10(19),16-tetraene 17-Acetylthiomethyl-1α,3β-dihydroxy-9,10-secoandrosta-5,7,10(19),16-tetraene (5 mg, 0.0133 mmol), 1-bromo-4-triethylsilyloxy-4-methyl-(2Z)-pentene (10 mg, 0.0341 mmol), a 1M potassium hydroxide methanol solution (0.5 ml) and tetrahydrofuran (0.5 ml) were subjected to reaction using a procedure similar to that of Example 31(1) (at room temperature for 10 min.) and worked up to give a mixture (5 mg) containing the titled compound.

(2) 1α,3β-dihydroxy-17-{4-hydroxy-4-methyl-(2Z)-pentenylthiomethyl}-9,10-secoandrosta-5,7,10(19),16-tetraene The mixture (5 mg) obtained in the above (1), AMBERLYST 15 (1 g), methanol (2 ml) and tetrahydrofuran (2 ml) were subjected to reaction using a procedure similar to that of Example 35(3) (at room temperature for 3 hours), worked up and purified by preparative thin layer chromatography (1 sheet (0.5 mm thickness), hexane:ethyl acetate=1:1, developed once; and 1 sheet (0.5 mm thickness), dichloromethane:ethanol=20:1, developed once) to give the titled compound (1.54 mg, 27%) as a colorless foam.

IR(neat): 3360, 2923, 2850, 1437, 1363, 1142, 1055 cm$^{-1}$.

$^1$H NMR δ: 0.75(s, 3H), 1.36(s, 6H), 2.75–2.86(m, 1H), 3.22(s, 2H), 3.39–3.58(m, 2H), 4.18–4.29(m, 1H), 4.39–4.48(m, 1H), 5.01(brs, 1H), 5.34(brs, 1H), 5.39–5.61 (m, 3H), 6.10(d, J=11.2 Hz, 1H), 6.37(d, J=11.2 Hz, 1H).

MS m/z: 412(M$^+$-H$_2$O), 133(100%). UV λ$_{max}$ nm: 265.

Example 44

(1) 17-{4-ethyl-4-triethylsilyloxy-(2Z)-hexenylthiomethyl}-1α,3β-dihydroxy-9,10-secoandrosta-5,7,10(19),16-tetraene 17-Acetylthiomethyl-1α,3β-dihydroxy-9,10-secoandrosta-5,7,10(19),16-tetraene (4 mg, 0.0107 mmol), 1-bromo-4-ethyl-4-triethylsilyloxy-(2Z)-hexene (10 mg, 0.0311 mmol), a 1M potassium hydroxide methanol solution (0.5 ml) and tetrahydrofuran (0.5 ml) were subjected to reaction using a procedure similar to that of Example 31(1) (10 min.) and worked up to give a mixture (4.0 mg) containing the titled compound.

(2) 17-{4-ethyl-4-hydroxy-(2Z)-hexenylthiomethyl}-1α,3β-dihydroxy-9,10-secoandrosta-5,7,10 (19),16-tetraene The mixture (4.0 mg) containing 17-{4-ethyl-4-triethylsilyloxy-(2Z)-hexenylthiomethyl}-1α,3β-dihydroxy-9,10-secoandrosta-5,7,10(19),16-tetraene obtained in the above (1), a 1M tetra-n-butylammonium fluoride tetrahydrofuran solution (1.1 ml) and tetrahydrofuran (2 ml) were subjected to reaction using a procedure similar to that of Example 5(2) (at room temperature for 3 days), worked up and purified by preparative thin layer chromatography (1 sheet (0.5 mm thickness), hexane:ethyl acetate=1:1, developed once;. 1 sheet (0.5 mm thickness), dichloromethane:ethanol=10:1, developed once; 1 sheet (0.5 mm thickness), dichloromethane:acetonitrile=2:1, developed once; and 1 sheet (0.5 mm thickness), toluene:ethyl acetate=1:1, developed twice) to give the titled compound (1.15 mg, 23%) as a colorless oil.

IR(neat): 3465, 2960, 2852, 1731, 1462, 1053 cm$^{-1}$.

$^1$H NMR δ: 0.75(s, 3H), 0.91(t, J=7.3 Hz, 6H), 3.22(s, 2H), 3.48(d, J=8.3 Hz, 2H), 4.24(brs, 1H), 4.44(brs, 1H), 5.01(s, 1H), 5.30–5.66(m, 4H), 6.10(d, J=11.6 Hz, 1H), 6.37(d, J=11.6 Hz, 1H).

MS m/z: 440(M$^+$–H$_2$O), 57(100%). UV λ$_{max}$ nm: 263.

Example 45

(1) 1α,3β-bis(tert-butyldimethylsilyloxy)-17-methyleneandrost-5-ene

A mixture of tetrahydrofuran (70 ml), methyltriphenylphosphonium bromide (50 g) and potassium t-butoxide (13.9 g) were stirred at 60° C. for 2 hours, while under suspension. To this suspension, was added 1α,3β-bis(tert-butyldimethylsilyloxy)androst-5-ene (18.7 g) and tetrahydrofuran (60 ml), followed by reaction for 2 hours under reflux. Under cooling with ice, the reaction mixture was slowly added to a cooled mixture of hexane (200 ml) and water (100 ml) to stop the reaction. The organic layer was washed with saturated brine twice, dried over anhydrous magnesium sulfate and evaporated under reduced pressure to remove the solvent, giving crude crystals (27 g). The crude crystals were mixed with hexane (100 ml), stirred at room temperature while under suspension. After filtering off insoluble material from the suspension, the filtrate was evaporated under reduced pressure to remove the solvent, giving crude crystals, which were then dissolved in acetone (80 ml) by stirring at room temperature. The mixture was mixed with methanol (160 ml) and stirred at room temperature; the thus precipitated crystals were collected by filtration and dried to give the titled compound (13.2 g).

$^1$H NMR δ: 5.4–5.5(1H, m), 4.6–4.7(2H, m), 3.9–4.1(1H, m), 3.8(1H, br), 1.0–2.6 (17H, m), 0.99(3H, s), 0.88(9H, s), 0.87(9H, s), 0.80(3H, s), 0.08(3H, s), 0.06(3H, s), 0.05(3H, s), 0.03(3H, s).

(2) 1α,3β-bis(tert-butyldimethylsilyloxy)-17β-(hydroxymethyl)androst-5-ene

To 1α,3β-bis(tert-butyldimethylsilyloxy)-17-methyleneandrost-5-ene (30.3 g), was added 9-borabicyclo[3,3,1]nonane (0.5M solution in tetrahydrofuran, 228 ml) and reacted by stirring at room temperature for 4 hours. Under cooling with ice, a 3M sodium hydroxide solution (150 ml) and then a 30% hydrogen peroxide solution (150 ml) were added to the reaction mixture, followed by stirring at room temperature for 1 hour. The reaction mixture was extracted with ethyl acetate, the organic layer was washed with saturated brine, dried over anhydrous magnesium sulfate and evaporated under reduced pressure to remove the solvent, giving crude crystals (37.3 g). The crude crystals were mixed with methanol, stirred while under suspension, filtered and the thus obtained crystals were dried to give the titled compound (24.3 g).

$^1$H NMR δ: 5.4–5.5(1H, m), 3.9–4.1(1H, m), 3.8(1H, br), 3.7(1H, dd), 3.6(1H, dd), 2.1–2.3(2H, m), 1.0–2.0 (17H, m), 0.97(3H, s), 0.88(9H, s), 0.81(9H, s), 0.66(3H, s), 0.07(3H, s), 0.05(3H, s), 0.04(3H, s), 0.02(3H, s).

(3) 1α,3β-bis(tert-butyldimethylsilyloxy)-17β-(N,N-dimethylaminocarbonylethoxymethyl)androst-5-ene To 1α,3-bis(tert-butyldimethylsilyloxy)-17β-(hydroxymethyl)androst-5-ene (18.4 g), was added N,N-dimethylacrylamide (9.95 g), sodium hydride (60% in oil, 2.0 g), 15-crown-5 (2.2 g) and tetrahydrofuran (73.5 ml), followed by reaction at 0° C. for 8 hours. After stopping the reaction by adding a saturated aqueous ammonium chloride solution, the organic layer was washed with a saturated aqueous sodium bicarbonate solution and saturated brine, dried over anhydrous magnesium sulfate and evaporated under reduced pressure to remove the solvent. The resulting residue was mixed with methanol (90 ml), stirred at room temperature while under suspension, followed by centrifugation. The thus obtained solid was dried to give the titled compound (13.2 g).

$^1$H NMR δ: 5.4–5.5(1H, m), 3.9–4.1(1H, m), 3.8(1H, br), 3.6–3.7(2H, m), 3.4–3.5(1H, dd), 3.3–3.4(1H, dd), 3.0(3H, s), 2.9(3H, s), 2.5–2.6(2H, m), 2.1–2.4(2H, m), 1.0–2.0 (16H, m), 0.95(3H, s), 0.86 (18H, s), 0.61(3H, s), 0.05(3H, s), 0.04(3H, s), 0.03(3H, s), 0.01(3H, s).

(4) 1α,3β-bis(tert-butyldimethylsilyloxy)-17β-(N,N-dimethylaminocarbonylethoxymethyl)androsta-5,7-diene 4-phenyl-1,2,4-triazoline-3,5-dione adduct To 1α,3β-bis(tert-butyldimethylsilyloxy)-17β-(N,N-dimethylaminocarbonylethoxymethyl)androst-5-ene (15 g), were added N-bromosuccinimide (5.36 g), 2,2'-azobis isobutyronitrile (1.06 g), hexane (120 ml) and tetrahydrofuran (30 ml), followed by reflux under heating for 15 min. After cooling to room temperature, the mixture was filtered to remove insoluble material and the filtrate was concentrated under reduced pressure. To the resultant, were added toluene (50 ml) and γ-collidine (9.8 ml), followed by reaction under reflux for 2 hours. After cooling to room temperature, the reaction mixture was filtered and the filtrate was washed with 0.5M hydrochloric acid, a saturated aqueous sodium bicarbonate solution and then saturated brine. The organic layer was dried over anhydrous magnesium sulfate, concentrated under reduced pressure. To the thus obtained residue, were added dichloromethane (70 ml) and 4-phenyl-1,2,4-triazoline-3,5-dione, followed by reaction at room temperature. The reaction mixture was washed with water, dried over anhydrous magnesium sulfate and evaporated under reduced pressure to remove the solvent. The thus obtained residue was purified by column chromatography (hexane:ethyl acetate=1:2) to give the titled compound (7.43 g).

$^1$H NMR δ: 7.3–7.1(5H, m), 6.2(1H, d, J=8.2 Hz), 6.1(1H, d, J=8.2 Hz), 4.6(1H, m), 3.7(1H, m), 3.6–3.5(2H, m), 3.4–3.2(1H, m), 3.2–3.1(1H, m), 2.9(3H, s), 2.8(3H, s), 0.8(3H, s), 0.77(9H, s), 0.76(9H, s), 0.64(3H, s), 0.01(3H, s), –0.02(3H, s), –0.04(3H, s), –0.06(3H, s).

(5) 1α,3β-bis(tert-butyldimethylsilyloxy)-17β-(hydroxymethyl)androsta-5,7-diene 4-phenyl-1,2,4-triazoline-3,5-dione adduct To 1α,3β-bis(tert-butyldimethylsilyloxy)-17β-(N,N-dimethylaminocarbonylethoxymethyl)androsta-5,7-diene 4-phenyl-1,2,4-triazoline-3,5-dione adduct (9 g), were added tetrahydrofuran (90 ml) and then potassium t-butoxide (10.5 g), followed by reaction at room temperature for 10 min. After stopping the reaction by adding saturated brine, the reaction mixture was extracted with ethyl acetate. The organic layer was dried over anhydrous magnesium sulfate, evaporated under reduced pressure to remove the solvent and the thus obtained residue was purified by column chromatography (hexane:ethyl acetate=2:1) to give the titled compound (6.34 g).

$^1$H NMR δ: 7.4–7.2(5H, m), 6.3(1H, d, J=8.2 Hz), 6.2(1H, d, J=8.2 Hz), 4.7(1H, m), 3.8(1H, m), 3.7–3.6(2H, m), 3.3–3.2(1H, m), 0.90(3H, s), 0.86(9H, s), 0.85(9H, s), 0.77 (3H, s), 0.01(3H, s), 0.07(3H, s), 0.05(3H, s), 0.03(3H, s).

(6) 1α,3β-bis(tert-butyldimethylsilyloxy)-17β-(hydroxymethyl)androsta-5,7-diene

To 1α,3β-bis(tert-butyldimethylsilyloxy)-17β-(hydroxymethyl)androsta-5,7-diene 4-phenyl-1,2,4-triazoline-3,5-dione adduct (6.3 g), was added 1,3-dimethyl-2-imidazolidinone (100 ml), followed by heating at 140° C. for 3 hours. The reaction mixture was extracted with hexane, the organic layer was washed with saturated brine, dried over anhydrous magnesium sulfate and evaporated under reduced pressure to remove the solvent. The thus obtained residue was purified by column chromatography (hexane:ethyl acetate=5:1) to give the titled compound (3.61 g).

$^1$H NMR δ: 5.6(1H, m), 5.3(1H, m), 4.0(1H, m), 4.7(1H, m), 4.0–3.7(2H, m), 3.6–3.7(1H, m), 2.8(1H, m), 2.4–2.3 (2H, m), 0.91(3H, s), 0.88(9H, s), 0.83(9H, s), 0.61(3H, s), 0.11(3H, s), 0.06(6H, s), 0.05(3H, s).

(7) 1α,3β-dihydroxy-17β-(hydroxymethyl)androsta-5,7-diene

To 1α,3β-bis(tert-butyldimethylsilyloxy)-17β-(hydroxymethyl)androsta-5,7-diene (1.0 g), was added a 1M tetra-n-butylammonium fluoride tetrahydrofuran solution (11 ml), followed by reflux for 6 hours. After adding ethyl acetate, the reaction mixture was washed with saturated brine, a saturated aqueous sodium bicarbonate solution (twice) and then saturated brine. The organic layer was dried over anhydrous magnesium sulfate, evaporated under reduced pressure to remove the solvent and the thus obtained residue was purified by column chromatography (hexane:ethyl acetate=1:2) to give the titled compound (560 mg).

$^1$H NMR(DMSO-d6) δ: 5.4(1H, m), 5.3(1H, m), 4.6(1H, d, J=4.6 Hz), 4.4(1H, d, J=4.6 Hz), 4.2(1H, m), 3.8(1H, m), 3.5(1H, br), 3.6–3.4(1H, m), 3.4–3.2(1H, m), 2.7–2.9(1H, m), 0.9(3H, s), 0.5(3H, s).

$^{13}$C NMR (DMSO-d6) δ: 140.4, 138.7, 119.5, 114.7, 70.7, 63.2, 62.3, 53.7, 52.1, 41.7, 41.5, 40.4, 38.6, 37.5, 37.1, 25.3, 23.0, 19.5, 15.8, 12.0.

(8) 1α,3β-dihydroxy-17β-hydroxymethyl-9,10-secoandrosta-5,7,10(19)-triene

1α,3β-Dihydroxy-17β-(hydroxymethyl)androsta-5,7-diene (200 mg) was dissolved in tetrahydrofuran (200 ml), subjected to irradiation for 2 min. by 400 W high-pressure mercury lamp, refluxed for 1.5 hours and evaporated to remove the solvent under reduced pressure. The resulting residue was mixed with acetone, stirred and then filtered to remove the thus formed precipitate. The filtrate was evaporated under reduced pressure to remove the solvent and the resulting residue was subjected to high performance liquid chromatography (27% acetonitrile in water) to give the titled compound (16.33 mg).

$^1$H NMR δ: 6.4(1H, d), 6.0(1H, d), 5.3(1H, m), 5.0(1H, m), 4.5–4.4(1H, m), 4.3–4.2(1H, m), 3.8–3.6(1H, m), 3.6–3.5(1H, m), 2.9–2.8(1H, m), 2.6–2.5(1H, m), 2.4–2.2(1H, m), 1.5(3H, s), 0.5(3H, s).

Example 46

(1) 1α,3β-bis(tert-butyldimethylsilyloxy)-17β-{4-ethyl-4-(triethylsilyloxy)hexyloxymethyl}androst-5-ene 1α,3β-Bis(tert-butyldimethylsilyloxy)-17β-(hydroxymethyl)androst-5-ene (11.0 g) was dissolved in tetrahydrofuran. Under cooling with ice, potassium hydride (30% in oil, 200.3 g) and 18-crown-6 (2.64 g) were added to the solution, which was then stirred for 5 min. 1-Bromo-4-ethyl-4-(triethylsilyloxy)hexane (25.91 g) was then added to the mixture and reacted for 3.5 hours. After stopping the reaction by adding a saturated aqueous ammonium chloride solution, the mixture was extracted with ethyl acetate. The organic layer was dried over anhydrous magnesium sulfate, filtered and the filtrate was evaporated under reduced pressure to remove the solvent. The resulting residue was purified by column chromatography (hexane:ethyl acetate=50:1) to give the titled compound (15.8 g).

$^1$H NMR δ: 5.5(1H, m), 4.0(1H, m), 3.7(2H, m), 3.4–3.2(4H, m), 2.4–2.1(2H, m), 0.9–0.5 (10H, m), 0.07(3H, s), 0.05(3H, s), 0.04(3H, s), 0.02(3H, s).

(2) 1α,3β-bis(tert-butyldimethylsilyloxy)-17β-{4-ethyl-4-(triethylsilyloxy)hexyloxymethyl}androsta-5,7-diene 4-phenyl-1,2,4-triazoline-3,5-dione adduct To 1α,3β-bis(tert-butyldimethylsilyloxy)-17β-{4-ethyl-4-(triethylsilyloxy)hexyloxymethyl}androst-5-ene (1.0 g), were added hexane (15 ml), N-bromosuccinimide (336.4 mg) and then 2,2'-azobis isobutyronitrile (77.6 mg), followed by reaction under reflux for 30 min. After cooling with ice, the mixture was filtered to remove insoluble material and the filtrate was evaporated under reduced pressure to remove the solvent. To the resulting residue, were added toluene (10 ml) and γ-collidine (534.4 mg), followed by reflux for 2 hours. The mixture was filtered to remove insoluble material and the filtrate was diluted with hexane. The organic layer was washed with 1M hydrochloric acid, a saturated aqueous sodium bicarbonate solution and then saturated brine and evaporated to remove the solvent under reduced pressure. The resulting residue was purified by column chromatography (hexane:ethyl acetate 40:1), dissolved in dichloromethane (20 ml) and subjected to reaction for 1 hour by adding 4-phenyl-1,2,4-triazoline-3,5-dione. The reaction mixture was evaporated to remove the solvent under reduced pressure and the resulting residue was purified by column chromatography (hexane:ethyl acetate=7:1) to give the titled compound (0.45 g).

$^1$H NMR δ: 7.5–7.2(5H, m), 6.3(1H, d, J=8.2 Hz), 6.2(1H, d, J=8.2 Hz), 4.7(1H, m), 3.8(1H, m), 3.5–3.2(5H, m), 2.6–2.4(3H, m), 0.6–0.5(6H, m), 0.10(3H, s), 0.07(3H, s), 0.05(3H, s), 0.03(3H, s).

(3) 1α,3β-bis(tert-butyldimethylsilyloxy)-17β-{4-ethyl-4-(triethylsilyloxy)hexyloxymethyl}androsta-5,7-diene After adding 1,3-dimethyl-2-imidazolidinone (10 ml) to 1α,3β-bis(tert-butyldimethylsilyloxy)-17β-{4-ethyl-4-(triethylsilyloxy)hexyloxymethyl}androsta-5,7-diene 4-phenyl-1,2,4-triazoline-3,5-dione adduct (0.45 g), the mixture was heated to 140° C. and reaction was proceeded for 2 hours. The reaction mixture was cooled and extracted with hexane. The organic layer was washed with saturated brine, dried over anhydrous magnesium sulfate and evaporated under reduced pressure to remove the solvent. The resulting residue was purified by column chromatography (hexane:ethyl acetate=40:1) to give the titled compound (0.18 g).

$^1$H NMR δ: 5.6(1H, m), 5.3(1H, m), 4.0(1H, m), 3.7(1H, m), 3.5–3.3(4H, m), 2.8(1H, m), 0.6–0.5(9H, m), 0.07(3H, s), 0.05(3H, s), 0.04(3H, s), 0.02(3H, s).

(4) 1α,3β-dihydroxy-17β-(4-ethyl-4-hydroxyhexyloxymethyl)androsta-5,7-diene To 1α,3β-bis(tert-butyldimethylsilyloxy)-17β-{4-ethyl-4-(triethylsilyloxy)hexyloxymethyl}androsta-5,7-diene (180 mg), was added a 1M tetra-n-butylammonium fluoride tetrahydrofuran solution (6 ml), followed by reflux under heating for 5 hours. After adding ethyl acetate, the mixture was washed with saturated brine, a saturated aqueous sodium bicarbonate solution and then saturated brine. The organic layer was dried over anhydrous magnesium sulfate, evaporated under reduced pressure to remove the solvent and the resulting residue was purified by column chromatography (ethyl acetate) to give the titled compound (0.10 g).

$^1$H NMR δ: 5.7(1H, m), 5.3(1H, m), 4.0(1H, m), 3.7(1H, m), 3.6–3.2(6H, m), 0.6(3H, s).

¹³C NMR δ: 140.3, 138.7, 119.5, 114.8, 72.2, 71.7, 71.0, 70.7, 63.2, 53.5, 49.2, 41.9, 41.5, 40.4, 38.6, 37.5, 37.0, 34.2, 30.6, 25.2, 23.6, 23.1, 19.5, 15.9, 12.0, 7.7.

(5) 1α,3β-dihydroxy-17β-(4-ethyl-4-hydroxyhexyloxymethyl)-9,10-secoandrosta-5,7,10(19)-triene 1α,3β-Dihydroxy-17β-(4-ethyl-4-hydroxyhexyloxymethyl)androsta-5,7-diene (204 mg) was dissolved in tetrahydrofuran (200 ml), subjected to irradiation by 400 W high-pressure mercury lamp for 2.5 min., refluxed for 2.5 hours and evaporated to remove the solvent under reduced pressure. The resulting residue was subjected to high performance liquid chromatography (methanol:acetonitrile:water=4:3:3) to give the titled compound (11.0 mg).

¹H NMR δ: 6.4(1H, d, J=10.8 Hz), 6.1(1H, d, J=10.8 Hz), 5.3(1H, m), 5.0(1H, m), 4.4(1H, m), 4.2(1H, m), 3.4–3.2 (5H, m), 2.9(1H, m), 2.6(1H, m), 2.3(1H, m), 1.0–0.8(6H, m), 0.5(3H, s).

¹³C NMR δ: 147.6, 142.8, 133.0, 124.9, 117.1, 111.8, 73.9, 72.8, 71.8, 70.9, 66.9, 55.8, 50.3, 45.3, 45.1, 42.9, 39.1, 35.5, 31.0, 30.9, 29.1, 25.3, 23.9, 23.3, 22.6, 12.5, 7.9.

Example 47

(1) 1α,3β-bis(tert-butyldimethylsilyloxy)-17β-(3-hydroxy-3-methylbutoxymethyl)androsta-5,7-diene To 1α,3β-bis(tert-butyldimethylsilyloxy)-17β-(N,N-dimethylaminocarbonylethoxymethyl)androsta-5,7-diene 4-phenyl-1,2,4-triazoline-3,5-dione adduct (2.3 g), was added 1,3-dimethyl-2-imidazolidinone (30 ml), followed by heating at 140° C. for 3 hours. The reaction mixture was extracted with hexane, the organic layer was washed with saturated brine, dried over anhydrous magnesium sulfate and evaporated under reduced pressure to remove the solvent. The resulting residue was purified by column chromatography (hexane:ethyl acetate=1:2) to give 1α,3β-bis(tert-butyldimethylsilyloxy)-17β-(N,N-dimethylaminocarbonylethoxymethyl)androsta-5,7-diene. To a suspension of anhydrous cerous (III) chloride (2.6 g) and tetrahydrofuran (8.3 ml), was added a 1.0M methylmagnesium bromide/tetrahydrofuran solution (8.7 ml) at 0° C., followed by stirring for 0.5 hours. The reaction mixture and the above-obtained 1α,3β-bis(tert-butyldimethylsilyloxy)-17β-(N,N-dimethylaminocarbonylethoxymethyl)androsta-5,7-diene (1.5 g) were mixed and reacted for 1 hour. The reaction mixture was added to a mixture of potassium hydrogen sulfate solution and hexane cooled at −10° C. in order to stop the reaction and then filtered. The organic layer was dried over anhydrous magnesium sulfate, evaporated under reduced pressure to remove the solvent and the resultant was reacted for 1 hour with Grignard solution, which was prepared as above. The thus obtained reaction mixture was worked up as above and purified by column chromatography (hexane:ethyl acetate=7:1) to give the titled compound (730 mg).

¹H NMR δ: 5.6(1H, m), 5.3(1H, m), 4.0(1H, m), 3.8–3.6 (3H, m), 3.5(1H, m), 3.3(1H, m), 3.2(1H, br), 2.8(1H, m), 2.3(2H, m), 0.91(3H, s), 0.91(9H, s), 0.90(9H, s), 0.58(3H, s), 0.10(3H, s), 0.06(3H, s), 0.05(3H, s).

(2) 1α,3β-dihydroxy-17β-(3-hydroxy-3-methylbutoxymethyl)androsta-5,7-diene

To 1α,3β-bis(tert-butyldimethylsilyloxy)-17β-(3-hydroxy-3-methylbutoxymethyl)androsta-5,7-diene (700 mg), was added a 1M tetra-n-butylammonium fluoride tetrahydrofuran solution (20 ml), followed by reaction for 6 hours. After adding ethyl acetate, the reaction mixture was washed with saturated brine, a saturated aqueous sodium bicarbonate solution and saturated brine. The organic layer was dried over anhydrous magnesium sulfate, evaporated under reduced pressure to remove the solvent and the resulting residue was purified by column chromatography (dichloromethane: methanol=9:1) to give the titled compound (0.41 g).

¹H NMR (DMSO-d6) δ: 5.5(1H, m), 5.3(1H, m), 4.6(1H, d, J=4.6 Hz), 4.4(1H, d, J=4.6 Hz), 4.1(1H, m), 3.5–3.3(3H, m), 3.2(1H, m), 2.8(1H, m), 2.3(1H, m), 2.1(1H, m), 1.1(6H, s), 0.8(3H, s), 0.5(3H, s).

¹³C NMR (DMSO-d6) δ: 140.2, 138.8, 119.5, 114.8, 71.9, 70.7, 68.1, 67.3, 63.2, 53.5, 49.2, 42.7, 41.8, 41.5, 40.3, 38.9, 37.4, 37.0, 29.7, 29.6, 25.3, 23.0, 19.5, 15.8, 12.0.

(3) 1α,3β-dihydroxy-17β-(3-hydroxy-3-methylbutoxymethyl)-9,10-secoandrosta-5,7,10(19)-triene 1α,3β-Dihydroxy-17β-(3-hydroxy-3-methylbutoxymethyl)androsta-5,7-diene (150 mg) was dissolved in tetrahydrofuran (200 ml), subjected to irradiation for 2 min. by 400 W high-pressure mercury lamp, refluxed for 2.5 hours and then evaporated to remove the solvent under reduced pressure. The resulting residue was subjected to high performance liquid chromatography (methanol:acetonitrile:water=3.5:2.5:4) to give the titled compound (33.0 mg).

¹H NMR δ: 6.4(1H, d, J=10.8 Hz), 6.1(1H, d, J=10.8 Hz), 5.3(1H, m), 5.0(1H, m), 4.4(1H, m), 4.2(1H, m), 3.8–3.5 (4H, m), 3.3(1H, m), 2.8(1H, m), 2.6(1H, m), 2.3(1H, m), 1.5(6H, s), 1.2(3H, s), 0.5(3H, s).

¹³C NMR δ: 147.6, 142.6, 133.0, 124.9, 117.2, 111.8, 73.3, 70.9, 70.6, 68.8, 66.8, 55.8, 50.4, 45.3, 45.0, 42.9, 41.3, 39.0, 29.5, 29.0, 25.2, 23.3, 22.6, 12.6.

Example 48

(1) 1α,3β-bis(tert-butyldimethylsilyloxy)-17-methylandrosta-5,7,17-triene

A suspension of 1α,3β-bis(tert-butyldimethylsilyloxy)-17-oxoandrosta-5,7-diene (723 mg, 1.36 mmol), methyltriphenylphosphonium bromide (632 mg, 1.77 mmol) and potassium tert-butoxide (198 mg, 1.77 mmol) in tetrahydrofuran (5 ml) was subjected to reflux under heating for 1 hour. The reaction mixture was returned to room temperature, mixed with hexane (20 ml) and filtered to remove insoluble material. The filtrate was washed with water twice, dried over anhydrous magnesium sulfate and evaporated under reduced pressure to remove the solvent. The thus obtained residue was purified by column chromatography (hexane: dichloromethane=9:1) to give the titled compound (599 mg, 83%) as a colorless oil.

IR(neat): 2954, 2929, 2887, 2856, 1462, 1371, 1254, 1097, 1082 cm⁻¹.

¹H NMR δ: 0.06(s, 3H), 0.07(s, 6H), 0.11(s, 3H), 0.74(s, 3H), 0.88(s, 9H), 0.89(s, 9H), 0.93(s, 3H), 2.46–2.65(m, 1H), 2.75–2.89(m, 1H), 3.70–3.75(m, 1H), 3.98–4.13(m, 1H), 4.65–4.75(m, 2H), 5.35–5.43(m, 1H), 5.56–5.64(m, 1H).

(2) 1α,3β-bis(tert-butyldimethylsilyloxy)-17β-(hydroxymethyl)androsta-5,7-diene To a solution of 1α,3β-bis(tert-butyldimethylsilyloxy)-17-methylandrosta-5,7,17-triene (593 mg, 1.12 mmol) in tetrahydrofuran (4 ml), was added dimer of 9-borabicyclo[3,3,1]nonane (273 mg, 1.12 mmol), followed by stirring at external temperature of 45° C. for 2 hours. After cooling the reaction mixture in an ice bath, a 3M aqueous sodium hydroxide solution (4 ml) and then 30% hydrogen peroxide solution (3 ml) were added dropwise, followed by stirring at room temperature for 2 hours. The reaction mixture was poured into water and extracted with ethyl acetate. The extract was washed with water and saturated brine, dried over anhydrous magnesium sulfate and evaporated under reduced pressure to remove the solvent. The thus obtained residue was purified by column chromatography (hexane:ethyl acetate=7:1) to give the titled compound (465 mg, 76%) as a white solid. The thus obtained compound had the same spectra as those of the compound obtained in Example 45(6).

(3) 1α,3β-bis(tert-butyldimethylsilyloxy)-17β-(methanesulfonyloxymethyl)androsta-5,7-diene A solution of 1α,3β-bis(tert-butyldimethylsilyloxy)-17β-(hydroxymethyl)androsta-5,7-diene (150 mg, 0.274 mmol) and triethylamine (0.153 ml, 1.10 mmol) in tetrahydrofuran (2.3 ml) was cooled to 0° C., followed by the addition of methanesulfonyl chloride (63 μl, 0.814 mmol) and stirring at 0° C. for 1 hour. The reaction mixture was diluted with hexane, washed with water and saturated brine, dried over anhydrous magnesium sulfate and evaporated under reduced pressure to remove the solvent. The thus obtained residue was purified by column chromatography (hexane:ethyl acetate=9:1) to give the titled compound (155 mg, 91%) as a colorless foam.

IR(neat): 2954, 2929, 2897, 2856, 1471, 1360, 1176, 1097, 1066 cm$^{-1}$.

$^{1}$H NMR δ: 0.05(s, 3H), 0.06(s, 6H), 0.11(s, 3H), 0.64(s, 3H), 0.88(s, 18H), 0.91(s, 3H), 3.00(s, 3H), 3.67–3.74(m, 1H), 3.97–4.12(m, 1H), 4.13–4.22(m, 1H), 4.23–4.32(m, 1H), 5.29–5.37(m, 1H), 5.55–5.62(m, 1H). UV λ$_{max}$ nm: 271, 282, 294.

(4) 1α,3β0-bis(tert-butyldimethylsilyloxy)-17β-(acetylthiomethyl)androsta-5,7-diene A mixture of 1α,3β-bis(tert-butyldimethylsilyloxy)-17β-(methanesulfonyloxymethyl)androsta-5,7-diene (155 mg, 0.248 mmol), potassium thioacetate (56.6 mg, 0.496 mmol) and 18-crown-6 (65.6 mg, 0.248 mmol) in tetrahydrofuran (4 ml) was subjected to reflux under heating for 20 hours. The reaction mixture was returned to room temperature. After adding a saturated aqueous ammonium chloride, the reaction mixture was poured into water and extracted with ethyl acetate. The extract was washed with water and saturated brine, dried over magnesium sulfate and evaporated under reduced pressure to remove the solvent. The thus obtained residue was purified by column chromatography (hexane:dichloromethane=3:12:1) to give the titled compound (135 mg, 90%) as a yellow oil.

IR(neat): 2954, 2929, 2897, 2856, 1693, 1471, 1360, 1254, 1099 cm$^{-1}$.

$^{1}$H NMR δ: 0.05(s, 3H), 0.06(s, 6H), 0.11(s, 3H), 0.60(s, 3H), 0.878(s, 9H), 0.882(s, 9H), 0.91(s, 3H), 2.32(s, 3H), 2.74(dd, J=12.9, 9.7 Hz, 1H), 3.04(dd, J=12.9, 5.3 Hz, 1H), 3.67–3.75(m, 1H), 3.97–4.12(m, 1H), 5.27–5.34(m, 1H), 5.54–5.61(m, 1H).

MS m/z: 604(M$^{+}$), 415(100%). UV λ$_{max}$ nm: 271, 282, 294.

(5) 1α,3β-bis(tert-butyldimethylsilyloxy)-17β-(3-hydroxy-3-methylbutylthiomethyl)androsta-5,7-diene To a solution of 1α,3β-bis(tert-butyldimethylsilyloxy)-17β-(acetylthiomethyl)androsta-5,7-diene (135 mg, 0.223 mmol) and 4-bromo-2-methylbutan-2-ol (186 mg, 1.12 mmol) in tetrahydrofuran (1.5 ml), was added a 1M potassium hydroxide methanol solution (1.5 ml), followed by stirring at room temperature for 1 hour. The reaction mixture was concentrated under reduced pressure, followed by the addition of a saturated aqueous ammonium chloride solution and the extraction with ethyl acetate. The extract was washed with water and saturated brine, dried over anhydrous magnesium sulfate and evaporated under reduced pressure to remove the solvent. The thus obtained residue was purified by preparative thin layer chromatography (4 sheets (each 0.5 mm thickness), dichloromethane:ethyl acetate=9:1, developed once) to give the titled compound (131 mg, 90%) as a colorless oil.

IR(neat): 3388, 2954, 2929, 2897, 2856, 1462, 1377, 1254, 1099, 1082 cm$^{-1}$.

$^{1}$H NMR δ: 0.05(s, 3H), 0.06(s, 6H), 0.11(s, 3H), 0.58(s, 3H), 0.88(s, 18H), 0.91(s, 3H), 1.23(s, 6H), 2.71(dd, J=11.8, 5.1 Hz, 1H), 2.75–2.87(m, 1H), 3.67–3.74(m, 1H), 3.96–4.12(m, 1H), 5.28–5.35(m, 1H), 5.54–5.61(m, 1H).

MS m/z: 648(M$^{+}$), 459(100%). UV λ$_{max}$ nm: 271, 282, 294.

(6) 1α,3β-dihydroxy-17β-(3-hydroxy-3-methylbutylthiomethyl)androsta-5,7-diene To a solution of 1α,3β-bis(tert-butyldimethylsilyloxy)-17β-(3-hydroxy-3-methylbutylthiomethyl)androsta-5,7-diene (130 mg, 0.215 mmol) in tetrahydrofuran (1 ml), was added a 1M tetra-n-butylammonium fluoride tetrahydrofuran solution (2.15 ml, 2.15 mmol), followed by reflux under heating for 5 hours. The reaction mixture was returned to room temperature, diluted with ethyl acetate, washed with water and saturated brine, dried over anhydrous magnesium sulfate and evaporated under reduced pressure to remove the solvent. The thus obtained residue was purified by preparative thin layer chromatography (3 sheets (each 0.5 mm thickness), dichloromethane:ethanol=9:1, developed once) to give the titled compound (75.9 mg, 84%) as a white solid.

$^{1}$H NMR (CD$_{3}$OD) δ: 0.66(s, 3H), 0.97(s, 3H), 1.24(s, 6H), 2.75(dd, J=12.1, 5.2 Hz, 1H), 2.81–2.94(m, 1H), 3.73–3.80(m, 1H), 3.92–4.10(m, 1H), 5.35–5.34(m, 1H), 5.62–5.71(m, 1H).

MS m/z: 420(M$^{+}$), 119(100%). UV λ$_{max}$ nm: 272, 282, 294.

(7) 1α,3β-dihydroxy-17β-(3-hydroxy-3-methylbutylthiomethyl)-9,10-secoandrosta-5,7,10(19)-triene 1α,3β-Dihydroxy-17β-(3-hydroxy-3-methylbutylthiomethyl)androsta-5,7-diene (60.5 mg, 0.144 mmol) was dissolved in ethanol (200 ml). While stirring the solution and bubbling argon thereinto at 0° C., the solution was irradiated by a 400 W high-pressure mercury lamp with a Vycor filter for 6.5 min. and then refluxed under heating for 2 hours. The reaction mixture was cooled to room temperature, evaporated under reduced pressure to remove the solvent and the thus obtained residue was purified by preparative thin layer chromatography (2 sheets (each 0.5 mm thickness), dichloromethane:ethanol=9:1, developed once; and 1 sheet (0.25 mm thickness), dichloromethane:ethyl acetate:ethanol 7:3: 0.5, developed three times) to give the titled compound (7.36 mg, 12%) as a colorless oil.

IR(neat): 3367, 2927, 2871, 2843, 1435, 1377, 1209, 1147, 1055 cm$^{-1}$.

$^1$H NMR δ: 0.51(s, 3H), 1.24(s, 6H), 2.70(dd, J=11.9, 4.9 Hz, 1H), 2.80–2.90(m, 1H), 4.17–4.28(m, 1H), 4.38–4.47 (m, 1H), 4.99(brs, 1H), 5.32(m, 1H), 6.01(d, J=11.3 Hz, 1H), 6.37(d, J=11.3 Hz, 1H).

MS m/z: 420(M$^+$), 134(100%). UV $\lambda_{max}$ nm: 262.

Test Example 1

Active vitamin $D_3$ (1α,25 (OH)$_2$vitamin $D_3$) dissolved in ethanol at the concentration of 125 μg/ml, Compounds 1 to 13 (the vitamin D derivatives obtained in the above Examples) dissolved in ethanol at the concentration of 500 μg/ml and ethanol alone (as control) were percutaneously applied once to the dorsal skin of respective 8-week-old male Balb/c mice (approximately 1.5×2.0 cm$^2$). The dosage was 2 ml/kg and each mouse received a necklace to prevent ingestion. On the next day, the application areas were cleaned and necklaces were removed from the mice. Two days after the application, blood was drawn from each mouse in order to measure the ionized calcium level in the blood by an ion selective electrode method. In this experiment, each group contained 3 mice. Results are shown in Table 18. The ionized calcium levels in the Table indicate the mean values.

Test Example 2

Keratinocytes derived from human neonatal foreskin (Clonetics) were inoculated in 96 well-plates (COSTAR 3595) at 2×10$^3$ cells/well. Active vitamin $D_3$ (1α,25(OH)$_2D_3$) and Compounds 1 to 13 at various concentrations were added to respective wells and cultured at 2×10$^3$ cells/200 μl/well in KGM-2 medium for 3 days at 37° C. in 5% CO$_2$ and 95% air. After adding [$^3$H] thymidine at 7.4 kBq/well, the cell culture was continued for further 1 day. After washing the wells with phosphate buffer free of calcium and magnesium (Dulbecco PBS(−), NISSUI, code 05913, pH 7.3 to 7.65) once, the cells were stripped using 0.25% tyrosine. The [$^3$H] thymidine uptake of the cells was measured by a liquid scintillation counter (1450 microbeta, WALLAC). Results are shown in Table 18. In the Table, the inhibition of human keratinocyte proliferation is expressed as follows: the relative value of each Compound with respect to active vitamin $D_3$=[IC$_{50}$ (mol/l) of 1α,25(OH)$_2$vitamin $D_3$]/[IC$_{50}$ (mol/l) of each Compound]

TABLE 18

|  | Dosage (μg/kg) | Ionized Ca level (mmol/l) | Human keratinocyte proliferation inhibition (relative value) |
| --- | --- | --- | --- |
| Control | — | 1.34 | — |
| 1α, 25(OH)$_2D_3$ | 250 | 2.66 | 1.0 |
| Compound 1 | 1000 | 1.52 | 0.6 |
| Compound 2 | 1000 | 2.12 | 1.9 |
| Compound 3 | 1000 | 1.81 | 1.2 |
| Compound 4 | 1000 | 1.68 | 0.7 |
| Compound 5 | 1000 | 1.63 | 1.8 |
| Compound 6 | 1000 | 2.32 | 4.1 |
| Compound 7 | 1000 | 1.85 | 1.5 |
| Compound 8 | 1000 | 1.93 | 1.7 |
| Compound 9 | 1000 | 2.33 | 2.1 |
| Compound 10 | 1000 | 2.38 | 1.7 |
| Compound 11 | 1000 | 2.38 | 23.0 |
| Compound 12 | 1000 | 2.34 | 2.7 |
| Compound 13 | 1000 | 2.38 | 10.7 |

Compound 1 is 1α,3β-dihydroxy-17-(3-hydroxy-3-methylbutoxymethyl)-9,10-secoandrosta-5,7,10(19),16-tetraene obtained in Example 23(4), Compound 2 is 17-(4-ethyl-4-hydroxyhexyloxymethyl)-1α,3β-dihydroxy-9,10-secoandrosta-5,7,10(19),16-tetraene obtained in Example 6(3), Compound 3 is 1α,3β-dihydroxy-17-(5-hydroxy-5-methylhexyloxymethyl)-9,10-secoandrosta-5,7,10(19),16-tetraene obtained in Example 7(3), Compound 4 is 1α,3β-dihydroxy-17-(4-hydroxy-4-methylpentyloxymethyl)-9,10-secoandrosta-5,7,10(19),16-tetraene obtained in Example 5(3), Compound 5 is 1α,3β-dihydroxy-17-(4-hydroxy-4-methyl-2-pentynyloxymethyl)-9,10-secoandrosta-5,7,10(19),16-tetraene obtained in Example 8(3), Compound 6 is 17-{4-ethyl-4-hydroxy-(2E)-hexenyloxymethyl}-1α,3β-dihydroxy-9,10-secoandrosta-5,7,10(19),16-tetraene obtained in Example 10(3), Compound 7 is 17-(4-ethyl-4-hydroxy-2-hexynyloxymethyl)-1α,3β-dihydroxy-9,10-secoandrosta-5,7,10(19),16-tetraene obtained in Example 11(3), Compound 8 is 1α,3β-dihydroxy-17-(4-hydroxy-4-methyl-2-pentynylthiomethyl)-9,10-secoandrosta-5,7,10 (19),16-tetraene obtained in Example 39, Compound 9 is 1α,3β-dihydroxy-17-(3-ethyl-3-hydroxypentyloxymethyl)-9,10-secoandrosta-5,7,10(19),16-tetraene obtained in Example 25(4), Compound 10 is 17-(4-ethyl-4-hydroxy-2-hexynylthiomethyl)-1α,3β-dihydroxy-9,10-secoandrosta-5,7,10(19),16-tetraene obtained in Example 40, Compound 11 is 1α,3β-dihydroxy-20-(4-hydroxy-4-methyl-2-pentynyloxy)-20-methyl-9,10-secopregna-5,7,10(19),16-tetraene obtained in Example 15(3), Compound 12 is 1α,3β-dihydroxy-20-(5-hydroxy-5-methylhexyloxy)-20-methyl-9,10-secopregna-5,7,10(19),16-tetraene obtained in Example 14 and Compound 13 is 1α,3β-dihydroxy-20-(4-ethyl-4-hydroxy-2-hexynyloxy)-20-methyl-9,10-secopregna-5,7,10 (19),16-tetraene obtained in Example 18(3).

INDUSTRIAL APPLICABILITY

Vitamin D derivatives of the present invention exhibit excellent physiological activity and have reduced hypercalcemic effect as compared with conventional vitamin D derivatives; they may be useful as medicines for diseases, to which the administration of vitamin D derivatives has been restricted because of hypercalcemia, etc.

The invention claimed is:

1. A vitamin D derivative of Formula (1):

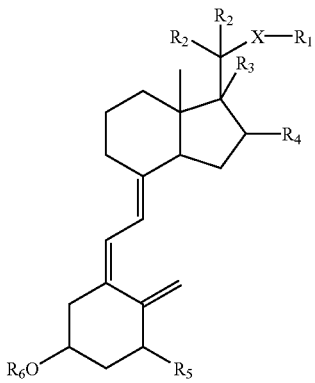

Formula (1)

wherein
in Formula (1), X is oxygen or sulfur;
$R_1$ is Formula (2)

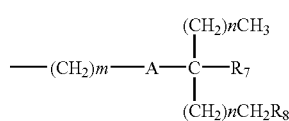

Formula (2)

wherein
in Formula (2), A is —CO—, —$CR_9R_{10}$— in which $R_9$ and $R_{10}$ are hydrogen or hydroxy, —$CR_{11}$=$CR_{12}$— in which $R_{11}$ and $R_{12}$ are hydrogen or alkyl or —C≡C—; $R_7$ and $R_8$ are hydrogen or hydroxy which may have a protecting group; m is 1 to 2; and n is a number from 0 to 2;

$R_2$ is the same at both positions and is hydrogen or alkyl;

$R_3$ and $R_4$ are hydrogen or alkyl or $R_3$ and $R_4$ together form a double bond between the 16- and 17-positions;

$R_5$ is hydrogen or —$OR_{13}$ in which $R_{13}$ is hydrogen or a protecting group; and $R_6$ is hydrogen or a protecting group.

2. The vitamin D derivative as set forth in claim 1, wherein in Formula (1), X is oxygen or sulfur; $R_1$ is Formula (2) wherein A is —CO—, —$CH_2$—, —CH(OH)—, —CH=CH— or —C≡C—, $R_7$ is hydroxy, $R_8$ is hydrogen, n is a number from 0 to 1; $R_2$ is hydrogen or $C_{1-4}$ alkyl; $R_3$ and $R_4$ is hydrogen or $R_3$ and $R_4$ together form a double bond between the 16- and 17-positions; $R_5$ is hydroxy; and $R_6$ is hydrogen.

3. The vitamin D derivative as set forth in claim 1, wherein in Formula (1), X is oxygen or sulfur; $R_1$ is Formula (2) wherein A is —CO—, —$CH_2$—, —CH(OH)—, —CH=CH— or C≡C—, $R_7$ is hydroxy, $R_8$ is hydrogen, n is a number from 0 to 1; $R_2$ is hydrogen or methyl; $R_3$ and $R_4$ together form a double bond between the 16- and 17-positions; $R_5$ is hydroxy; and $R_6$ is hydrogen.

4. The vitamin D derivative as set forth in claim 1, wherein in Formula (1), X is oxygen or sulfur; $R_1$ is Formula (2) wherein A is —CO—, —$CH_2$—, —CH=CH— or —C≡C—, $R_7$ is hydroxy, $R_8$ is hydrogen, m is 1 and n is a number from 0 to 1; $R_2$ is hydrogen or methyl, $R_3$ and $R_4$ together form a double bond between the 16- and 17-positions; $R_5$ is hydroxy; and $R_6$ is hydrogen.

5. The vitamin D derivative as set forth in claim 1, wherein in Formula (1), X is oxygen; $R_1$ is Formula (2) wherein A is —$CH_2$— or —C≡C—, $R_7$ is hydroxy, $R_8$ is hydrogen, m is 1 and n is a number from 0 to 1; $R_2$ is hydrogen or methyl; $R_3$ and $R_4$ together form a double bond between the 16- and 17-positions; $R_5$ is hydroxy; and $R_6$ is hydrogen.

6. The vitamin D derivative as set forth in claim 1, wherein in Formula (1), X is oxygen; $R_1$ is Formula (2) wherein A is —C≡C—, $R_7$ is hydroxy, $R_8$ is hydrogen, m is 1 and n is 0; $R_2$ is hydrogen or methyl; $R_3$ and $R_4$ together form a double bond between the 16- and 17-positions; $R_5$ is hydroxy; and $R_6$ is hydrogen.

7. The vitamin D derivative as set forth in claim 1, wherein in Formula (1), X is oxygen; $R_1$ is Formula (2) wherein A is —$CH_2$—, $R_7$ is hydroxy, $R_8$ is hydrogen, n is a number from 0 to 1; $R_2$ is hydrogen; $R_3$ and $R_4$ are hydrogen; $R_5$ is hydroxy; and $R_6$ is hydrogen.

8. A pharmaceutical composition comprising the vitamin D derivative as set forth in any one of claims 1 to 7.

9. A method for the treatment of skin disease, comprising administering to a patient in need thereof an amount sufficient for said treatment of a vitamin D derivative as set forth in claim 1.

10. The method of claim 9 wherein said patient is one whose skin disease is psoriasis.

11. The pharmaceutical composition of claim 8 formulated as a topical preparation selected from the group consisting of an ointment, a cream and a lotion.

* * * * *